US008062756B2

(12) United States Patent
Bocian et al.

(10) Patent No.: US 8,062,756 B2
(45) Date of Patent: *Nov. 22, 2011

(54) STEPWISE GROWTH OF OLIGOMERIC REDOX-ACTIVE MOLECULES ON A SURFACE WITHOUT THE USE OF PROTECTING GROUPS

(75) Inventors: David F. Bocian, Riverside, CA (US); Jonathan S. Lindsey, Raleigh, NC (US); Jieying Jiao, Riverside, CA (US)

(73) Assignees: The Regents oft the University of California, Oakland, CA (US); North Carolina State University, Raleigh, NC (US)

( * ) Notice: Subject to any disclaimer, the term of this patent is extended or adjusted under 35 U.S.C. 154(b) by 1179 days.

This patent is subject to a terminal disclaimer.

(21) Appl. No.: 11/509,319

(22) Filed: Aug. 23, 2006

(65) Prior Publication Data

US 2007/0123618 A1 May 31, 2007

Related U.S. Application Data

(60) Provisional application No. 60/711,966, filed on Aug. 26, 2005.

(51) Int. Cl.
*B32B 15/04* (2006.01)
(52) U.S. Cl. ........................ 428/457; 428/543; 528/353
(58) Field of Classification Search .................. 528/353; 428/457, 543
See application file for complete search history.

(56) References Cited

U.S. PATENT DOCUMENTS

| | | | |
|---|---|---|---|
| 5,091,502 A | 2/1992 | Narang et al. |
| 5,252,730 A | 10/1993 | Mackey |
| 5,286,877 A | 2/1994 | Behling et al. |
| 5,286,887 A | 2/1994 | Traylor et al. |
| 5,312,896 A | 5/1994 | Bhardwaj et al. |
| 5,327,373 A | 7/1994 | Liu et al. |
| 5,352,764 A | 10/1994 | Mackey |
| 5,360,880 A | 11/1994 | Pashley et al. |
| 5,424,974 A | 6/1995 | Liu et al. |
| 6,107,480 A | 8/2000 | Funken et al. |
| 6,114,099 A | 9/2000 | Liu et al. |
| 6,208,553 B1 | 3/2001 | Gryko et al. |
| 6,212,093 B1 | 4/2001 | Lindsey |
| 6,235,895 B1 | 5/2001 | McEwan et al. |
| 6,272,038 B1 | 8/2001 | Clausen et al. |
| 6,324,091 B1 | 11/2001 | Gryko et al. |
| 6,381,169 B1 | 4/2002 | Bocian et al. |
| 6,407,330 B1 | 6/2002 | Lindsey et al. |
| 6,420,648 B1 | 7/2002 | Lindsey |
| 6,429,310 B2 | 8/2002 | Kobuke et al. |
| 6,451,942 B1 | 9/2002 | Li et al. |
| 6,602,998 B2 | 8/2003 | Kobuke et al. |
| 6,653,415 B1 | 11/2003 | Bottcher et al. |
| 6,657,884 B2 | 12/2003 | Bocian et al. |
| 6,674,121 B2 | 1/2004 | Misra et al. |
| 6,728,129 B2 | 4/2004 | Lindsey et al. |
| 6,777,516 B2 | 8/2004 | Li et al. |
| 7,005,237 B2 | 2/2006 | Lindsey et al. |
| 7,166,327 B2 | 1/2007 | Afzali-Ardakani et al. |
| 7,192,650 B2 * | 3/2007 | Kobuke et al. ................ 428/457 |
| 7,452,572 B1 | 11/2008 | Bocian et al. |
| 2002/0001973 A1 | 1/2002 | Wu et al. |
| 2002/0105897 A1 | 8/2002 | McCreery |
| 2004/0087177 A1 | 5/2004 | Colburn et al. |
| 2004/0244831 A1 | 12/2004 | Lindsey |
| 2004/0253756 A1 | 12/2004 | Cok et al. |
| 2005/0054215 A1 | 3/2005 | Buriak et al. |
| 2008/0280047 A1 | 11/2008 | Bocian et al. |

FOREIGN PATENT DOCUMENTS

| | | |
|---|---|---|
| WO | WO 01/03126 A2 | 1/2001 |
| WO | WO 02-077633 | 10/2002 |
| WO | WO 03-038886 | 5/2003 |
| WO | WO 03-052835 | 6/2003 |
| WO | WO 03/071552 | 8/2003 |
| WO | WO 2005/086826 | 9/2005 |
| WO | WO 2007-025114 | 3/2007 |

OTHER PUBLICATIONS

International Search Report and Written Opinion dated Nov. 10, 2005 issued in PCT/2005/07639 (WO2005086826).
Preliminary Examination dated May 30, 2006 issued in PCT/2005/07639 (WO2005086826).
Chinese Office Action dated Feb. 9, 2009 issued in CN 200580015129.9.
Chinese Notification of Grant dated Aug. 28, 2009 issued in CN 200580015129.9.
US Office Action dated Jun. 26, 2006 issued in U.S. Appl. No. 10/800,147.
US Final Office Action dated Mar. 23, 2007 issued in 10/800,147.
US Office Action dated Nov. 19, 2007 issued in U.S. Appl. No. 10/800,147.
US Notice of Allowance dated Jun. 26, 2008 issued in U.S. Appl. No. 10/800,147.
US Interview Summary dated Aug. 21, 2008 issued in U.S. Appl. No. 10/800,147.
US Office Action dated Mar. 23, 2010 issued in U.S. Appl. No. 12/265,990.
Buriak (1999) *Chem. Commun.* 1051-1060.
Cleland et al. (1995) *J. Chem. Soc. Faraday Trans.* 91: 4001-4003.
Haber et al. (2000) *J. Phys. Chem. B* 104: 9947-9950.
Flamers et al. (2000) *Acc. Chem. Res.* 33: 617-624.
Linford et al. (1995) *J. Am. Chem. Soc.* 117: 3145-3155.
Preliminary Examination Report dated May 11, 2007 issued in PCT/2006/033195 (WO2007025114).
International Search Report and Written Opinion dated May 11, 2007 issued in PCT/2006/033195 (WO2007025114).
Balakumar et al. (2004), Diverse Redoc-Active Molecules Bearing O-, S-, or Se-Terminated Tethers for Attachment to Silicon in Studies of Molecular Information Storage, *J. Org. Chem.* 69:1435-1443.

(Continued)

*Primary Examiner* — Bernard Lipman
(74) *Attorney, Agent, or Firm* — Tom Hunter; Weaver Austin Villeneuve & Sampson LLP

(57) ABSTRACT

This invention provides a procedure for growing oligomers via a stepwise process. The oligomers can include porphyrins, which have been previously shown to be attractive candidates for molecular-based information storage. The stepwise synthesis procedure requires no protecting groups, thus eliminating protection/deprotection reactions that add complexity to the process.

31 Claims, 37 Drawing Sheets

OTHER PUBLICATIONS

Battioni et al. (1991), Preparation of Functionalized Polyhalogenated Tetraaryl-porphyrins by Selective Substitution of the p-Fluorine of mesoTetra-(pentafluorophenyl) porphyrins, *Tetrahedron Lett.* 32:2893-2896.

Carcel et al. (2004), Porphyrin Architectures Tailored for Studies of Molecular Information Storage, *J,Org.Chem.* 69:6739-6750.

Clausen et al. (2000), Synthesis of Thiol-Derivatized Porphyrin Dimers and Trimers for Studies of Architectural Effects on Multibit Information Storage, *J. Org. Chem.* 65:7363-7370.

Fan et al. (2005), 1,9-Bis (*N,N*-dimethylaminomethyl) dipyrromethanes in the synthesis of porphyrins bearing one or two *meso* substituents, *Tetrahedron* 61:10291-10302.

Geier et al. (2001), A survey of acid catalysts in dipyrromethanecarbinol condensations leading to *meso*-substituted porphyrins, *J. Porphyrins Phthalocyanines* 5 :810-823.

Kuhr et al. (2004), Molecular Memories Based on a CMOS Platform, *Mater.Res. Soc. Bull.*, pp. 838-842.

Littler et al. (1999), Investigation of Conditions Giving Minimal Scramlbling in the Synthesis of trans-Porphyrins from Dipyrromethanes and Aldehydes, *J. Org. Chem.* 64:2864-2872.

Liu et al. (2004), Synthesis of Porphyrins Bearing hydrocarbon Tethers and Facile Covalent Attachment to Si(100), *J. Org. Chem.* 69:5568-5577.

Loewe et al. (2004), Porphyrins Bearing Mono or Tripodal Benzylphosphonic Acid Tethers for Attachment to Oxide Surfaces, *J. Org. Chem.* 69:1453-1460.

Lysenko et al. (2005), Multistate molecular information storage using S-acetylthio-derivatized dyads of triple-decker sandwich coordination compounds, *J. Porphyrins Phthalocyanines* 9:491-508.

Muthukumaran et al. (2004), Porphyrins Bearing Arylphosphonic Acid Tethers for Attachment to Oxide Surfaves, *J. Org. Chem.* 69:1444-1452.

Padmaja et al. (2005), A Compact All-Carbon Tripodal Tether Affords High Coverage of Porphyrins on Silicon Surfaces, *J. Org. Chem.* 70:7972-7978.

Rao et al. (2000), Rational Syntheses of Porphyrins Bearing up to Four Different Meso Substituents, *J. Org. Chem.* 65:7323-7344.

Roth et al. (2000), Molecular approach toward information storage based on the redox properties of porphyrins in self-assembled monolayers, *J. Vac. Sci. Technol. B.* 18:2359-2364.

Roth et al. (2002), Measurements of Eloectron-Transfer Rate of Charge-Storage Molecular Monolayers on Si(100). Toward Hybrid Molecular/Semiconductor Information Storage Devices, *J. Am. Chem. Soc.*, 125:505-517.

Thamyongkit et al. (2006) Alkylthio Unit as an a-Pyrrole Protecting Group for use in Dipyrromethane Synthesis, *J. Org. Chem.* 71:903-910.

Wei et al. (2004), Alkylthio Unit as an α-Pyrrole Protecting Group for Use in Dipyrromethane Synthesis, *J. Org. Chem.* 69:1461-1469.

Wei et al. (2005), Structural and Electron-Transfer Characteristics of Carbo-Tethered Porphyrin Monolayers on Si(100), *J. Phys. Chem. B* 109:6323-6330.

European Supplementary Search Report dated Nov. 15, 2010 issued in EP05730161.

Liu et al. (2003) "Molecular Memories That Survive Silicon Device Processing and Real-World Operation" *Science, American Association for the Advancement of Science*, 302(5650):1543-1545.

Schweikart et al. (2003) "Synthesis and Characterization of Bis(S-acetylthio)-Derivatized Europium Triple-Decker Monomers and Oligomers" *Inorganic Chemistry* 42(23):7431-7446.

* cited by examiner

Scheme 1

M = Zn, Ar = p-Tol unless noted otherwise

| R | Ar | |
|---|---|---|
|  |  | Zn-13 |
|  |  | Zn-14 |

Scheme 3

16a

18% ↓ (1) EtMgBr, toluene
(2) p-toluoyl chloride
(3) Bu₂SnCl₂, TEA, CH₂Cl₂

17

30% ↓ (1) NaBH₄
(2) 16b, Yb(OTf)₃, CH₂Cl₂
(3) DDQ

2; M = H, H

76% ↓ Zn(OAc)₂·2H₂O

Zn-2; M = Zn

Scheme 7

Scheme 8

38; R = H; M = H, H

71% ↓ (1) NBS, pyridine
(2) Zn(OAc)₂·2H₂O

Zn-31; R = Br, M = Zn

STEPWISE GROWTH OF OLIGOMERIC REDOX-ACTIVE MOLECULES ON A SURFACE WITHOUT THE USE OF PROTECTING GROUPS

CROSS-REFERENCE TO RELATED APPLICATIONS

This application claims priority to and benefit of U.S. Ser. No. 60/711,966, filed on Aug. 26, 2005, which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported, in part, by DARPA/DMEA Award Nos. H94003-04-2-0404 and H94003-05-2-0504. The Government of the United States of America has certain rights in this application.

FIELD OF THE INVENTION

This invention pertains to the field of organic chemistry. In particular, this invention provides a novel approach to the stepwise synthesis of polymeric molecules without the use of protecting groups.

BACKGROUND OF THE INVENTION

The ever-increasing demand for high-density information storage calls for new approaches for storage of information. The ability to store information in molecular structures provides perhaps the ultimate in data storage density.

The design and synthesis of redox-active molecules for surface attachment provides the foundation for the fabrication of information storage devices that function on the basis of stored charge (see, e.g., Roth et al. (2000) *J. Vac. Sci. Technol. B*, 18: 2359-2364; Liu et al. (2003) *Science*, 302: 1543-1545; U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, etc.). Such surface-attached redox-active molecules can also be used in the fabrication of numerous other devices including, but not limited to solar cells (see, e.g., U.S. Pat. Nos. 6,407,330 and 6,420,648, U.S. Patent Publication 20040244831 A1, and the like). A key feature for the commercialization of redox-based molecular information storage is that each memory cell stores sufficient charge for reliable readout. Similarly a key feature for the commercialization of solar cells is that each cell produce adequate power. Both advantages can be achieved by increasing the packing density of redox-active molecules or molecular subunits on a particular substrate.

An attractive strategy for achieving increased charge density (redox-active unit packing) is to use the vertical dimension. In various embodiments, this can utilize a dyad, triad, or multad of charge storage molecules or subunits. One method for constructing the device would be to attach a pre-synthesized oligomer to the electroactive surface. In this approach, however, it is possible that the oligomers may aggregate and/or may not undergo facile self assembly.

An alternative approach is to grow the oligomer in a stepwise fashion. Such an assembly process, however, has heretofore required the use of protecting groups. The monomeric building blocks were prepared with at least one protecting group, and after each coupling reaction, the protecting group was removed. Thus, one cycle of coupling required three reactions: protecting group introduction, coupling, and protecting group removal. A further limitation stems from the difficulty, in many instances, of identifying suitable conditions for protecting group removal that are compatible with the protected molecules, the components in the molecular architecture under assembly, and the underlying substrate.

SUMMARY OF THE INVENTION

This invention provides a novel approach to stepwise synthesis that eliminates the use of protecting groups. The method can be used to create any of a wide variety of oligomers/polymers containing identical or different monomeric or polymeric subunits. In certain embodiments the stepwise synthesis methods are particularly well suited to the construction of molecular memory elements and/or light harvesting elements.

Thus, in certain embodiments this invention provides a method of forming an oligomeric molecule on a substrate. The method typically involves a) providing a substrate having attached thereto a linker bearing a free reactive group A or a first monomer bearing a free reactive group A; b) contacting the linker or the first monomer with a second monomer comprising two identical free reactive groups B where B is reactive with A, whereby the second monomer couples to the first monomer via a reaction between A and one of the reactive groups B; and c) contacting the second monomer with a third monomer comprising two identical free reactive groups A, whereby the third monomer couples to the second monomer via a reaction between one of reactive groups A, and a the free reactive group B on the second monomer, thereby forming an oligomeric molecule attached to the substrate. In various embodiments the providing comprises coupling a first monomer to the substrate where the first monomer after coupling to the surface provides a free reactive group A. In certain embodiments the method can, optionally, further comprise repeating step (b) and/or step (c) one or more times to further extend the oligomeric molecule. In various embodiments the method, optionally further comprises contacting the free terminal monomer with a monomer comprising a single free reactive group B when the free terminal monomer comprises a free reactive group A or contacting the free terminal monomer with a monomer comprising a single free reactive group A when the free terminal monomer comprises a free reactive group B, in certain embodiments the method further comprises contacting the free terminal monomer with a monomer comprising a single free reactive group B when the free terminal monomer comprises a free reactive group A or contacting the free terminal monomer with a monomer comprising a single free reactive group A when the free terminal monomer comprises a free reactive group B. In various embodiments second monomer has the formula: A-$M^2$-A, and and the third monomer has the formula B-$M^3$-B where A and B are free reactive groups selected such that A and B react with each other to form a covalent linkage; and $M^2$ and $M^3$ are independently selected from the group consisting of a charge storage moiety, a charge separation moiety, a spacer, an electrolyte, and a tether, in certain embodiments the method further comprises performing a cross-linking reaction after coupling each monomer, in certain embodiments $M^2$ and $M^3$ are the same. In certain embodiments, A and B are pairs of reactive groups selected from Table 1. In certain embodiments $M^2$ and $M^3$ are joined by a linkage selected from the group consisting of acyl hydrazone, imine, salicylaldimine, H-bonded acyl hydrazone, vinyl, urea, carbamate, carboxy amide, imide, thiourea, thiocarbamate, amide-alkyl-thiol, ether, ether, phenacyl ether, α-ether-acetamide, α-ester-acetamide, amide, sulfonamide, alkyl boronate, thioether, acetal, and hydroxyalkylamine. In various embodiments $M^2$ and $M^3$ are charge storage moieties comprising a redox-active molecule, in certain embodiments $M^2$ and $M^3$ are redox-active molecules selected from the group consisting of porphyrinic macrocycle, a sandwich compound of porphyrinic macrocycles, a lanthanide triple decker sandwich coordination compound, and a metallocene, in certain embodiments $M^2$ and $M^3$ are redox-active porphyrinic macrocycles independently selected from the group consisting of porphyrins, chlorins, bacteriochlorins, isobacteriochlorins, oxochlorins, dioxobacteriochlorins, dioxoisobacteriochlorins, pyrophorbines, bacteriopyrophorbines, phthalocyanines, naphthalocyanines, tetraazaporphyrins, porphyrazines, benzazoloporphyrazines, core modified porphyrinic derivatives, expanded porphyrinic derivatives, and contracted porphyrinic derivatives. In various embodiments the method forms an oligomeric molecule ranging in length from 2 to about 20 monomers, in certain embodiments the monomers comprising the oligomeric molecule are joined by a linkage selected from the group consisting of acyl hydrazone, imine, salicylaldimine, H-bonded acyl hydrazone, vinyl, urea, carbamate, carboxy amide, imide, thiourea, thiocarbamate, amide-alkyl-thiol, ether, ether, phenacyl ether, α-ether-acetamide, α-ester-acetamide, amide, sulfonamide, alkyl boronate, thioether, acetal, and hydroxyalkylamine.

In certain embodiments the substrate comprises an electrode and the substrate and oligomeric molecule form a light harvesting rod, in certain embodiments the substrate and oligomeric molecule form an intrinsic rectifier of excited-state energy and/or an intrinsic rectifier of holes. In various embodiments the substrate and oligomeric molecule form light harvesting rods are not greater than 500 nanometers in length. In certain embodiments the substrate comprises a first electrode and the oligomeric molecule and substrate form a molecular memory element. In various embodiments the oligomeric molecule comprises at least two meso-coupled porphyrinic macrocycles and/or at least two beta-coupled porphyrinic macrocycles, in certain embodiments the substrate is selected from the group consisting of a transparent substrate, an opaque substrate and a reflective substrate.

24. The method of any one of claims 1 or 11, where $M^1$, $M^2$, and/or $M^3$, have the formula show in Formula II, where M is present or absent and when present is selected from the group consisting of a metal, and a metalloid; $K^1$, $K^2$, $K^3$, and $K^4$ are independently selected from the group consisting of a group IV element, a group V element, a group VI element, and CH; $S^1$, $S^2$, $S^3$, and $S^4$ are substituents independently selected from the group consisting of aryl, phenyl, cycloalkyl, alkyl, halogen, alkoxy, alkylthio, perfluoroalkyl, alkenyl, alkynyl, perfluoroaryl, pyridyl, cyano, thiocyanato, nitro, amino, alkylamino, acyl, sulfoxyl, sulfonyl, imido, amido, imidazolyl, and carbamoyl, where the substituents provide a redox potential range of less than about 2 volts, in certain embodiments $K^1$, $K^2$, $K^3$, and $K^4$ are independently selected from the group consisting of N, O, S, Se, Te, and CH; in certain embodiments M is present and is selected from the group consisting of Zn, Mg, Cd, Hg, Cu, Ag, Au, Ni, Pd, Pt, Co, Rh, Ir, Mn, B, Al, Ga, Fe, In, Pb, and Sn. In certain embodiments $S^1$, $S^2$, $S^3$, $S^4$ are all the same, in certain embodiments $S^1$ and $S^4$ are the same and/or $S^2$ and $S^3$ are the same, in certain embodiments $K^1$, $K^2$, $K^3$, and $K^4$ are all the same (e.g., all N). In various embodiments the substrate comprises a material selected from the group consisting of silicon, germanium, silver, gold, copper, titanium, tantalum, tungsten, a doped silicon, a doped germanium, a silicon oxide, a germanium oxide, a silver oxide, a gold oxide, a copper oxide, a titanium oxide, a tantalum oxide, a tungsten oxide, a silicon nitride, a germanium nitride, a silver nitride, a gold nitride, a copper nitride, a titanium nitride, a tantalum nitride, a tungsten nitride, a carbon containing substrate, and a polymer (e.g., an insulating polymer, a conducting polymer, etc.). In certain embodiments the substrate comprises Si(100).

Also provided is a kit for the assembly of an oligomeric molecule. The kit typically comprises a container containing a first monomer having the formula $A-M^1-A$; and a container containing a second monomer having the formula: $B-M^2-B$ where: A and B are free reactive groups selected such that A and B react with each other to form a covalent linkage; and $M^1$ and $M^2$ are independently selected from the group consisting of a charge storage moiety, a charge separation moiety, a spacer, an electrolyte, and a tether. In certain embodiments A and B are pairs of reactive groups selected from Table 1. In certain embodiments $M^1$ and $M^2$ are charge storage moieties comprising a redox-active molecule. In various embodiments $M^1$ and $M^2$ are redox-active molecules selected from the group consisting of porphyrinic macrocycle, a sandwich compound of porphyrinic macrocycles, a lanthanide triple decker sandwich coordination compound, and a metallocene. In various embodiments $M^1$ and $M^2$ are redox-active porphyrinic macrocycles independently selected from the group consisting of porphyrins, chlorins, bacteriochlorins, isobacteriochlorins, oxochlorins, dioxobacteriochlorins, dioxoisobacteriochlorins, pyrophorbines, bacteriopyrophorbines, phthalocyanines, naphthalocyanines, tetraazaporphyrins, porphyrazines, benzazoloporphyrazines, core modified porphyrinic derivatives, expanded porphyrinic derivatives, and contracted porphyrinic derivatives, in certain embodiments A and B are selected such that reaction of A with B forms a linkage selected from the group consisting of acyl hydrazone, imine, salicylaldimine, H-bonded acyl hydrazone, vinyl, urea, carbamate, carboxy amide, imide, thiourea, thiocarbamate, amide-alkyl-thiol, ether, ether, phenacyl ether, α-ether-acetamide, α-ester-acetamide, amide, sulfonamide, alkyl boronate, thioether, acetal, and hydroxyalkylamine. In various embodiments $M^1$ and/or $M^2$ have the formula of Formula II, e.g., with substituents as described herein.

In various embodiments this invention also provides a composition, a chip, or a device, comprising an array of electrodes, where a plurality of the electrodes each comprise a redox-active molecule electrically coupled to an electrode, where the redox-active molecule is an oligomeric molecule synthesized in a stepwise synthesis method as described herein.

This invention also provides an apparatus comprising a fixed electrode electrically coupled to a storage medium where the storage medium comprises a redox-active molecule synthesized in a stepwise synthesis method as described herein.

in certain embodiments this invention provides a light harvesting array comprising: a first substrate comprising a first electrode; and a layer of light harvesting rods electrically coupled to the first electrode, the light harvesting rods comprising an oligomer of porphyrinic macrocycles coupled to the substrate, where the oligomer comprises monomeric units of porphyrinic macrocycles; and where oligomer is synthesized in a stepwise synthesis method as described herein, in certain embodiments the porphyrinic macrocycles are selected from the group consisting of porphyrins, chlorins, bacteriochlorins, isobacteriochlorins, oxochlorins, dioxobacteriochlorins, dioxoisobacteriochlorins, pyrophorbines, bacteriopyrophorbines, phthalocyanines, naphthalocyanines, tetraazaporphyrins, porphyrazines, benzazoloporphyrazines, core modified porphyrinic derivatives, expanded porphyrinic derivatives, and contracted porphyrinic derivatives, in certain embodiments the first substrate is selected from the group consisting of a transparent substrate, an opaque substrate, and a reflective substrate, in certain embodiments the electrode is metallic or nonmetallic (e.g., a conducting polymer, and the like), in certain embodiments the oligomer is oriented substantially perpendicularly to the substrate, in certain embodiments the oligomer is an intrinsic rectifier of excited-state energy and/or an intrinsic rectifier of holes. In various embodiments the light harvesting array further comprises a second substrate comprising a second electrode, with the first and second substrate being positioned to form a space there between, and with at least one of (i) the first substrate and the first electrode and (ii) the second substrate and the second electrode being transparent, in certain embodiments the light harvesting array further comprises an electrolyte in the space between the first and second substrates, in certain embodiments the electrolyte comprises a mobile charge carrier in the electrolyte. In various embodiments the light harvesting rod is electrically coupled to the second electrode.

DEFINITIONS

The term "oxidation" refers to the loss of one or more electrons in an element, compound, or chemical substituent/subunit. In an oxidation reaction, electrons are lost by atoms of the element(s) involved in the reaction. The charge on these atoms must then become more positive. The electrons are lost from the species undergoing oxidation and so electrons appear as products in an oxidation reaction. An oxidation is taking place in the reaction $Fe^{2+}(aq) \rightarrow Fe^{3+}(aq) + e^-$ because electrons are lost from the species being oxidized, $Fe^{2+}(aq)$, despite the apparent production of electrons as "free" entities in oxidation reactions. Conversely the term reduction refers to the gain of one or more electrons by an element, compound, or chemical substituent/subunit.

An "oxidation state" refers to the electrically neutral state or to the state produced by the gain or loss of electrons to an element, compound, or chemical substituent/subunit. In a preferred embodiment, the term "oxidation state" refers to states including the neutral state and any state other than a neutral state caused by the gain or loss of electrons (reduction or oxidation).

The term "multiple oxidation states" means more than one oxidation state. In preferred embodiments, the oxidation states may reflect the gain of electrons (reduction) or the loss of electrons (oxidation).

The terms "different and distinguishable" when referring to two or more oxidation states means that the net charge on the entity (atom, molecule, aggregate, subunit, etc.) can exist in two different states. The states are said to be "distinguishable" when the difference between the states is greater than thermal energy at room temperature (e.g. 0° C. to about 40° C.).

The terms "redox-active molecule", "redox-active unit" or "redox-active subunit" refers to a molecule or component of a molecule that is capable of being oxidized or reduced by the application of a suitable voltage.

The term "subunit", as used herein, refers to a redox-active component of a molecule.

The terms "storage molecule" or "memory molecule" refer to a molecule having one or more oxidation states (i.e., a redox-active molecule) that can be used for the storage of information (e.g. a molecule comprising one or more redox-active subunits). In certain embodiments redox-active molecules for use in this invention have at least two, preferably at least 3, more preferably at least 4, 8, or 16, or more different and distinguishable non-neutral oxidation states.

The term "storage medium" refers to a composition comprising two or more storage molecules (redox-active molecules). The storage medium can contain only one species of storage molecule or it can contain two or more different species of storage molecule. In certain embodiments the storage media comprise a multiplicity (at least 2) of different and distinguishable (preferably non-neutral) oxidation states. The multiplicity of different and distinguishable oxidation states can be produced by the combination of different species of storage molecules, each species contributing to said multiplicity of different oxidation states and each species having a single non-neutral oxidation state. Alternatively or in addition, the storage medium can comprise one or more species of storage molecule having a multiplicity of non-neutral oxidation states. The storage medium can contain predominantly one species of storage molecule or it can contain a number of different storage molecules. The storage media can also include molecules other than storage molecules (e.g. to provide chemical stability, to provide suitable mechanical properties, to prevent charge leakage, etc.).

The term "electrochemical cell" consists minimally of a reference electrode, a working electrode, a redox-active medium (e.g. a storage medium), and, if necessary, some means (e.g., a dielectric) for providing electrical conductivity between the electrodes and/or between the electrodes and the medium. In some embodiments, the dielectric is a component of the storage medium.

The terms "memory element", "memory cell", or "storage cell" refer to an electrochemical cell that can be used for the storage of information. Preferred "storage cells" are discrete regions of storage medium addressed by at least one and preferably by two electrodes (e.g. a working electrode and a reference electrode). The storage cells can be individually addressed (e.g. a unique electrode is associated with each memory element) or, particularly where the oxidation states of different memory elements are distinguishable, multiple memory elements can be addressed by a single electrode. The memory element can optionally include a dielectric (e.g. a dielectric impregnated with counterions).

The term "storage location" refers to a discrete domain or area in which a storage medium is disposed. When addressed with one or more electrodes, the storage location may form a storage cell. However if two storage locations contain the same storage media so that they have essentially the same oxidation states, and both storage locations are commonly addressed, they may form one functional storage cell.

Addressing a particular element refers to associating (e.g., electrically coupling) that memory element with an electrode such that the electrode can be used to specifically set and/or determine the oxidation state(s) of that memory element.

The term "storage density" refers to the number of bits per volume and/or bits per molecule that can be stored. When the storage medium is said to have a storage density greater than one bit per molecule, this refers to the fact that a storage medium preferably comprises molecules wherein a single molecule is capable of storing at least one bit of information.

The terms "read" or "interrogate" refer to the determination of the oxidation state(s) of one or more molecules (e.g. molecules comprising a storage medium).

The term "refresh" when used in reference to a storage molecule or to a storage medium refers to the application of a voltage to the storage molecule or storage medium to re-set the oxidation state of that storage molecule or storage medium to a predetermined state (e.g. an oxidation state the storage molecule or storage medium was in immediately prior to a read).

The term "$E_{1/2}$" refers to the practical definition of the formal potential (E°) of a redox process as defined by $E = E° + (RT/nF)\ln(D_{ox}/D_{red})$ where R is the gas constant, T is temperature in K (Kelvin), n is the number of electrons involved in the process, F is the Faraday constant (96,485 Coulomb/mole), $D_{ox}$ is the diffusion coefficient of the oxidized species and $D_{red}$ is the diffusion coefficient of the reduced species.

A voltage source is any source (e.g. molecule, device, circuit, etc.) capable of applying a voltage to a target (e.g. an electrode).

The term "present on a single plane", when used in reference to a memory device of this invention refers to the fact that the component(s) (e.g. storage medium, electrode(s), etc.) in question are present on the same physical plane in the device (e.g. are present on a single lamina). Components that are on the same plane can typically be fabricated at the same time, e.g., in a single operation. Thus, for example, all of the electrodes on a single plane can typically be applied in a single (e.g., sputtering) step (assuming they are all of the same material).

"Light harvesting rods" as described herein can be essentially the same as described in U.S. Pat. Nos. 6,407,330 or 6,420,648, or they can be fully or partially cross-linked (see, e.g., U.S. Patent Publication 20040244831 A1). Such light harvesting rods, whether or not crosslinked, are in certain embodiments, non-discotic backbone polymers.

A substrate as used herein is preferably a solid material (which may be flexible or rigid) suitable for the attachment of one or more molecules. Substrates can be formed of materials including, but not limited to glass, organic polymers, plastic, silicon, minerals (e.g. quartz), semiconducting materials, ceramics, metals, etc. The substrate can be in any suitable shape, including flat, planar, curved, rod-shaped, etc. The substrate can be inherently conductive or semiconductive and can serve itself as an electrode, or an electrode can be formed on or connected to the substrate by any suitable means (e.g., by deposition of a metal (e.g., gold layer), a conductive oxide layer, etc.). When present in solar cells either or both substrates can be transparent (that is, wavelengths of light that excite the chromophores can pass through the substrate and corresponding electrode, even if they are visually opaque). In light-harvesting arrays, the substrate and electrode can be of any suitable type. One of the substrates can be opaque with respect to the wavelengths of light that excite the chromophores. One of the substrates can be reflective or provided with a reflective coating so that light that passes through the arrays or rods is reflected back to the arrays or rods.

The term "electrode" refers to any medium capable of transporting charge (e.g. electrons) to and/or from a particular moiety (e.g., a light harvesting rod, a redox-active molecule, etc.). In certain embodiments preferred electrodes are metals (e.g., gold, aluminum), non-metals (e.g., conductive oxides, carbides, sulfide, selinides, tellurides, phosphides, and arsenides such as cadmium sulfide, cadmium telluride, tungsten diselenide, gallium arsenide, gallium phosphide, etc.), and conductive organic molecules. The electrodes can be manufactured to virtually any 2-dimensional or 3-dimensional shape.

The term "fixed electrode" is intended to reflect the fact that the electrode is essentially stable and unmovable with respect to the storage medium. That is, the electrode and storage medium are arranged in an essentially fixed geometric relationship with each other. It is of course recognized that the relationship alters somewhat due to expansion and contraction of the medium with thermal changes or due to changes in conformation of the molecules comprising the electrode and/or the storage medium. Nevertheless, the overall spatial arrangement remains essentially invariant. In a preferred embodiment this term is intended to exclude systems in which the electrode is a movable "probe" (e.g. a writing or recording "head", an atomic force microscope (AFM) tip, a scanning tunneling microscope (STM) tip, etc.).

The term "working electrode" is used to refer to one or more electrodes that are used to set or read the state of a storage medium and/or storage molecule (e.g., redox-active molecule).

The term "reference electrode" is used to refer to one or more electrodes that provide a reference (e.g. a particular reference voltage) for measurements recorded from the working electrode. In preferred embodiments, the reference electrodes in a memory device of this invention are at the same potential although in some embodiments this need not be the case.

The term "conductive oxide" refers to any suitable conductive oxide including binary metal oxides such as tin oxide, indium oxide, titanium oxide, copper oxide, and zinc oxide, or ternary metal oxides such as strontium titanate and barium titanate. Other examples of suitable conductive oxides include but are not limited to indium tin oxide, titanium dioxide, tin oxide, gallium indium oxide, zinc oxide, and zinc indium oxide. The metal oxide semiconductors may be intrinsic or doped, with trace amounts of materials, to control conductivity.

The term "heterocyclic ligand" as used herein generally refers to any heterocyclic molecule consisting of carbon atoms containing at least one, and preferably a plurality of, hetero atoms (e.g., N, O, S, Se, Te), which hetero atoms may be the same or different, and which molecule is capable of forming a sandwich coordination compound with another heterocyclic ligand (which may be the same or different) and a metal. In certain embodiments such heterocyclic ligands are typically macrocycles, particularly tetrapyrrole derivatives such as the phthalocyanines, porphyrins, and porphyrazines.

The term "porphyrinic macrocycle" refers to a porphyrin or porphyrin derivative. Such derivatives include porphyrins with extra rings ortho-fused, or orthoperifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, beta.-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Certain preferred porphyrinic macrocycles comprise at least one 5-membered ring.

The term porphyrin refers to a cyclic structure typically composed of four pyrrole rings together with four nitrogen atoms and two replaceable hydrogens for which various metal atoms can readily be substituted. A typical porphyrin is hemin.

A "chlorin" is essentially the same as a porphyrin, but differs from a porphyrin in having one partially saturated pyrrole ring. The basic chromophore of chlorophyll, the green pigment of plant photosynthesis, is a chlorin.

A "bacteriochlorin" is essentially the same as a porphyrin, but differs from a porphyrin in having two partially saturated non-adjacent (i.e., trans) pyrrole rings.

An "isobacteriochlorin" is essentially the same as a porphyrin, but differs from a porphyrin in having two partially saturated adjacent (i.e., cis) pyrrole rings.

The terms "sandwich coordination compound," or "sandwich coordination complex" refer to a compound of the formula $L^n M^{n-1}$, where each L is a heterocyclic ligand such as a porphyrinic macrocycle, each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand (depending upon the oxidation state of the metal). Thus sandwich coordination compounds are typically not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another, see, e.g., Ng and Jiang (1997) *Chem. Soc. Rev.* 26, 433-442). Sandwich coordination compounds can be "homoleptic" (wherein all of the ligands L are the same) or "heteroleptic" (wherein at least one ligand L is different from the other ligands therein).

The term "double-decker sandwich coordination compound" refers to a sandwich coordination compound as described above where n is 2, thus having the formula $L^1$-$M^1$-$L^2$, wherein each of $L^1$ and $L^2$ may be the same or different (see, e.g., Jiang et al., (1999) *J. Porphyrins Phthalocyanines* 3: 322-328). In certain embodiments double-decker sandwich coordination compounds are preferred for use in solar cells because of their photochemical properties.

The term "triple-decker sandwich coordination compound" refers to a sandwich coordination compound as described above where n is 3, thus having the formula $L^1$-$M^1$-$L^2$-$M^2$-$L^3$, wherein each of $L^1$, $L^2$ and $L^3$ may be the same or different, and $M^1$ and $M^2$ may be the same or different (see, e.g., U.S. Pat. No. 6,212,093 B1; Arnold et al. (1999) *Chem. Lett.* 483-484).

The term "multiporphyrin array" refers to a discrete number of two or more covalently-linked porphyrinic macrocycles. The multiporphyrin arrays can be linear, cyclic, or branched, but are preferably linear herein. Light harvesting rods herein are preferably multiporphyrin arrays. The light harvesting rods or multiporphyrin arrays may be linear (that is, all porphyrinic macrocycles may be linked in trains) or may contain one or more bends or "kinks" (for example, by including one or more non-linear linkers in a light-harvesting rod, or by including one or more cis-substituted porphyrinic macrocycles in the light harvesting rod. Some of the porphyrinic macrocycles may further include additional ligands, particularly porphyrinic macrocycles, to form sandwich coordination compounds as described further below. The rods optionally but preferably are oriented substantially perpendicularly to either, and most preferably both, of the first and second electrodes.

A "chromophore" refers to a light-absorbing unit that can be a unit within a molecule or that can comprise the entire molecule. Typically a chromophore is a conjugated system (alternating double and single bonds which can include non-bonded electrons but is not restricted to alternating double and single bonds since triple and single bonds, since mixtures of alternating triple/double and single bonds also constitute chromophores. A double or triple bond alone constitutes a chromophore. Heteroatoms can be included in a chromophore.). Examples of chromophores include the cyclic 18 pi-electron conjugated system that imparts color to porphyrinic pigments, the linear system of alternating double and single bonds in the visual pigment retinal, or the carbonyl group in acetone.

The terms "charge separation group" and "charge separation unit" refer to molecular entities that upon excitation (by direct absorption or energy transfer from another absorber) displace an electron to another part of the same molecule, or transfer an electron to a different molecule, semiconductor, or metal. The "charge separation group" and "charge separation unit" results in storage of some fraction of the excited state energy upon displacement or transfer of an electron. Typically the "charge separation group" and "charge separation unit" is located at the terminus of a light-harvesting array or rod, from which excited-state energy is received. The "charge separation group" and "charge separation unit" facilitates or causes conversion of the excited-state energy into a separate electron and hole or an electron-hole pair. The electron can be injected into the semiconductor by the "charge separation group" or "charge separation unit". It is feasible that the "charge separation group" and "charge separation unit" could extract an electron from a different molecule or semiconductor, thereby creating a negative charge on the "charge separation group" and "charge separation unit" and a hole in the other molecule or semiconductor. The reaction center of bacterial photosynthesis is an example of a "charge separation group" or "charge separation unit". Synthetic porphyrin-quinone or porphyrin-buckyball molecules also function to absorb light and utilize the resulting energy to separate charge.

In certain embodiments, when a metal is designated by "M" or "$M^n$", where n is an integer, it is recognized that the metal can be associated with a counterion.

A linker is a molecule used to couple two different molecules, two subunits of a molecule, or a molecule to a substrate. When all are covalently linked, they form units of a single molecule.

The term "electrically coupled" when used with reference to a light harvesting rod and electrode, or to chromophores, charge separation groups and electrodes, or to a storage molecule (redox-active molecule) and/or storage medium and electrode refers to an association between that group or molecule and the coupled group or electrode such that electrons move from the storage medium/molecule to the electrode or from the electrode to the molecule and thereby alter the oxidation state of the storage molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the light harvesting rod may simply be contacted with the electrode surface. There also need not necessarily be any contact between the electrode and the light harvesting rod where the electrode is sufficiently close to the light harvesting rod, storage molecule, etc., to permit electron tunneling between the medium/molecule and the electrode.

"Excited-state energy" refers to the energy stored in the chromophore in a metastable state following absorption of light (or transfer of energy from an absorber). For an excited singlet (triplet) state, the magnitude of the "excited-state energy" is estimated by the energy of the shortest wavelength fluorescence (phosphorescence) band. The magnitude of the "excited-state energy" is typically greater than or equal to the energy of the separated electron and hole following charge separation.

Electrolytes used in certain embodiments of the present invention can be aqueous or non-aqueous electrolytes, including, but not limited to, polymer electrolytes. The electrolyte may comprise or consist of a solid, in which latter case the device can be produced devoid of liquid. In various embodiments the electrolyte typically consists of or comprises a substance that increases the electrical conductivity of a carrier medium. Most electrolytes are salts or ionic compounds. Examples include sodium chloride (table salt), lithium iodide, or potassium bromide in water; tetrabutylammonium hexafluorophosphate or tetraethylammonium perchlorate in acetonitrile or dichloromethane; or an ionic polymer in a gel.

The term "mobile charge carriers" refers to an ion, molecule, or other species capable of translating charges (electrons or holes) between the two electrodes in a solar cell and/or to or from electrodes in, for example, a molecular memory or other circuit element. Examples include quinones in water, molten salts, and iodide in a polymer gel such as polyacrylonitrile. Examples of mobile charge carriers include, but are not limited to, iodide, bromide, tetramethyl-1,4-phenylenediamine, tetraphenyl-1,4-phenylenediamine, p-benzoquinone, $C_{60}$, $C_{70}$, pentacene, tetrathiafulvalene, and methyl viologen.

"Cross-linking" as described herein may be full or partial, and for example in some embodiments starts at the second or third porphyrinic macrocycle, but not the first, of the polymer. Cross linking may be by any suitable bond, including both covalent bonds and coordinative bonds.

BRIEF DESCRIPTION OF THE DRAWINGS

FIG. 1A illustrates a generic stepwise synthesis scheme. FIG. 1B illustrates synthesis of a light harvesting moiety (e.g., solar cell element), information storage component, etc. $M^1$, $M^2$, $M^3$, $M^4$, and/or $M^5$ can be the same or different.

FIG. 5 illustrates the stepwise synthesis of the light-harvesting rod in a molecular-based solar cell. A similar approach can be used to synthesize a storage cell, memory element, and the like.

FIGS. 6A and 6B illustrate charge separation units with surface attachment groups and an optionally protected functional group for elaboration of a light harvesting rod. The same or similar units can be used in a storage cell, memory element, and the like.

DETAILED DESCRIPTION

Figure 1A:
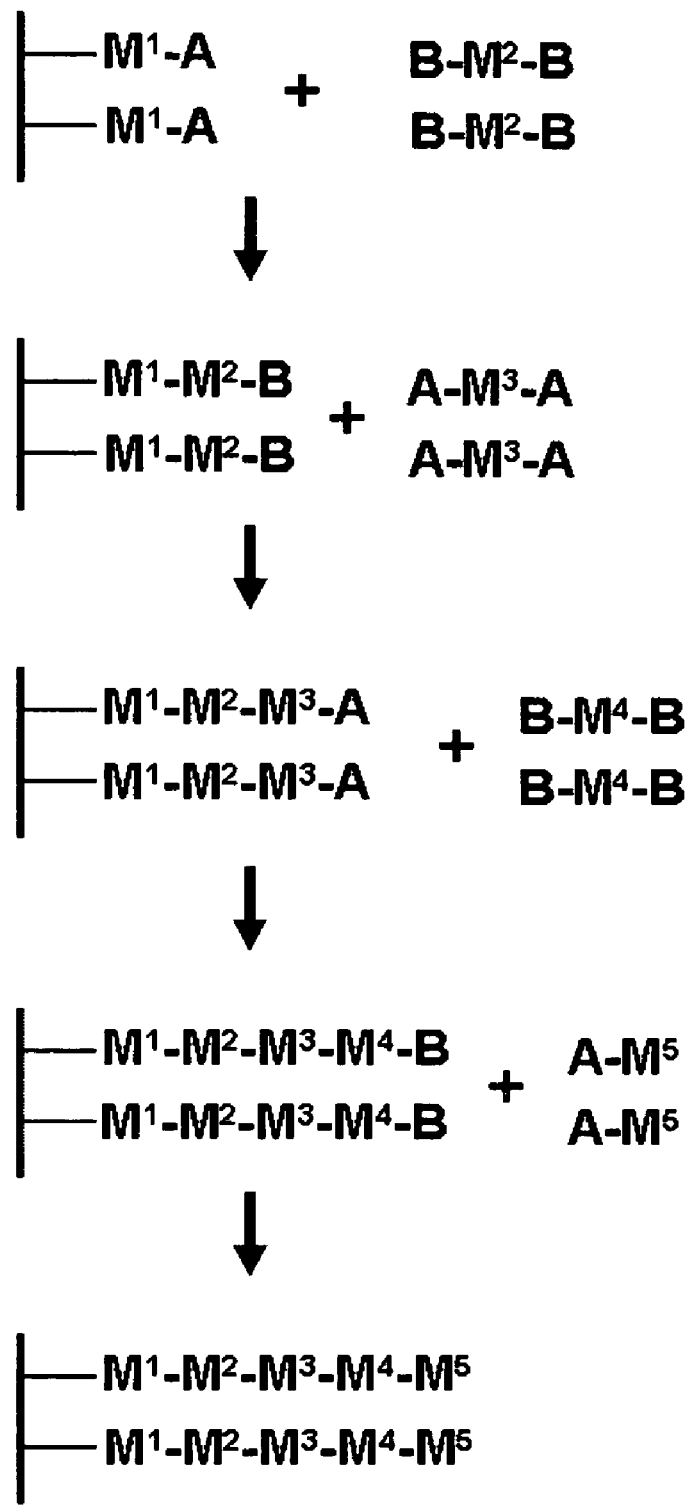
FIGS. 1A and 1B schematically illustrates the stepwise synthesis of an oligomeric molecule attached to a substrate.

This invention provides a novel approach to the stepwise synthesis of oligomeric molecules that eliminates the use of protecting groups. The stepwise synthesis typically proceeds with the stepwise elongation/polymerization of oligomeric molecules attached to an underlying substrate. Unlike previous stepwise synthesis procedures, the methods described herein eliminate the requirement for protecting groups and thus greatly simplify the synthesis by eliminating the requirement of deprotection step between each (monomer) coupling reaction. This reduces the synthesis cost and avoids the necessity of identifying deprotection conditions compatible with the oligomer and/or underlying substrate. In addition, it is believed this improves the step yield thereby substantially increasing the surface density of the full-length oligomers thus produced.

It is noted that while the following discussion pertain to the stepwise addition of monomers to produce an oligomer, it will be appreciated that the same approach can be used to couple pre-fabricated oligomers into an even longer polymer.

The stepwise synthesis methods described herein can be used to join monomers to form an oligomer or to join certain oligomers to form a larger polymer. The monomers can be essentially any monomer(s) that it is desired to couple to form an oligomer. In certain embodiments, however, it is preferred that the monomers or oligomers being coupled be relatively rigid to reduce site-to-site reactivity.

In certain embodiments described herein the stepwise synthesis methods are used to synthesize oligomers/polymers for use in light harvesting arrays (e.g., in solar cells) and/or in molecular memory elements. It will be appreciated that using the teachings provided herein, the stepwise synthesis methods need not be limited to these applications but can be used wherever it is desired to perform a stepwise assembly of particular monomers or oligomers.

I. Stepwise Synthesis Methods.

In the course of studies aimed at stepwise fabrication of molecular information storage devices and light-harvesting devices, we made a surprising finding that enables exceptionally facile fabrication of multad assemblies. The chief finding is that multads of porphyrinic macrocycles (and/or spacers, or various other compositions) can be assembled in a stepwise manner without use of protecting groups. This novel finding enables rapid and controlled assembly in a stepwise manner in an extremely efficient manner.

Consider the synthesis of a multad comprised of several monomers (e.g., charge-storage entities such as porphyrinic macrocycles) in a more or less vertical arrangement on a surface, which is of interest for example, for high density charge storage. One approach is to synthesize the corresponding multad (i.e., array) in solution, then attach the multad to the surface. Alternatively, an in situ assembly can be performed. As noted above, such an assembly process has heretofore required the use of protecting groups. The monomeric building blocks must be prepared with at least one protecting group, and after each coupling reaction, the protecting group must be removed. Thus, one cycle of coupling requires three reactions: protecting group introduction, coupling, and protecting group removal. A further limitation stems from the difficulty, in many instances, of identifying suitable conditions for protecting group removal that are compatible with the protected molecules, the components in the molecular architecture under assembly, and the underlying substrate.

The stepwise synthesis of the present invention employs difunctional monomers wherein the two reactive end groups on a given monomer are identical with each other. By employing two types of monomers, for example $A-M^1-A$ and $B-M^2-B$ (see, e.g., FIG. 1), the coupling can be done to generate oligomers composed of $-M^1-M^2-\ldots M^n$-without use of protecting groups.

In certain embodiments typical A and B functional groups comprise amine and anhydride functional groups. The success of this method stems from (1) growth on a surface, which effectively blocks one site of reactivity on the initial monomer, and (2) the use of relatively rigid monomers wherein site-to-site reactivity is effectively suppressed.

The latter point requires elaboration. Consider a solid-supported synthesis wherein a diamine and a dianhydride are to be elaborated to give a polyimide product. In the case of either monomer having considerable conformational flexibility, inter-site reactivity is expected, and in practice, is a chief source of byproduct formation. Such inter-site reaction terminates oligomer growth at both sites. In the products of interest for information storage applications (and solar cells), the monomers are conformationally rigid and such inter-site reactions are greatly suppressed.

A wide variety of functional groups (A, B) can be employed. Examples are listed in Table 1 below, but this list is intended to be illustrative and not limiting. In preferred embodiments, A and B are complementary and not identical to each other in a reaction.

Note that the monomer M can comprise a charge-storage entity (as desired for molecular information storage, or use as a battery), a charge-separation unit (as desired for a solar cell), a spacer (conductive, semiconductive, or insulating), an electrolyte, a tether for surface attachment, and so forth. The charge-storage entities include, but are not limited to porphyrinic macrocycles (including hydroporphyrins such as chlorins and bacteriochlorins) and complexes thereof. The monomers employed in a resulting oligomer or "stack" can be identical to each other or different.

Figure 1B:
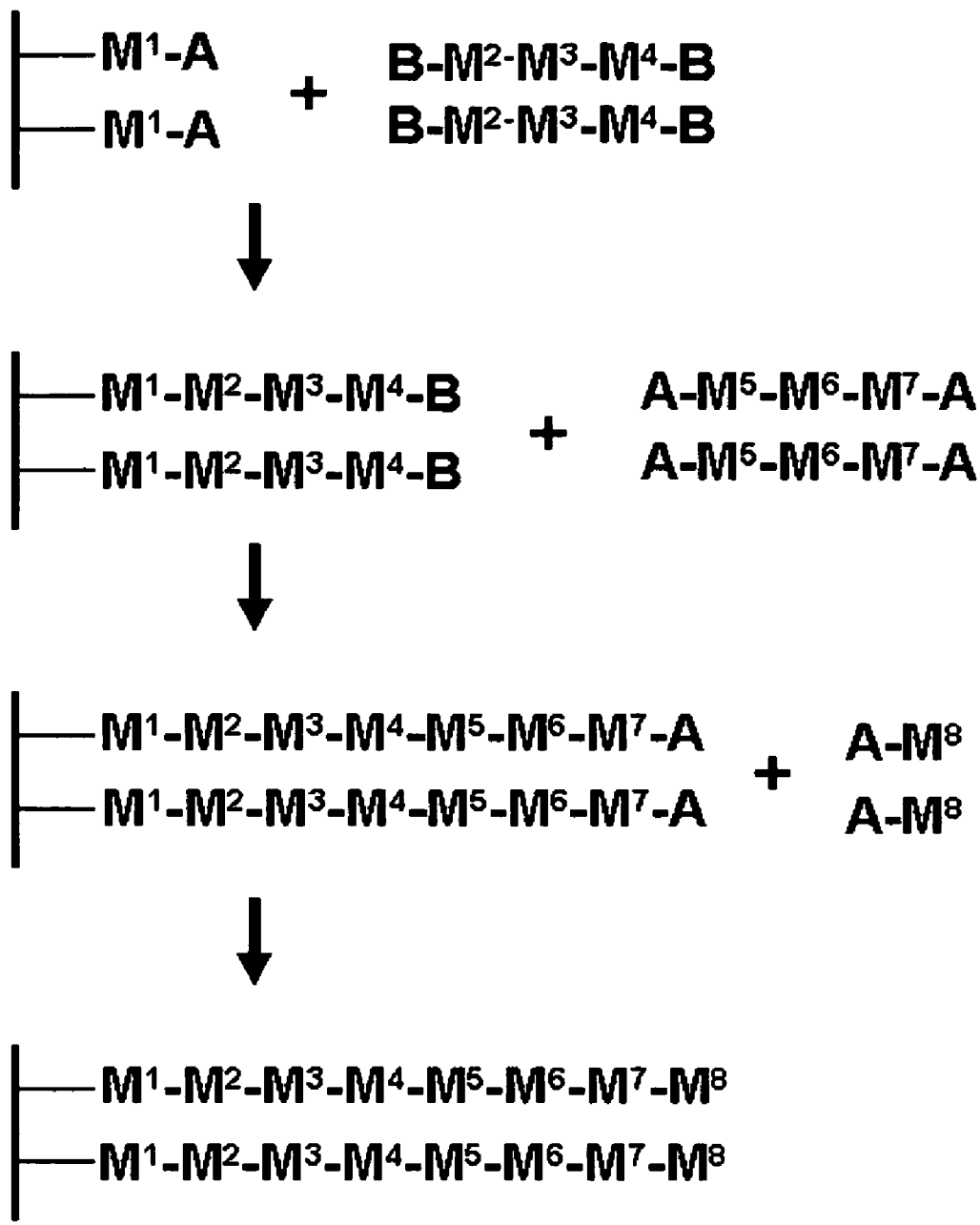

In certain embodiments the monomers can themselves be oligomers of the same or different monomers which can then be polymerized according to this method to form polymers (see, e.g., FIG. 1B). In certain preferred embodiments, where the monomers are themselves oligomers, the oligomers are selected to be conformationally rigid to suppress inter-site reactions.

One particularly preferred system consists of a porphyrinic charge storage molecule bearing amines in a trans-configuration (e.g., 4-aminophenyl groups at the 5- and 15-positions of the porphyrin) and 4,4'-biphenyldiisocyanate.

TABLE 1

Reactive groups and product linkages in attachment strategies.

| Reactive group (A) | Reactive group (B) | Product Linkage |
| --- | --- | --- |
| aldehyde | acyl hydrazide | acyl hydrazone |
| aldehyde | amine | imine |
| salicylaldehyde | amine | salicylaldimine |
| salicylaldehyde | acyl hydrazide | H-bonded acyl hydrazone |
| aldehyde | cyanomethyl | vinyl |
| aldehyde | carboxymethyl | vinyl |
| isocyanate | amine | urea |
| isocyanate | alcohol/phenol | carbamate |
| anhydride | amine | carboxy amide |
| anhydride | amine | imide |
| isothiocyanate | amine | thiourea |
| isothiocyanate | alcohol/phenol | thiocarbamate |
| 2-iminothiolane | amine | amide-alkyl-thiol |
| benzyl halide | phenol or alcohol | ether |
| pentafluorophenyl | phenol or alcohol | ether |
| phenacyl bromide | phenol or alcohol | phenacyl ether |
| α-haloacetamide | alcohol | α-ether-acetamide |
| α-haloacetamide | carboxylic acid | α-ester-acetamide |
| thioester/active ester | amine | amide |
| sulfonyl chloride | amine | sulfonamide |
| boronic acid | diol | alkyl boronate |
| acrylate | thiol | thioether |
| aldehyde | diol | acetal |
| epoxide | amine | hydroxyalkylamine |

II. Molecular Memory—Arrays of Electrodes Electrically Coupled to Redox-active Oligomeric Molecules.

The methods of this invention are well suited to the preparation of molecular memory elements comprising oligomeric redox-active molecules. As indicated, the use of oligomeric redox-active molecules attached to a substrate can improve the charge storage density and hence the readability of the molecular memory. Thus, in certain embodiments, this invention contemplates the fabrication of memory devices using the stepwise synthesis methods described herein. In various embodiments the surface on which the oligomer is synthesized can be the surface of an electrode and/or a counterelectrode.

The electrode and/or counter electrodes are typically fabricated of materials capable of conducting electrons. The electrodes and/or counterelectrodes can comprise conductors, semiconductors, superconductors, and the like. In certain embodiments, the electrodes and/or counterelectrodes have a resistivity of less than about $10^{-2}$ ohm-meters, preferably less than about $10^{-3}$ ohm-meters, more preferably less than about $10^{-4}$ ohm-meters, and most preferably less than about $10^{-5}$, or $10^{-6}$ ohm-meters.

Certain preferred electrodes and/or counterelectrodes include metals and/or metal oxides (e.g., Au, Sn, Si). In certain embodiments particularly preferred electrodes comprise a material such as ruthenium, osmium, cobalt, rhodium, rubidium, lithium, sodium, potassium, vanadium, cesium, beryllium, magnesium, calcium, chromium, molybdenum, silicon, germanium, aluminum, iridium, nickel, palladium, platinum, iron, copper, titanium, tungsten, silver, gold, zinc, cadmium, indium tin oxide, carbon, a carbon nanotube, and the like.

Suitable semiconductors include, but are not limited to Si, Ge, Sn, Se, Te, B, diamond, P, B—C, B—P($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$, and/or an appropriate combination of two or more such semiconductors. The semiconductors can optionally include one or more dopants (e.g. including, but not limited to a p-type dopant from Groups II, III, or IV of the periodic table; an n-type dopant from Group V of the periodic table).

The redox-active oligomeric molecules are typically electrically coupled to one or more electrodes to permit setting and/or reading of the oxidation state of the oligomer(s).

Thus, in certain embodiments, this invention contemplates a composition comprising an array of electrodes where a plurality of the electrodes each comprise a redox-active molecule attached to the electrode using stepwise synthesis methods described herein. In various embodiments the redox-active molecules are disposed in the array at various discrete locations to form thereby an electrochemical "storage" cell/memory element. In certain embodiments the array comprises at least $10^3$, preferably at least $10^4$, more preferably at least $10^5$, and most preferably at least $10^7$, $10^8$, or $10^9$ such storage cells.

In various embodiments each storage cell/location is addressed by at least one electrode, and more preferably by at least two electrodes (e.g., a working electrode and a counter electrode). In various embodiments the working electrode and/or counter electrode can be common to a plurality of storage locations, but the combination of electrodes are preferentially disposed to provide independent setting and/or reading of the oxidation states of a plurality of storage locations.

Architectures of various arrays of redox-active moieties are described in Roth et al. (2000) *J. Vac. Sci. Technol. B*, 18: 2359-2364; Liu et al. (2003) *Science*, 302: 1543-1545; U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, and the like.

III. Fabrication and Characterization of the Storage Device

Molecular memory comprising oligomeric molecules synthesized on a surface by the methods described can be further fabricated using standard methods well known to those of skill in the art. Typically such fabrication methods utilize typical solid state fabrication technologies coupled with the stepwise synthesis methods described herein.

In certain preferred embodiments, electrode layer(s) are applied to a suitable substrate (e.g. silica, glass, plastic, ceramic, semiconductor, etc.) according to standard well known methods (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*). In addition, examples of the use of micromachining techniques on silicon or borosilicate glass chips can be found in U.S. Pat. Nos. 5,194,133, 5,132,012, 4,908,112, and 4,891,120.

In one embodiment a metal layer is beam sputtered onto the substrate (e.g., a 10 nm thick chromium adhesion layer is sputtered down followed by a 200 nm thick layer of gold). Then maskless laser ablation lithography (see below), performed e.g., with a Nd:YAG laser, is used to create features with micron dimensions, or with an excimer laser to create features of nanometer dimensions) will create an array of parallel lines of conductor (e.g., gold), that can be used as working electrodes with dimensions ranging between a few microns to tens of nanometers.

Once the electrode array is formed, the entire array, or portions of the array, or individual electrodes are wetted (e.g. immersed or spotted) with one or more solutions of the appropriate chemical compounds described herein to effect a stepwise synthesis. In certain embodiments, the initial coupling of a linker and/or first monomer can be accomplished by heating, e.g. as described in Example 1, and in U.S. Patent Publication 2005-0019500, PCT Publication WO 2005/043,583, and in U.S. Ser. Nos. 10/742,596, and 11/140,011. Patterning of the initial linker and/or monomer (e.g. using masks and/or spotting technologies) can determine the site(s) of subsequent stepwise synthesis.

The stepwise synthesis methods are then performed, e.g., as described herein, to effectively elongate the attached oligomer. Effective washing between coupling steps removes unlinked monomers.

It will be appreciated that different solutions can be applied to different regions of the electrode array to produce storage cells comprising different storage medium. Methods of spotting different reagents on surfaces (e.g. on glass surfaces) at densities up to tens of thousands of different species/spots per $cm^2$ are known (see, e.g., U.S. Pat. No. 5,807,522).

If desired, a suitable electrolyte layer (e.g. a thin layer of Nafion polymer) approximately 1 nm to 1000 nm, preferably about 100 nm to about 500 nm, more preferably about 10 nm to about 100 nm and most preferably about one hundred nanometers thick can be cast over portions or the entire surface of the chip. This polymer serves to hold the electrolyte for electrochemical reaction. Finally, the entire chip can be coated with a layer (e.g., 10 nm to about 1000 nm, more preferably 100 nm to about 300 nm and most preferably about 200 nm) of conducting material (e.g., silver) which acts as a reference electrode.

In certain approaches, the chip is then turned 90 degrees, and maskless laser ablation lithography can be performed again to create a second array of parallel lines that are perpendicular to the original set. This forms a three dimensional array of individual memory elements, where each element is formed by the intersection of these two perpendicular linear arrays.

Each individual element can be addressed by selecting the appropriate X and Y logic elements, corresponding to one working electrode and one reference electrode separated by the Nafion polymer/electrolyte layer. Since this structure is inherently three dimensional, it is possible, particularly using the polypodal tethers described herein to extend the array into the Z-direction, creating a 3-D array of memory elements as large as it is feasible to connect to.

These structures can be created on the micrometer or nanometer scale. It is possible to create these structures on a scale similar to silicon microstructures created with conventional nanolithographic techniques (i.e. 100-200 nm). This allows the interfacing of the memory elements with conventional silicon-based semiconductor electronics.

In the laser-ablation lithography, coherent light is sent through a beam splitter (50% transmittance) and reflected by a mirror to make two nearly parallel identical beams (Rosenwald et al. (1998) *Anal. Chem.*, 70: 1133-1140). These beams are sent through e.g., a 50 cm focal length lens for ease in focusing to a common point. The placement of the beams is fine-tuned to allow complete overlap of the mode structure of the laser spot. Higher order interference patterns are minimized through the use of high quality optics ($1/10$ wave surface flatness). This ensures that the variation between intensity maxima and minima in the first order will be several orders of magnitude larger than those formed with second and higher orders. This produces a well-defined pattern of lines across the electrode surface, where the spacing between points of positive interference (D) can be approximated by the Bragg Equation: $n\lambda=2D \sin(\theta/2)$, where $\lambda$=wavelength, $\theta$=angle between the beams, and n is order. For example, when a Nd:YAG is used at 1064 nm, the recombination of the two beams in this manner generates an interference pattern with ~2 micron spacing when the angle between the 2 beams is 15°. The interference pattern spacing can easily be changed by modifying the angle between the beams. Attenuation of the beam was accomplished by inserting one or more neutral density filters before the beam splitter. In this way, the exposure of the gold layer to the Nd-YAG interference pattern can be performed at different beam attenuations to produce power densities between 1 and 100 $MW/cm^2$.

In certain embodiments, the memory elements comprising the memory devices of this invention are fabricated using "moleholes". In certain embodiments, a "molehole" comprises a two or more arrays of conductors or semiconductors (e.g. electrodes) separated from each other vertically (e.g. by a dielectric, insulator, etc.) so that the conductors overlap each other at least one point. Within one or more intersecting points of an upper and lower electrode (e.g. top and bottom interconnect) a well is fabricated. This well penetrates the electrodes, so that the electrodes form a portion of the side and/or bottom of the well.

Storage molecules of this invention are attached to one or more of the exposed conductor surfaces in the wells. Each well can then function as an electrochemical cell permitting electrochemical measurements of the bound molecules. The fabrication and use of such "moleholes" is described in detail in copending application U.S. Ser. No. 10/046,499, filed on Oct. 26, 2001.

Addressing of the storage cell(s) in the devices of this invention is relatively straightforward. In one simple approach a discrete pair of electrodes (e.g., one working and one reference electrode) can be provided effectively connecting to every storage cell. Individual reference electrodes, however are not required and can be replaced with one or more common reference electrodes connected to all or to a subset of all of the storage elements in a particular device. Alternatively, the common reference electrodes can be replaced with one or more conductive "backplanes" each communicating to all, or to a subset, of the storage cells in a particular device.

Where the storage cells contain identical storage media, in certain embodiments, each storage cell is addressed with a separate working electrode so that the storage (oxidation) states of the storage cells can be distinguished from each other. Where the storage cells contain different storage media such that the oxidation states of one storage cell are different and distinguishable from the oxidation states of another storage cell, the storage cells can be addressed by a common working electrode thereby reducing the number of electrodes in a device.

In certain embodiments, the storage devices of this invention contain at least 2048, 4096, 8192, 16384, 32768, 65,536, 131,072, 262,144, 5,24,288, 106, $10^7$, $10^8$, or $10^9$, or more storage locations per layer (2048, 4096, 8192, 16384, 32768, 65,536, 131,072, 262,144, 5,24,288, 106, $10^7$, $10^8$, or $10^9$ or more locations in the mirror image architecture) with each location capable of storing one or more bits (e.g., holding a two bit word). In certain embodiments, a 1024-bit or a 512-bit chip can contain 8 wiring interconnects on each of the three electrode grids in the 3-dimensional architecture.

The performance (e.g. operating characteristics) of the memory devices of this invention is characterized by any of a wide variety of methods, most preferably by electrochemical methods (anperometry and sinusoidal voltammetry, see, e.g., Howell et al. (1986) *Electroanal. Chem.*, 209: 77-90; Singhal and Kuhr (1997) *Anal. Chem.*, 69: 1662-1668), optical spectroscopy (Schick et al. (1989) *J. Am. Chem. Soc.* 111: 1344-1350), atomic force microscopy, electron microscopy and imaging spectroscopic methods. Surface-enhanced resonance and Raman spectroscopy are also used to examine the storage medium on the electrodes.

Among other parameters, characterization of the memory devices (e.g., memory cells) involves determining the number of storage medium molecules (e.g., porphyrin arrays) required for defect-tolerant operation. Defect tolerance includes factors such as reliably depositing the required number of holes to write the desired digit and accurately detecting the numbers/transfer rates of the holes.

The long-term resistance of electron/holes to charge-recombination in the solid-phase medium of the device package is also determined. Using these parameters, the device architecture can be optimized for commercial fabrication.

Molecular memories prepared according to the methods can be written to and read according to the methods described in U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, and the like.

IV. Light Harvesting Arrays.

Figure 5:
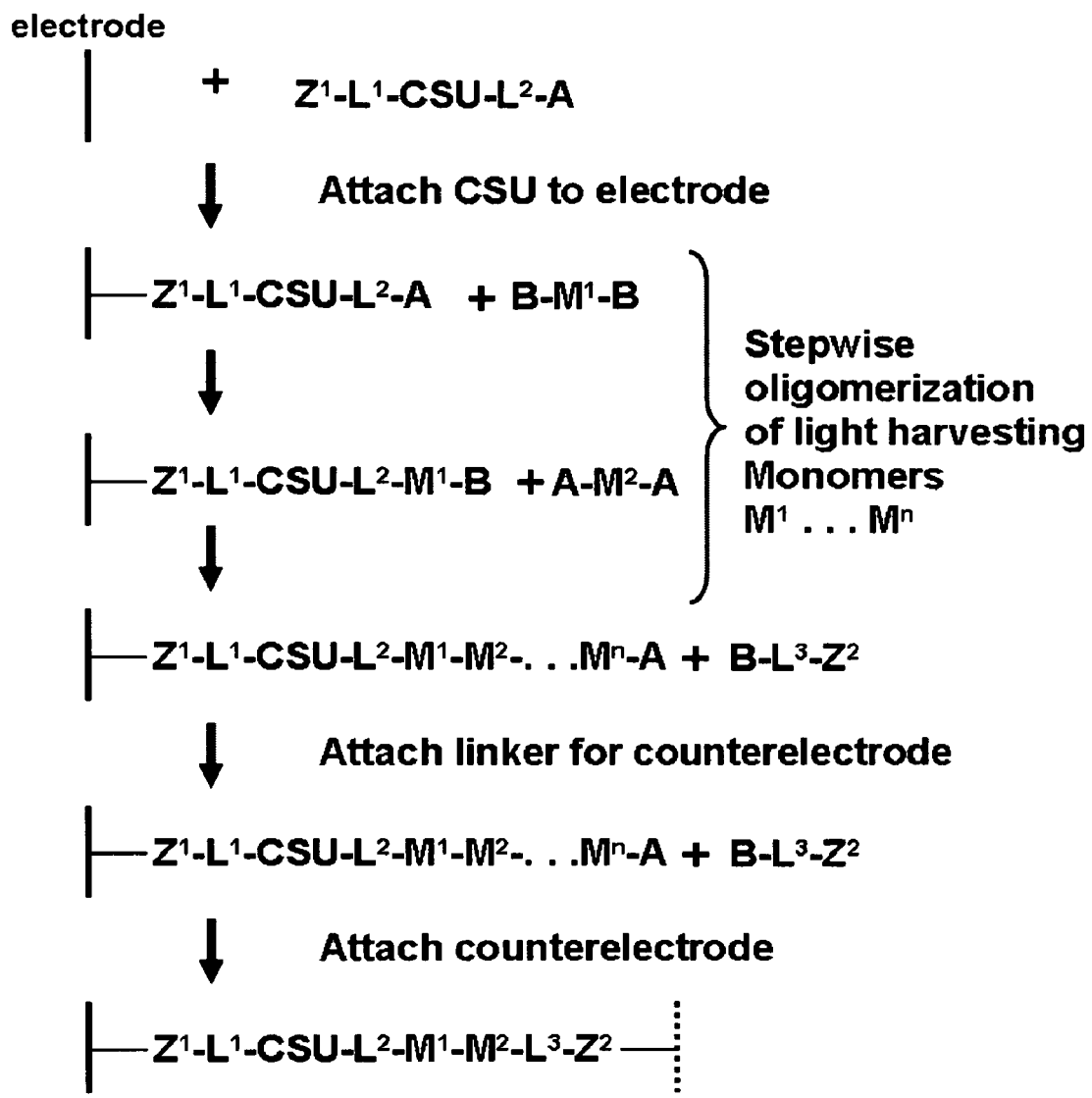

In certain embodiments the methods of this invention can be utilized in the fabrication of molecular based light harvesting arrays as described, for example, in U.S. Patent Publication 2004/0244831 A1. In one embodiment, illustrated in FIG. 5, a charge-separation unit (CSU) is attached to the surface of the electrode via attachment group $Z^1$ and linker $L^1$. A reactive group (A) on the charge-separation group (distal to the electrode) can be present, and, if protected can be unveiled by removal of a protecting group.

Light harvesting monomers ($M^1 \ldots M''$) are assembled using the stepwise synthesis procedure described herein starting with the reactive functional group A attached to the CSU, thereby creating a light-harvesting rod comprising of n monomers. In certain embodiments, a linker can be coupled to the substrate and the CSU can also be built using the stepwise synthesis methods described herein.

The monomers can be the same or different in order to facilitate rectification of migration of excited-state energy and ground-state holes. Upon completing the synthesis of the light-harvesting rod, a unit for attachment to the counterelectrode ($B-L^3-Z^2$) can be introduced followed by attachment/deposition of the counterelectrode (see, e.g., FIG. 5).

Figure 2:
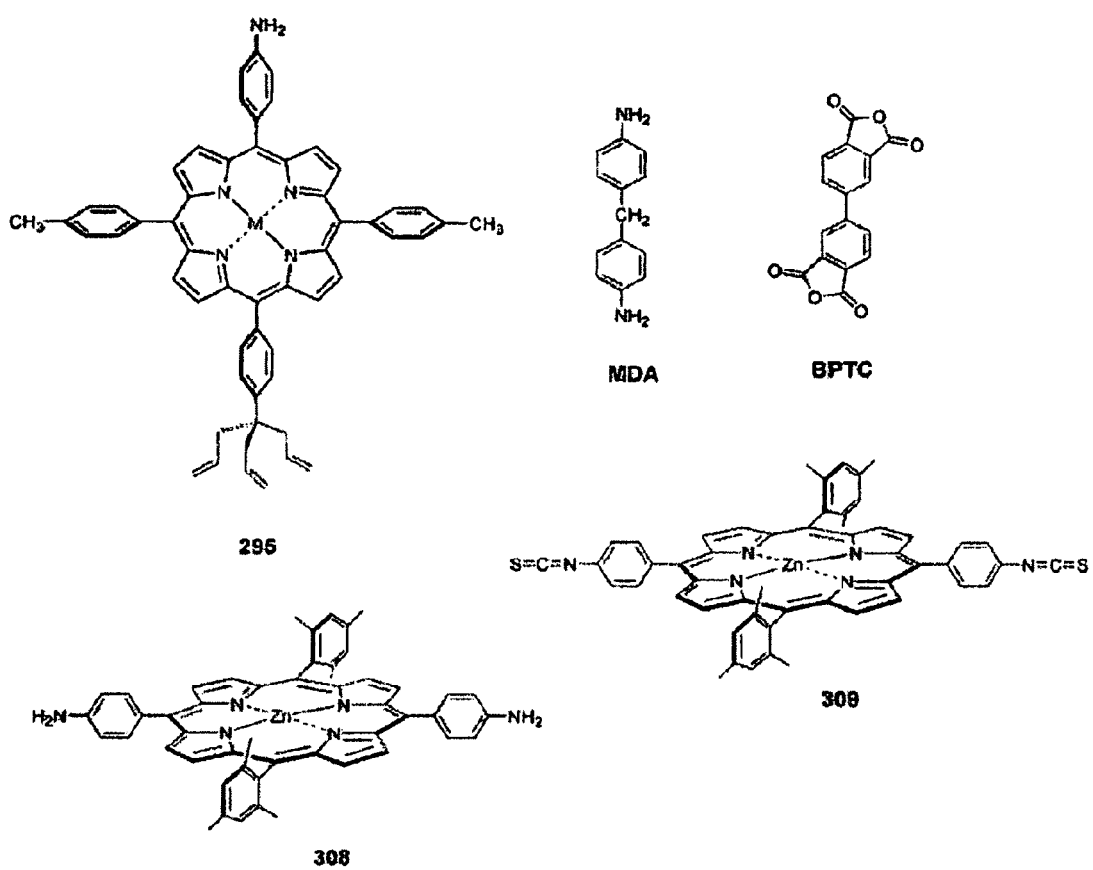
FIG. 2 illustrates the structure of a porphyrin containing an allyl tripod and an opposite 4-aminophenyl group (295), BPTC, MDA.

The monomers can optionally comprise groups on the non-linking positions that can be unveiled for cross-linking. The cross-linking groups, if present, can be reacted after each coupling cycle and/or after the synthesis of the oligomer is completed. Advantages of cross-linking include (i) increased mechanical stability, (ii) controlled porosity of the film, and (iii) opportunity to incorporate an accessory pigment in the cross-linking motif as desired for solar applications.

Where it is desired to cross-link the monomers any of a number of strategies known to those of skill in the art can be employed (see, e.g., FIG. 2 in U.S. Patent Publication U.S. 2004/0244831 A1). Certain preferred groups for linking purposes include, but are not limited to, amine+isothiocyanate; acid hydrazide+formyl, and the like.

This approach is not restricted to application with porphyrinic macrocycles, though, in certain embodiments, such compounds are preferred. Certain suitable porphyrinic macrocycles include, but are not limited to, porphyrins, chlorins, bacteriochlorins, isobacteriochlorins, oxochlorins, dioxobacteriochlorins, dioxoisobacteriochlorins, pyrophorbines, bacteriopyrophorbines, phthalocyanines, naphthalocyanines, tetraazaporphyrins, core modified porphyrinic derivatives, porphyrazines, benzazoloporphyrazines, expanded or contracted porphyrinic derivatives, and the like.

Porphyrins bearing carboxaldehyde groups are well known to those of skill in the art. Thus, for example, chlorophyll b bears one formyl group. Porphyrinic species bearing isothiocyanates are also well known.

Figure 6A:
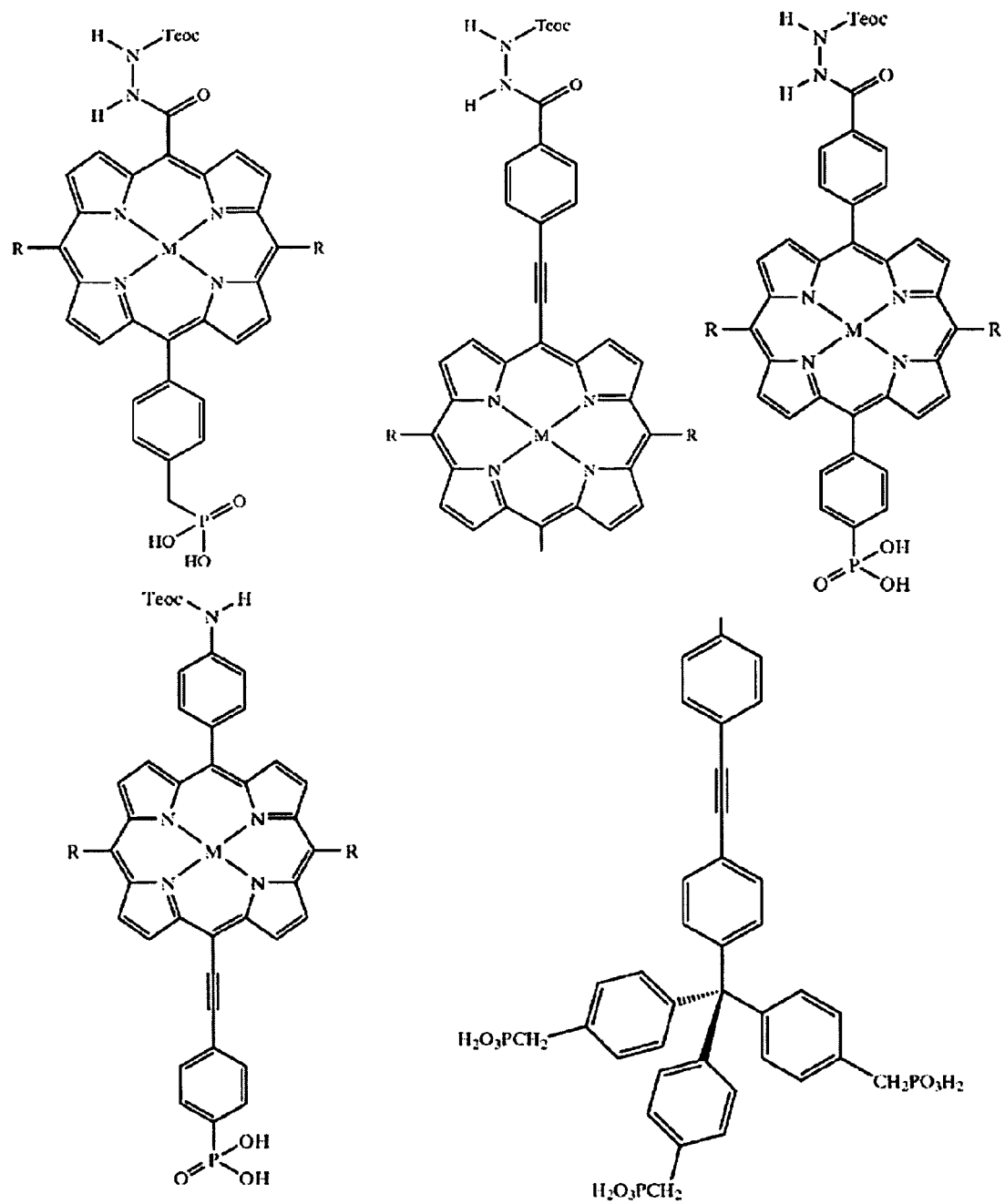
Figure 6B:
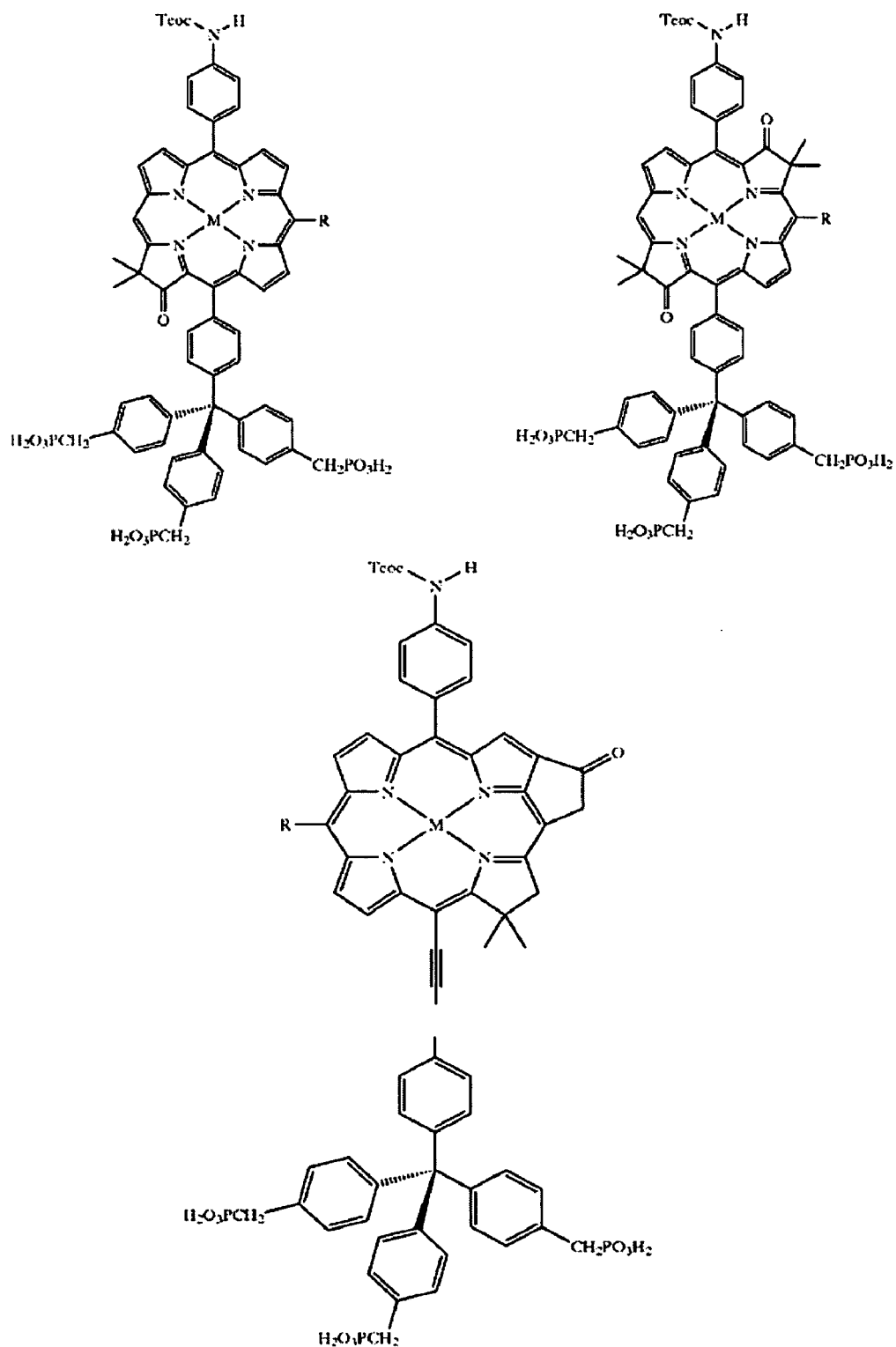

Suitable charge-separation units for attachment to the surface will be known to those of skill in the art. Thus, for example, certain surface attachment groups comprise one or more phosphonates, which bind to metal oxide surfaces with high affinity (see, e.g., FIGS. 6A and 6B).

Figure 7:
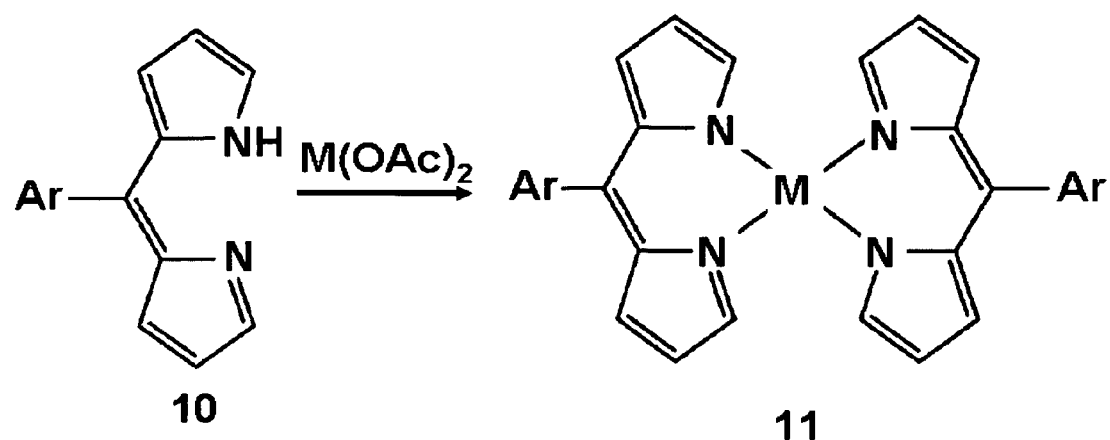
FIG. 7 illustrates the synthesis of a bis(dipyrrinato) metal complex (11).

A wide variety of molecular entities can be employed as R groups when cross-linking is desired. One example of a cross-linkable group is a free base dipyrrin (10, FIG. 7), which upon addition of a suitable metal yields the bis(dipyrrinato)metal complex (11, FIG. 7). Bis(dipyrrinato)metal complexes are well known for a variety of metals (e.g., Zn, Mg, Sn, Pd). The complexation reaction proceeds smoothly under mild conditions. The resulting bis(dipyrrinato)metal complex typically adopts a structure wherein the two dipyrrin planes are essentially orthogonal to each other. Such a structure can be accommodated with the porphyrins given the small torsional barrier toward substantial rotation of the phenyl group at the porphyrinic meso position.

Figure 8:
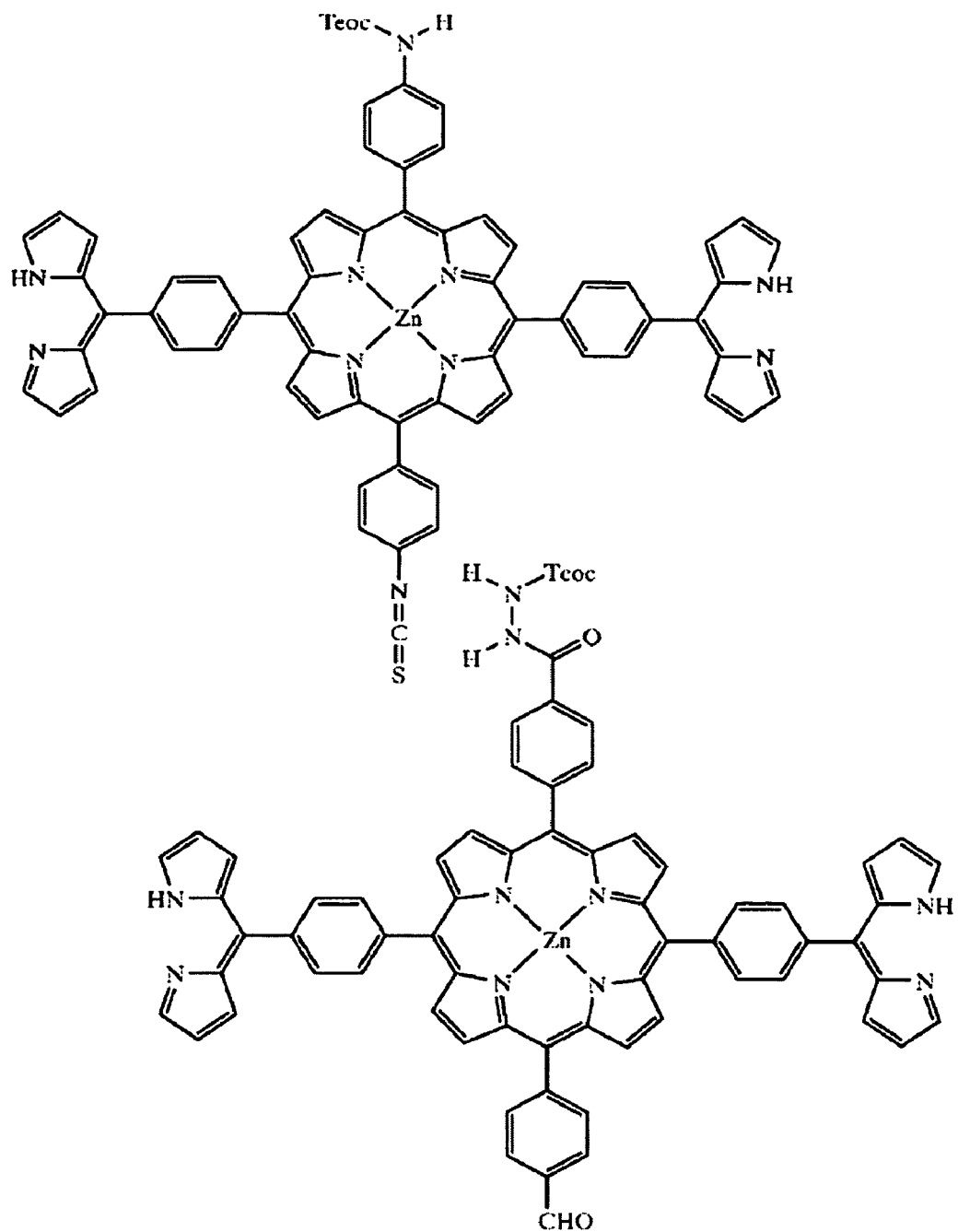
FIG. 8 illustrates bifunctional porphyrin building blocks bearing free base dipyrrins for subsequent complexation as a means of cross-linking neighboring rods.

In certain embodiments, the metal reagent can be added following or concomitant with the formation of the interpigment backbone linkage (thiourea or acid hydrazone). In certain preferred embodiments, the metal reagent does not interfere with the bond-forming process yielding the interpigment backbone. Bis(dipyrrinato)metal complexes absorb strongly in the about 500 nm region. Ideally, the bis(dipyrrinato)metal complex serves as an accessory pigment, absorbing light and funneling the resulting excited-state energy to the porphyrinic macrocycles. In this manner, the bis(dipyrrinato)metal complexes serve a mechanical role in stabilizing the growing layers and an energy conversion role in capturing light to which the porphyrinic species are relatively transparent. Two examples are provided by the zinc(II)porphyrins 12 and 13 shown in FIG. 8.

While dipyrrins are particularly attractive, other ligands can be employed (pyridyl, bipyridyl, terpyridyl, phenanthrolinyl, carboxylic acid, thiol, phosphonic acid, etc.). The cross-linking groups can be attached directly to the porphyrinic macrocycle or via a suitable linker. In general, metals and other entities (e.g., quantum dots) can also optionally be incorporated.

V. Solar Cells Incorporating Light Harvesting Arrays.

Light harvesting arrays and solar cells of the present invention can be structured, made and used in like manner as described in U.S. Pat. Nos. 6,407,330 or 6,420,648, except that the polymers/oligomers are synthesized using the stepwise protocols described herein.

Figure 9:
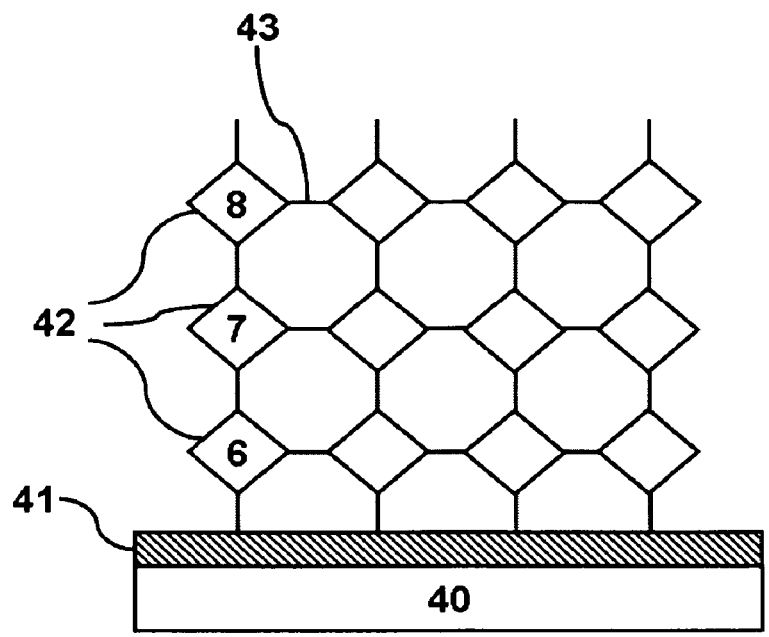
FIG. 9 schematically illustrates a light harvesting array of the present invention. A storage cell, memory element, and the like can have a similar configuration.

One example of a light harvesting array of the present invention is schematically illustrated in FIG. 9. The array generally comprises a substrate 40 carrying an electrode 41 to which a series of backbone oligomers 42 (e.g., non-discotic backbone polymers) have been electrically coupled (e.g., by covalent bond). Suitable substrates may be transparent (e.g., optically transparent even if not visually transparent) or opaque, and may be of any suitable material, such as polymer, semiconductor, insulator, etc. In some embodiments the substrate is reflective (in the direction facing the backbone polymer-). The electrode can also be formed of any suitable metallic or nonmetallic conductive material.

The polymers/oligomers generally serve as light harvesting rods and comprise a series of repeating monomeric units 6, 7, 8, a plurality of which can be porphyrinic macrocycles. In certain embodiments the rods are at least partially cross-linked 43. In various embodiments the light harvesting rods are not greater than 500 nanometers in length.

In general, the backbone oligomer comprises at least two covalently coupled porphyrinic macrocycles, such as at least two beta-coupled porphyrinic macrocycles or at least two meso-coupled porphyrinic macrocycles. The backbone polymer can be fully crosslinked or partially crosslinked as desired. The discotic backbone oligomer can optionally include a suitable group as a charge separation group or unit at its first position 6 coupled to the electrode, such as a double-decker sandwich coordination compound. In certain embodiments the backbone oligomer is preferably linear and is preferably oriented substantially perpendicularly to the substrate. The backbone oligomer can be an intrinsic rectifier of excited-state energy and/or an intrinsic rectifier of holes.

Figure 10:
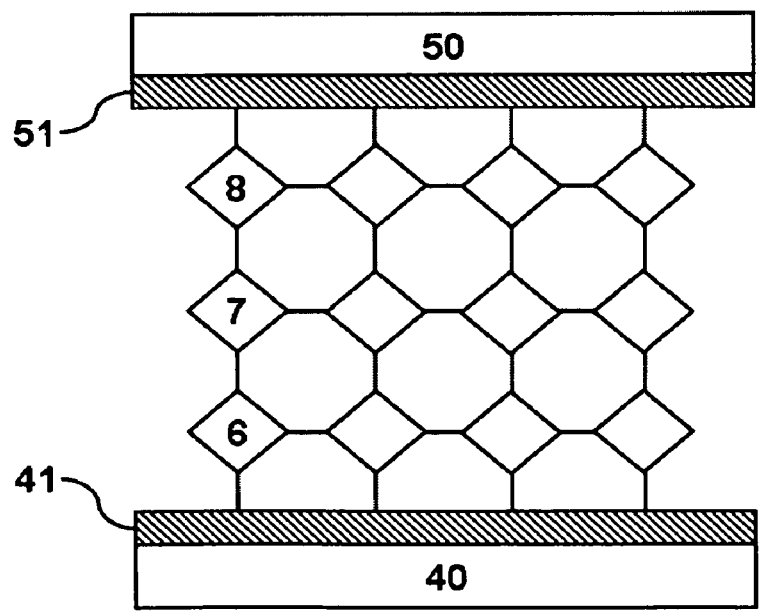
FIG. 10 schematically illustrates one configuration of a solar cell of the present invention. A storage cell, memory element, and the like can have a similar configuration.

A solar cell is schematically illustrated in FIG. 10. In certain embodiments the solar cell comprises a light harvesting array as described above, and further includes a second substrate 50 comprising a second electrode 51. The second substrate and second electrode can be formed of like or different materials as the first substrate and first electrode, with the first and second substrate being positioned to form a space therebetween, and with at least one of (i) the first substrate and the first electrode and (ii) the second substrate and the second electrode being transparent so that light can reach the light harvesting rods. Additional elements can optionally be included in the solar cell as desired depending upon the particular approach to harvesting light. Such elements may include, but are not limited to an electrolyte in the space between the first and second substrates, and/or a mobile charge carrier in the electrolyte, etc. The light harvesting rod is, in some embodiments, electrically coupled to the second electrode by any suitable means, such as covalent coupling.

Solar cells of the present invention can be used in a variety of different electrical devices. Such devices typically comprise a solar cell as described above, and a circuit (e.g., a resistive load) electrically coupled to said solar cell (e.g., by providing a first electrical coupling of the circuit to one electrode of the solar cell, and a second electrical coupling of the circuit to the other electrode of the solar cell). The solar cell may provide the sole source of power to the circuit, may be a supplemental source, may be incorporated to charge a battery, etc. Any of a variety of different electrical devices may incorporate a solar cell of the invention, including but not limited to radios, televisions, computers (such as personal computers), processors, calculators, telephones, wireless communication devices such as pagers, watches, emergency location devices, electric vehicles, emergency power supplies, power generators, lights or lamps, and other illuminating devices, monitoring devices, inspection devices, radiation detectors, imaging devices, optical coupling devices.

VI. Redox-Active Molecules (Information Storage Molecules).

The stepwise synthesis methods described herein can be used in the synthesis of a wide variety of hybrid components and/or devices (e.g. field effect transistors, sensors, memory elements, memory chips, solar cells, light harvesting arrays, etc.). In certain embodiments, the methods are used to assemble hybrid memory devices where information is stored in a redox-active information storage molecule. Certain preferred redox-active molecules suitable for use in this invention are characterized by having a multiplicity of oxidation states. In various embodiments those oxidation states can be provided by one or more redox-active units. A redox-active unit refers to a molecule or to a subunit of a molecule that has one or more discrete oxidation states that can be set by application of an appropriate voltage. Thus, for example, in one embodiment, the redox-active molecule can comprise two or more (e.g., 8) different and distinguishable oxidation states. Typically, but not necessarily, such multi-state molecules will be composed of several redox-active units (e.g., porphyrins, metallocenes, etc.). Each redox-active molecule is itself at least one redox-active unit, or comprises at least one redox-active unit, but can easily comprise two or more redox-active units.

Preferred redox-active molecules include, but are not limited to porphyrinic macrocycles, e.g., as defined herein.

Particularly preferred redox-active molecules include a porphyrin, an expanded porphyrin, a contracted porphyrin, a metallocene (e.g., ferrocene), a linear porphyrin polymer, a porphyrin sandwich coordination complex (e.g., lanthanide triple decker sandwich coordination compounds), a porphyrin array, porphyrazines, benzazoloporphyrazines, other analogs or derivatives of phthalocyanines, and the like. These structures and methods of synthesis are described in detail in U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, and the like.

In certain embodiments, the redox-active molecule is or comprises a metallocene as shown in Formula I:

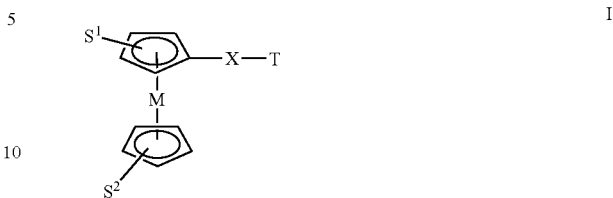

where L is a linker or a polypodal tether as described herein, M is a metal (e.g., Fe, Ru, Os, Co, Ni, Ti, Nb, Mn, Re, V, Cr, W, and the like), $S^1$ and $S^2$ are independently selected substituents including but not limited to aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. In certain embodiments, a substituted aryl group is attached to the metallocene, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

Certain suitable substituents include, but are not limited to, 4-chlorophenyl, 3-acetamidophenyl, 2,4-dichloro-4-trifluoromethyl. Preferred substituents provide a redox potential range of less than about 2 volts.

The oxidation state of molecules of Formula I is determined by the metal and the substituents and methods of determining/setting the oxidation states are described, for example, in U.S. Pat. Nos. 6,777,516, 6,728,129, 6,674,121, 6,657,884, 6,451,942, 6,381,169, 6,324,091, 6,272,038, 6,212,093, 6,208,553; PCT Publications WO 02/077633, WO 03/052835, WO 03/038886, and the like.

In certain embodiments a suitable redox-active molecule is a porphyrin illustrated by Formula II:

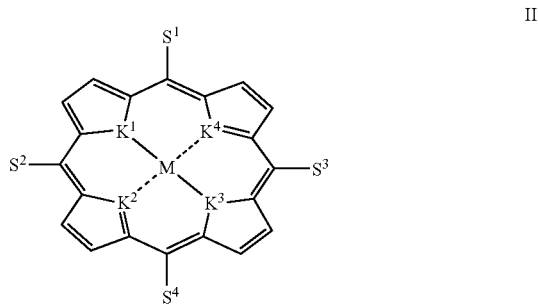

where M is present or absent and when present is a metal or a metalloid; $K^1$, $K^2$, $K^3$, and $K^4$ are independently selected and can include, but are not limited to a group IV element, a group V element, a group VI element, and CH; $S^1$, $S^2$, $S^3$, and $S^4$ are independently selected substituents and can include, but are not limited to aryl, phenyl, cycloalkyl, alkyl, halogen, alkoxy, alkylthio, perfluoroalkyl, alkenyl, alkynyl, perfluoroaryl, pyridyl, cyano, thiocyanato, nitro, amino, alkylamino, acyl, sulfoxyl, sulfonyl, imido, amido, imidazolyl, and carbamoyl. Typically in certain embodiments $S^1$, $S^2$, and $S^3$ are selected to provide a redox potential range of less than about 2 volts. In various embodiments $K^1$, $K^2$, $K^3$, and $K^4$ are independently selected and can include, but are not limited to N, O, S, Se, Te, and CH. In various embodiments M is present and is selected from the group consisting of Zn, Mg, Cd, Hg, Cu, Ag, Au, Ni, Pd, Pt, Co, Rh, Ir, Mn, B, Al, Ga, Pb, and Sn. In certain embodiments M is Zn, Mg, or Ni. In various embodiments $S^1$, $S^2$, and $S^3$ are all the same and/or $K^1$, $K^2$, $K^3$, and $K^4$ are all the same. In certain embodiments $K^1$, $K^2$, $K^3$, and $K^4$ are all N.

In one illustrative embodiment the redox-active molecule (P) can be represented by Formula III:

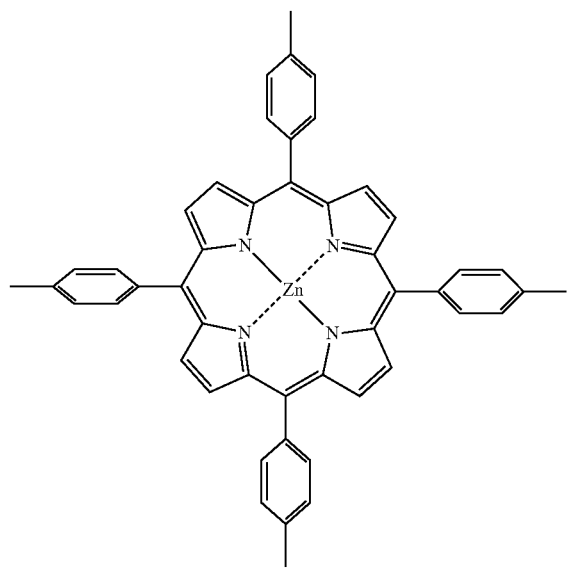

III

Other suitable redox-active molecules include, but are not limited to porphyrin sandwich compounds. The design and synthesis of suitable porphyrin arrays and sandwich compounds is described in U.S. Pat. No. 6,212,093 B1, in U.S. Patent Publications 20030169618, 20030104229, 20030092896, and by Arnold et al. (1999) Chem. Lett. 483-484).

Control over the hole-storage and hole-hopping properties of the redox-active molecules used in the memory devices of this invention allows fine control over the architecture of the memory device.

Such control is exercised through synthetic design. The hole-storage properties depend on the oxidation potential of the redox-active units or subunits that are themselves or are that are used to assemble the storage media used in the devices of this invention. The hole-storage properties and redox potential can be tuned with precision by choice of base molecule(s), associated metals and peripheral substituents (Yang et al. (1999) J. Porphyrins Phthalocyanines, 3: 117-147).

For example, in the case of porphyrins, Mg porphyrins are more easily oxidized than Zn porphyrins, and electron withdrawing or electron releasing aryl groups can modulate the oxidation properties in predictable ways. Hole-hopping occurs among isoenergetic porphyrins in a nanostructure and is mediated via the covalent linker joining the porphyrins (Seth et al. (1994) J. Am. Chem. Soc., 116: 10578-10592, Seth et al (1996) J. Am. Chem. Soc., 118: 11194-11207, Strachan et al. (1997) J. Am. Chem. Soc., 119: 11191-11201; Li et al. (1997) J. Mater. Chem., 7: 1245-1262, Strachan et al. (1998) Inorg. Chem., 37: 1191-1201, Yang et al. (1999) J. Am. Chem. Soc., 121: 4008-4018).

The design of compounds with predicted redox potentials is well known to those of ordinary skill in the art. In general, the oxidation potentials of redox-active units or subunits are well known to those of skill in the art and can be looked up (see, e.g., Handbook of Electrochemistry of the Elements). Moreover, in general, the effects of various substituents on the redox potentials of a molecule are generally additive. Thus, a theoretical oxidation potential can be readily predicted for any potential data storage molecule. The actual oxidation potential, particularly the oxidation potential of the information storage molecule(s) or the information storage medium can be measured according to standard methods. Typically the oxidation potential is predicted by comparison of the experimentally determined oxidation potential of a base molecule and that of a base molecule bearing one substituent in order to determine the shift in potential due to that particular substituent. The sum of such substituent-dependent potential shifts for the respective substituents then gives the predicted oxidation potential.

Various preferred redox-active molecules and the syntheses thereof include, but are not limited to those described in U.S. Pat. Nos. 6,208,553, 6,212,093, 6,272,038, 6,324,091, 6,381,169, and 6,451,942, and PCT Publication WO 01/03126, and the like.

EXAMPLES

The following examples are offered to illustrate, but not to limit the claimed invention.

Example 1

Stepwise Synthesis Using an Imide-Forming Reaction

Figure 3:
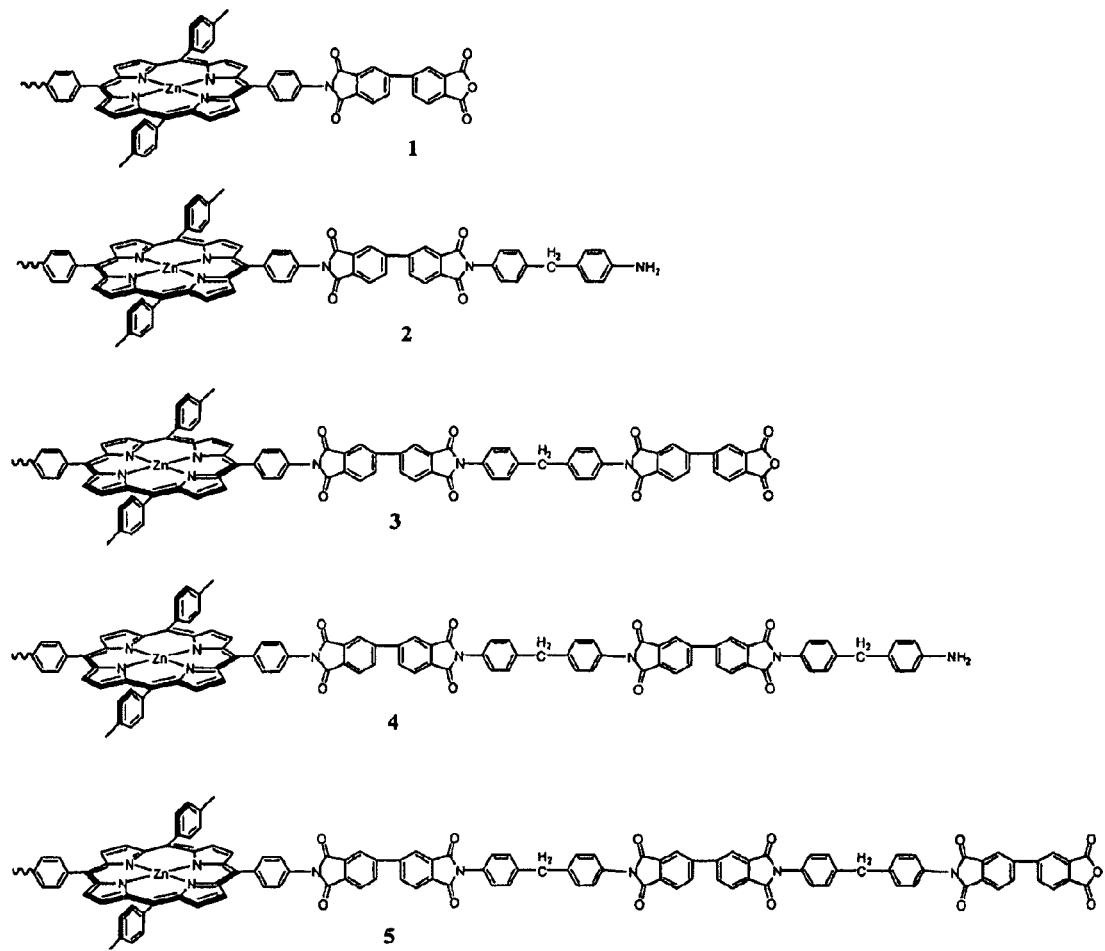
FIG. 3 illustrates products produced in the stepwise synthesis described in Example 1.

The stepwise growth process was tested using an imide forming reaction. In this experiment, a porphyrin containing an allyl tripod and an opposite 4-aminophenyl group (No. 295, FIG. 2) was first attached to a p-type Si(100) suface. Attachment to the surface occurs by reaction of the allyl groups to produce Si—C linkages. The polyimide was grown off the porphyrin base layer (FIG. 3). Growth was affected by depositing a solution containing either BPTC or MDA (FIG. 2) on top of the porphyrin and heating at 230° C. for two minutes.

Figure 4:
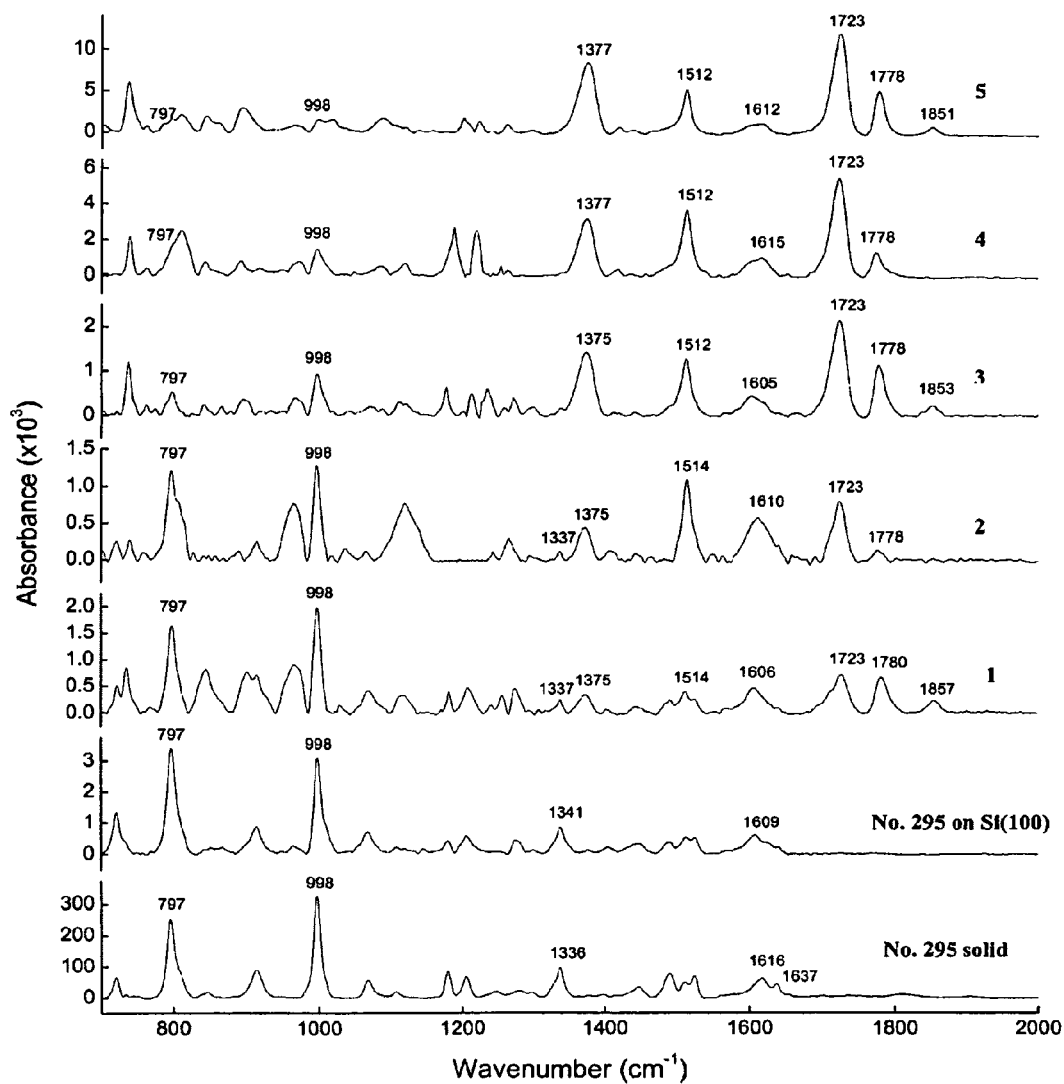
FIG. 4 shows the results of reflectance IR spectroscopy of the products produced in the stepwise synthesis described in Example 1.

The process was monitored using reflectance IR spectroscopy (FIG. 4). The bottom two spectra shown are those of the porphyrin in a solid KBr pellet and attached to the surface. The upper spectra show the effects of stepwise addition of BPTC and MDA. The third spectrum from the bottom shows the affect of the addition of BPTC. The bands at 1723 cm$^{-1}$ are the signature of the imide linkage formed by reaction of the amine group on the porphyrin and one of the anhydride groups of BPTC. The bands at 1780 cm$^{-1}$) are the unreacted anhydride. The fourth spectrum from the bottom shows the effect of adding MDA to the anhydride-modified porphyrin. The increased intensity of the imide band at 1723 cm$^{-1}$ along with the loss of intensity for the anhydride band at 1780 cm$^{-1}$ are signatures for imide formation between one of the amine groups on MDA and the unreacted anhydride group on the BPTC-modified porphyrin. The additional spectra in the figure show the effects of repeating the two imide forming steps described above. The spectra are characterized by a monotonic increase in the intensity of the imide band (1723 cm$^{-1}$) and alternating intensity of the anhydride band (1780 cm$^{-1}$), consistent with stepwise growth of the polyimide.

Example 2

Investigation of Stepwise Covalent Assembly on a Surface Yielding Porphyrin-Based Multilayer Architectures Porphyrins have been shown to be a viable medium for use in molecular-based information storage applications. The success of this application requires the construction of a stack of components ("electroactive surface/tether/charge-storage molecule/linker/electrolyte/top contact") that can withstand high-temperature conditions during fabrication (up to 400° C.) and operation (up to 140° C.). To identify suitable chemistry that enables in situ stepwise assembly of covalently linked architectures on an electroactive surface, three sets of zinc porphyrins (22 altogether) have been prepared. In the set designed to form the base layer on a surface, each porphyrin incorporates a surface attachment group (triallyl tripod or vinyl monopod) and a distal functional group (e.g., pentafluorophenyl, amine, bromo, carboxy) for elaboration subsequent to surface attachment. A second set designed for in situ dyad construction incorporates a single functional group (alcohol, isothiocyanato) that is complementary to the functional group in the base porphyrins. A third set designed for in situ multad construction incorporates two identical functional groups (bromo, alcohol, active methylene, amine, isothiocyanato) in a trans configuration (5,15-positions in the porphyrin). Each porphyrin that bears a surface attachment group was found to form a good quality monolayer on Si(100) as evidenced by the voltammetric and vibrational signatures. One particularly successful chemistry identified to date for stepwise growth entailed reaction of a surface-tethered porphyrin-amine with a dianhydride (e.g., 3,3',4,4'-biphenyltetracarboxylic dianhydride), forming the mono-imide/mono-anhydride. Subsequent reaction with a diamine (e.g., 4,4'-methylene-bis(2,6-dimethylaniline)) gave the bis(imide) bearing a terminal amine. Repetition of this stepwise growth process afforded surface-bound oligo-imide architectures composed of alternating components without any reliance on protecting groups. Taken together, the ability to prepare covalently linked constructs on a surface without protecting groups in a stepwise manner augurs well for the systematic assembly of a wide variety of functional molecular devices.

Over the past few years we have been working to develop approaches for molecular based information storage. In this approach, redox-active molecules are employed to store charge; the presence of stored charge at a given potential represents the storage of information. This approach is amenable to implementation in a hybrid technology wherein the charge-storage molecules replace the material that presently serves as the charge-storage medium in existing memory chips. As part of this program, we have prepared a wide variety of redox-active molecular architectures, particularly porphyrinic molecules, as candidates for information-storage applications (1. Balakumar et al. (2004) *J. Org. Chem.* 69: 1435-1443; Muthukumaran et al. (2004) *J. Org. Chem.* 69: 1444-1452; Loewe et al. (2004) *J. Org. Chem.*, 69: 1453-1460; Wei et al. (2004) *J. Org. Chem.*, 69: 1461-1469; Liu et al. (2004) *J. Org. Chem.*, 69: 5568-5577; Lysenko et al. (2005) *J. Porphyrins Phthalocyanines*, 9: 491-508; Wei et al. (2005) *J. Phys. Chem. B* 109: 6323-6330; Thamyongkit et al. (2006) *J. Org. Chem.* 71: 903-910).

The design of the information-storage molecules typically includes a redox-active unit and a tether for attachment to a surface. In laboratory studies, the information-storage molecule is attached to an electroactive surface, a liquid or gel electrolyte is added, and a counter electrode is contacted to the electrolyte to complete the electrochemical cell that constitutes the memory device (Roth et al. (2000) *J. Vac. Sci. Technol. B*. 18: 2359-2364; Roth et al. (2003) *J. Am. Chem. Soc.*, 125: 505-517). For real-world implementation in a hybrid molecular-semiconductor device, the fabrication of the memory device presents a number of challenges: (1) The charge-storage molecules must be incorporated as components in a "stack" that consists of "electroactive surface/tether/charge-storage molecule/linker/electrolyte/top contact." (2) The electrolyte should be sufficiently thin to afford rapid electron-transfer reactions yet sufficiently thick to minimize electric shorts (via pinholes) between the electroactive surface and the top contact. The ideal dimensions of the electrolyte are considered to be ~10 nm. (3) Sufficient charge density must be present to reliably read the stored information. For the feature sizes in current memory cells, the requisite charge density can be achieved with a monolayer of monomeric porphyrins on a planar substrate (Kuhr et al. (2004) Mater. Res. Soc. Bull., 838-842; Padmaja et al. (2005) *J. Org. Chem.* 70: 7972-7978) Nevertheless, as feature sizes for memory cells become smaller, assemblies of monomeric porphyrins will not have the requisite charge density for reliable read out (Thamyongkit et al. (2006) *J. Org. Chem.* 71: 903-910). Accordingly, multilayer architectures of redox-active molecules will be needed to maintain the required amount of charge stored in each cell.

Two distinct methods can be considered for assembly of the "stack" of components in a memory cell:

1) Attach a pre-synthesized molecular architecture to the electroactive surface. We have explored this approach at length; although porphyrin dyads and triads have been prepared, such constructs attach to the surface with an increased molecular footprint that partially attenuates the greater charge density expected from the multad design (Thamyongkit et al. (2006) *J. Org. Chem.* 71: 903-910; Clausen et al. (2000) *J. Org. Chem.* 65: 7363-7370).

2) Build the stack in a stepwise process on the electroactive surface. A number of multilayer assembly procedures have been developed over the years, epitomized by the Langmuir-Blodgett method (Ulman (1991) *An Introduction to Ultrathin Organic Films*; Academic Press: Boston.). Most such approaches afford non-covalent assemblies. Given the excursions in temperature to which the chip is exposed, both during fabrication (up to 400° C.) and operation (up to 140° C.), we focused on the fabrication of covalently linked architectures.

Figure 11:
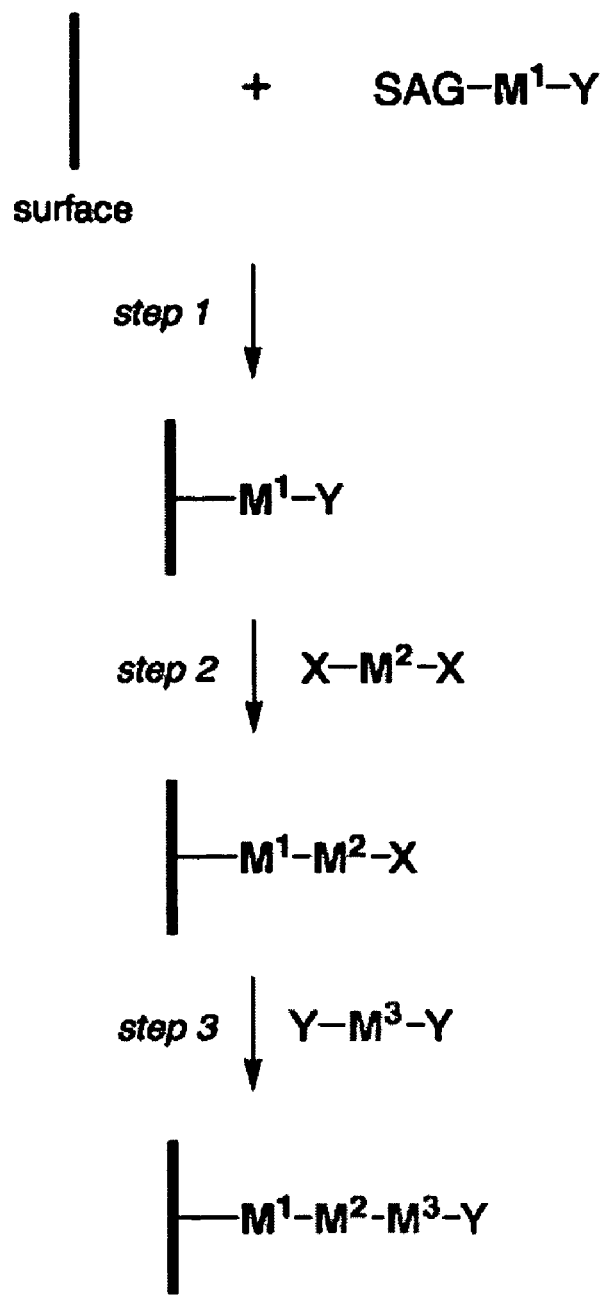
FIG. 11 shows Scheme 1 of Example 2.

A conceptual outline for in situ formation of covalently linked architectures is shown in Scheme 1 (FIG. 11). A charge-storage molecule that bears a surface attachment group (SAG) and distal functional group (Y) is attached to an electroactive surface (step 1). A monomer bearing a functional group (X) complementary to Y is then attached (step 2). In considering approaches for further elaboration of the stack, we realized that the stepwise growth process might be carried out with a pair of difunctional monomers wherein each monomer bears two identical functional groups. For example, with monomers X-$M^1$-X and Y-$M^2$-Y, the coupling could be carried out step-by-step without use of protecting groups to generate oligomers composed of -$M^1$-$M^2$-$M^1$-$M^2$ . . . $M^i$-. The success of this method would stem from (1) growth on a surface, which effectively blocks one site of reactivity on the initial monomer, (2) monomers that are inherently symmetrical with respect to their two functional groups, and (3) the use of relatively rigid monomers wherein reactivity between components at different sites on the surface is effectively suppressed. This approach differs from the synthesis of biomolecules on a polymeric resin (e.g., solid-phase peptide synthesis) or on a surface (e.g., DNA chip fabrication). In the synthesis of peptides, for example, each amino acid contains an amino group and a carboxylic acid moiety (x-m-y), one of which must be protected while the other is activated to prevent self-condensation. The advantage of avoiding protecting groups lies in synthetic convenience and efficiency, where every reaction carried out contributes to the growth of the stack of components necessary to construct the memory cell. Note that in principle the monomer M can comprise a charge storage entity, a spacer, an electrolyte, a tether for surface attachment, and so forth.

To successfully implement the in situ covalent assembly method, the following criteria should be met: (1) The Y group in the compound forming the base layer preferably does not attach to the surface and preferably survives the surface attachment process. In this regard, the method of attachment of the porphyrinic-based charge-storage molecules to Si(100) entails a high-temperature (300-400° C.) baking or sublimation process (Liu et al. (2004) *J. Org. Chem.*, 69: 5568-5577; Roth et al. (2003) *J. Am. Chem. Soc.*, 125: 505-517). (2) The Y group should enable derivatization with the next layer. (3) The derivatization chemistry should be compatible with the surface, the components in the preceding layer (e.g., the porphyrinic charge-storage material), and the modular components that will be attached or deposited in subsequent layers. (4) The entire construct must be compatible with device operation. There was little precedent in organic chemistry to guide the selection of Y groups and derivatization chemistries that satisfy the aforementioned criteria, particularly the high-temperatures of surface attachment and device operation. Indeed, an early effort toward this goal encountered inadequate selectivity of the SAG versus the Y group in the base porphyrin upon attempted surface attachment, as well as competing surface reactions upon addition of the components designated to form the second layer (Carcel et al. (2004) *J., Org. Chem.* 69: 6739-6750). Accordingly, we embarked on a program to examine a set of porphyrins for suitability in these applications. The porphyrins of interest include the base porphyrin, which is attached to the electroactive surface, and porphyrins that can be attached to the base porphyrin in building a stack of redox-active compounds for increased charge density.

Figure 12:
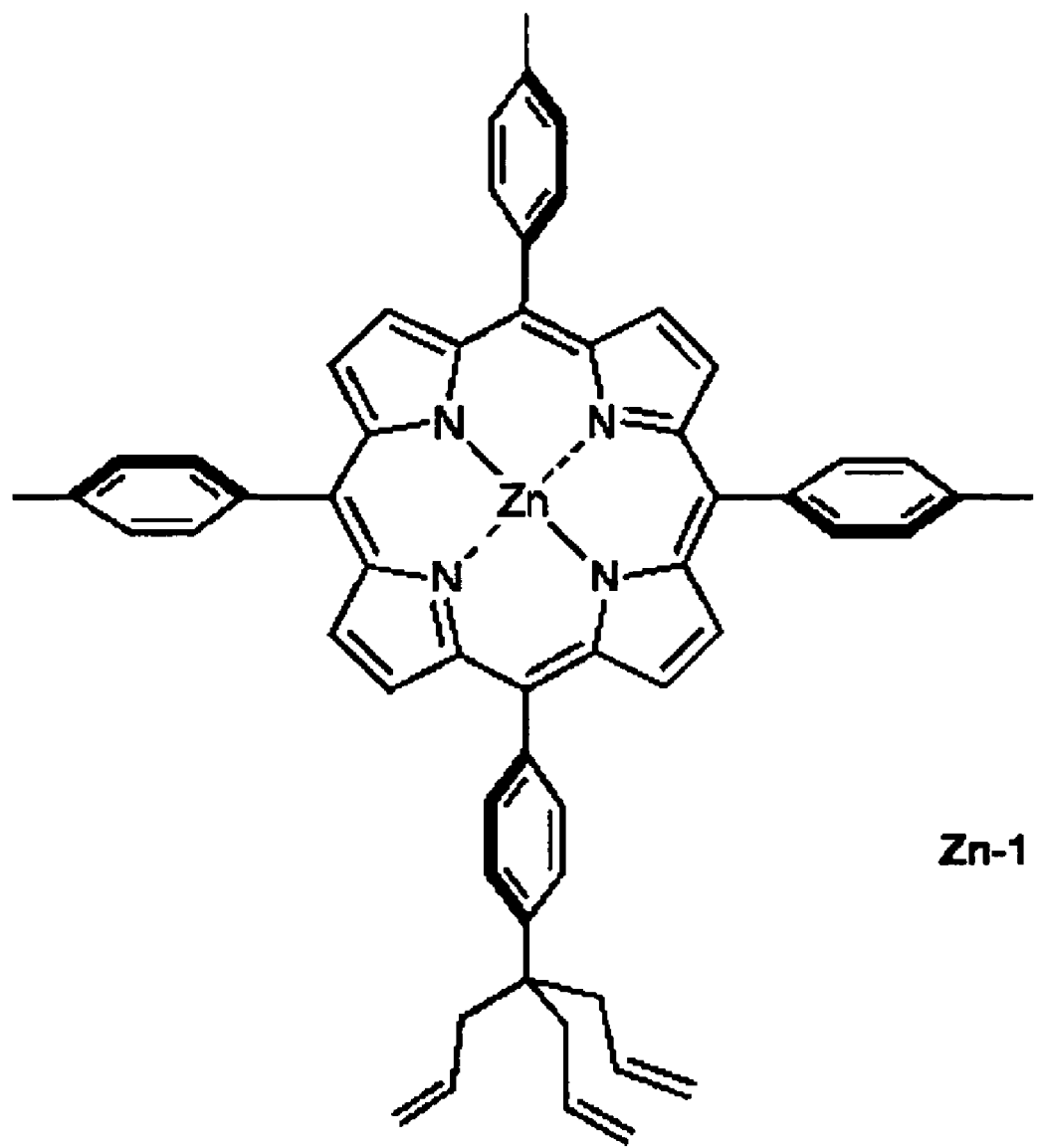
FIG. 12 illustrates a prepared a porphyrin bearing a "triallyl" tether.

In this example, we describe the synthesis of a series of 22 porphyrins for studies of in situ covalent assembly accompanied by a survey of their use. The example is divided into three parts. Part I describes the synthesis of a family of molecules built around a zinc porphyrin bearing a tripodal allyl tether (for surface attachment) and a distal functional group (for subsequent elaboration). We previously prepared a porphyrin bearing a "triallyl" tether (FIG. 12), (see, e.g., copending application U.S. Ser. No. 11/446,586 and PCT/US2006/021516) which was found to afford a compact molecular footprint upon attachment to Si(100). Part II describes the synthesis of porphyrins that bear one or two functional groups for use in the in situ construction of porphyrin dyads or multads, respectively, to give high-charge density architectures. Part III describes the results of studies that assess the suitability of the functional groups for derivatization purposes. This work establishes a new approach for building molecular architectures on a surface that is particularly appropriate for assembling the vertical stack of components required for hybrid molecular-semiconductor information-storage devices.

Results and Discussion.

Part I. Porphyrins for Surface Attachment and Subsequent Elaboration.

A. Molecular Design.

The key reactions we sought to examine are shown in Table 2. The reactions selected for examination require few or no added reagents. The reactions are primarily aimed at derivatization of porphyrins, although a number may have broader scope. Most of the reactions are well precedented. For example, pentafluorophenyl-substituted porphyrins are known to undergo nucleophilic displacement of the p-fluoro substituent (entry 1) (Battioni et al. (1991) *Tetrahedron Lett.* 32: 2893-2896). The reaction of an amine with an anhydride can afford the acid-amide 18 (not shown), which proceeds to the imide (entry 2) (Gosh and Mittal (1996) *Polyimides: Fundamentals and Applications* K. L Marcel New York). Porphyrins upon electrochemical oxidation are undergo nucleophilic substitution (entry 3) (Jaquinod (2000) In: *The Porphyrin Handbook*; Kadish et al. eds., Academic Press: San Diego, 1: 201-237). In the same vein, a pyrrole attached to a porphyrin can undergo oxidative oligomerization with pyrrole in solution (entry 4) (Carvalho de Medeiros et al. (1996) *Inorg Chem.*, 35: 2659-2664). A porphyrin directly attached halo substituent may undergo nucleophilic displacement (entry 5) (Jaquinod (2000) In: *The Porphyrin Handbook*; Kadish et al. eds., Academic Press: San Diego, 1: 201-237). A carboxylic acid substituent may enable electrostatic assembly of a cationic oligomer, as required for placement of the electrolyte material (entry 6). The lone pair of electrons on nitrogen in a pyridyl or benzonitrile group can be exploited for binding a metal coordination complex (entries 7 and 8) (Chambron et al. (2000) In *The Porphyrin Handbook*; Kadish et al. eds., Academic Press: San Diego, Calif., 6: 1-42).

TABLE 2

Prototypical reactions for stepwise assembly on a surface.

| Entry | Surface Reactant Prophyrin-Y | Reactant X—M | Surface Attached Product Porphyrin-M |
|---|---|---|---|
| 1 | Por—C6F5 (pentafluorophenyl) | HO—R | Por—C6F4—O—R |

TABLE 2-continued

Prototypical reactions for stepwise assembly on a surface.

| Entry | Surface Reactant<br>Prophyrin-Y | Reactant<br>X—M | Surface Attached Product<br>Porphyrin-M |
|---|---|---|---|
| 2 | Por—⟨C₆H₄⟩—NH₂ | phthalic anhydride with R | Por—⟨C₆H₄⟩—N(phthalimide)—R |
| 3[a] | Por—H | Nu—R | Por—Nu—R |
| 4[a] | Por—pyrrole (N-H) | pyrrole (N-H) | Por—(pyrrole)ₙ—H |
| 5 | Por—Br | HO—R | Por—OR |
| 6 | Por—⟨C₆H₄⟩—CO₂H | (oligomer)⁺ | Por—⟨C₆H₄⟩—CO₂⁻ (oligomer)⁺ |
| 7 | Por—⟨pyridine⟩ | ⟩—R + MX₂ | Por—⟨pyridine⟩—M····—R |
| 8 | Por—⟨C₆H₄⟩—CN | ⟩—R + MX₂ | Por—⟨C₆H₄⟩—C≡N····M—R |

[a]Reaction requires an oxidant.

Figure 13:
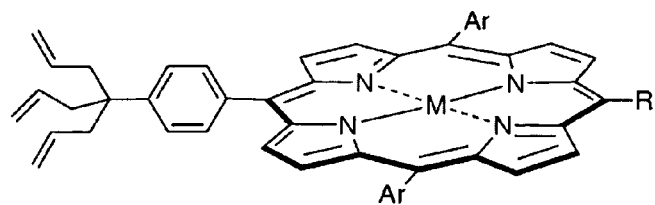
FIG. 13 (chart 2) shows a set of porphyrins (Zn-2-Zn-12).
Figure 13:
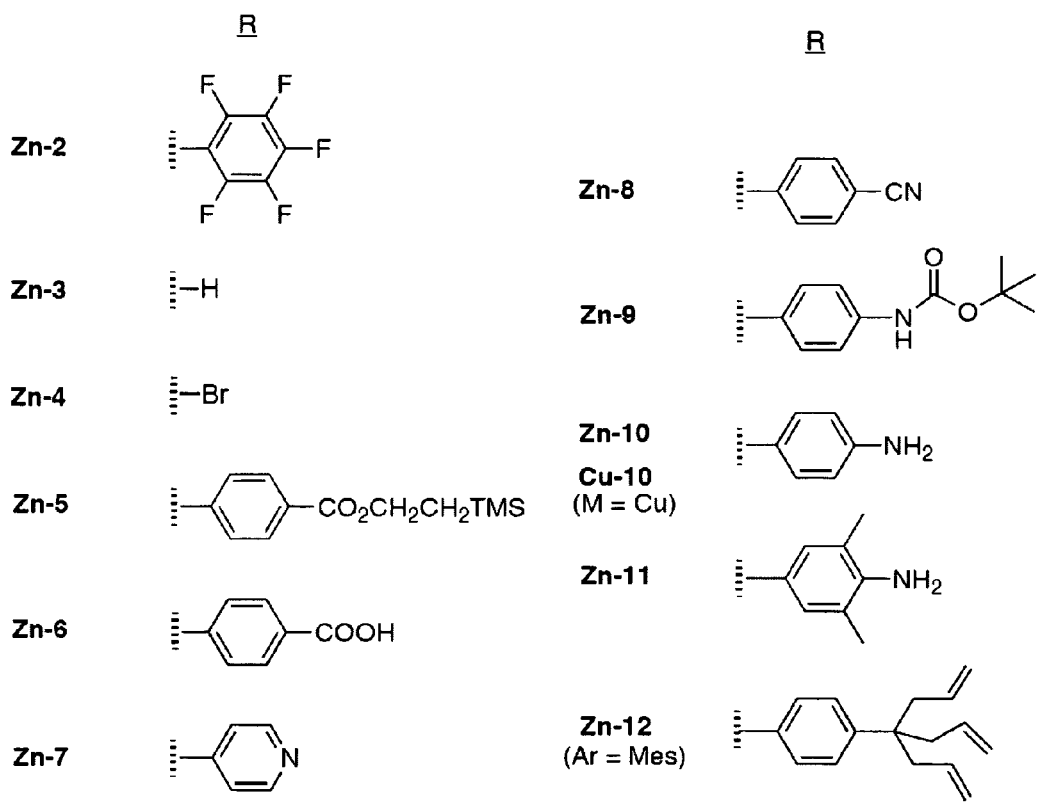
Figure 14:
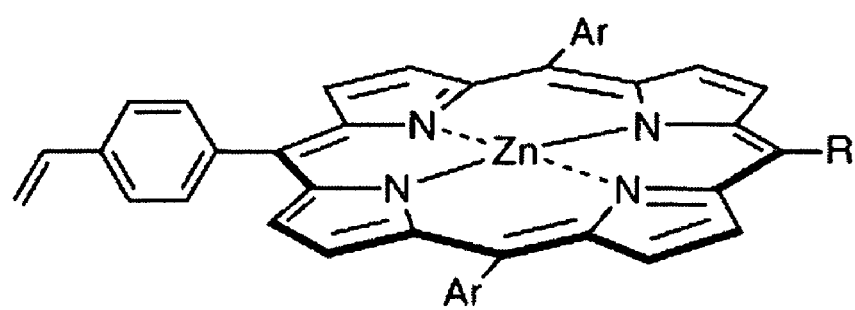
FIG. 14 (chart 3) shows a second set of porphyrins (Zn-13, Zn-14) that each bear a single vinyl tether and a distal functional group.
Figure 14:
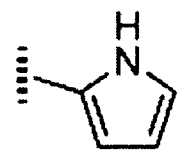
Figure 14:
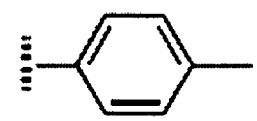
Figure 14:
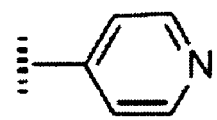

A set of porphyrins (Zn-2–Zn-12) for investigation of these derivatization processes is shown in Chart 2 (FIG. 13). Each molecule incorporates a zinc porphyrin as an electroactive unit, a triallyl tether, and a distal functional group. The members of a second set of porphyrins (Zn-13, Zn-14) each bear a single vinyl tether and a distal functional group (Chart 3, FIG. 14).

B. Synthesis.

Figure 15:
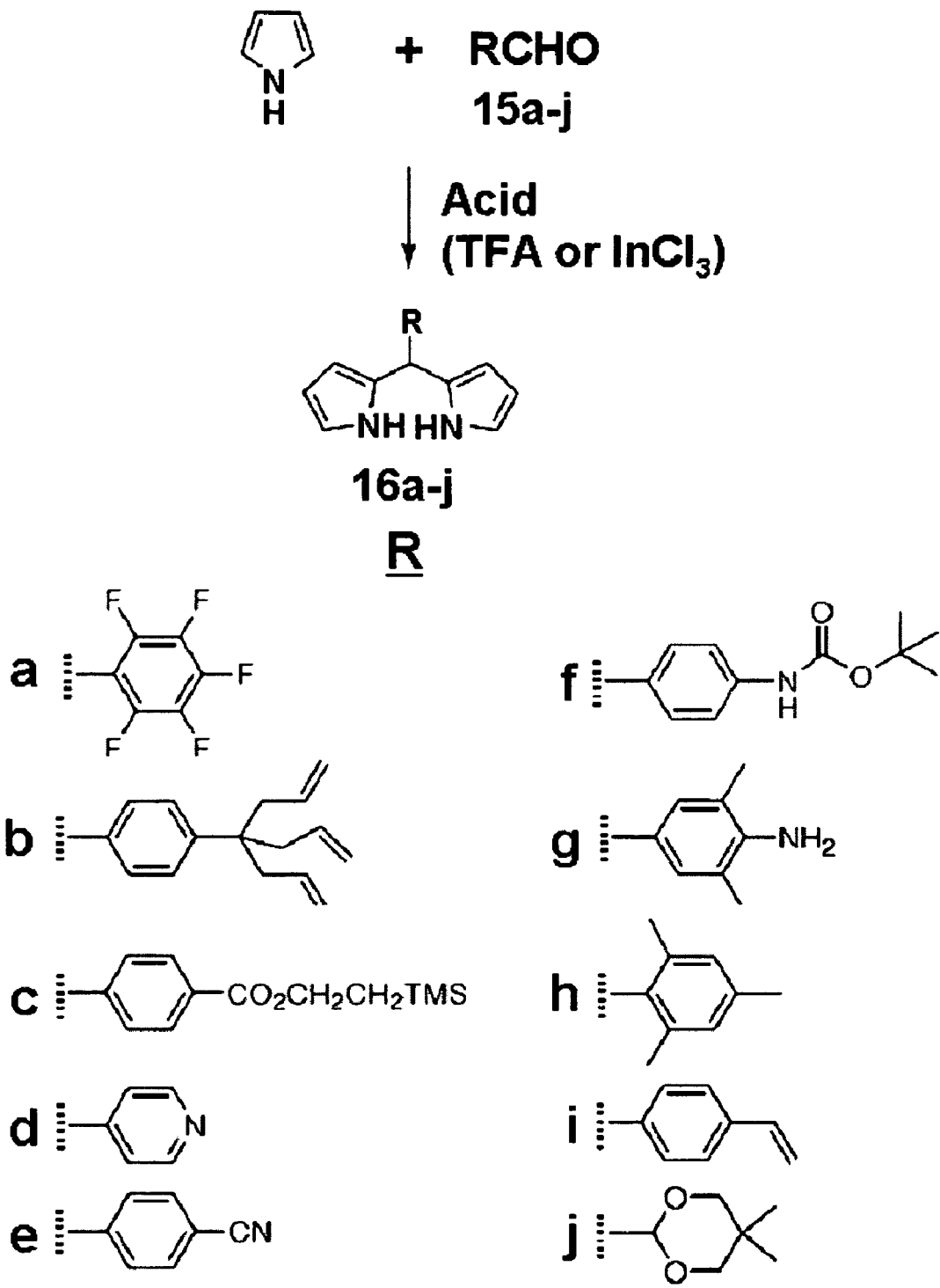
FIG. 15 shows synthesis Scheme 2 of Example 2.

The syntheses described herein generally make use of mild rational methods developed over the past few years for preparing porphyrins bearing up to four different meso substituents (Littler et al. (1999) *J. Org. Chem.*, 64: 2864-2872; Rao et al. (2000) *J. Org. Chem.* 65: 7323-7344; Geier et al. (2001) *J. Porphyrins Phthalocyanines* 5: 810-823; Fan et al. (2005) *Tetrahedron*, 61: 10291-10302). Each of Zn-2–Zn-14 is a trans-AB2C-porphyrin. The core porphyrin-forming reaction requires access to dipyrromethanes and 1,9-diacyldipyrromethanes. The synthesis of dipyrromethanes proceeds by condensation of an aldehyde with excess pyrrole in the presence of an acid catalyst (e.g., TFA or InCl₃) at room temperature (Littler et al. (1999) *J. Org. Chem.*, 64: 1391-1396; Laha et al. (2003) *Org. Process Res. Dev.* 7: 799-812). In this manner, aldehydes 15a-j afforded the corresponding dipyrromethanes 16a (Laha et al. (2003) *Org. Process Res. Dev.* 7: 799-812), 16b (Padmaja et al. (2005) *J. Org. Chem.* 70: 7972-7978), 16c (Tomizaki et al. (2003) *J. Org., Chem.* 68: 8199-8207), 16d (Gryko and Lindsey (2000) *J. Org. Chem.*, 65: 2249-2252), 16e (Rao et al. (2000) *J. Org. Chem.* 65: 7323-7344), 16f, 16g, 16h (Laha et al. (2003) *Org. Process Res. Dev.* 7: 799-812), 16i (Liu et al. (2004) *J. Org. Chem.*, 69: 5568-5577), 16j (Balakumar et al. (2004) *J. Org. Chem.* 69: 5112-5115), of which 16f and 16g and are new compounds (Scheme 2, FIG. 15). Commercially available aldehydes were employed with the exception of 15b (Padmaja et al. (2005) *J. Org. Chem.* 70: 7972-7978), 15f (Rai and Katzenellenbogen (1992) *J. Med. Chem.* 35, 4150-4159), and 15g (Lal et al. (1984) *Tetrahedron Lett.* 25, 2901-2904), which were prepared as described in the literature.

Figure 16:
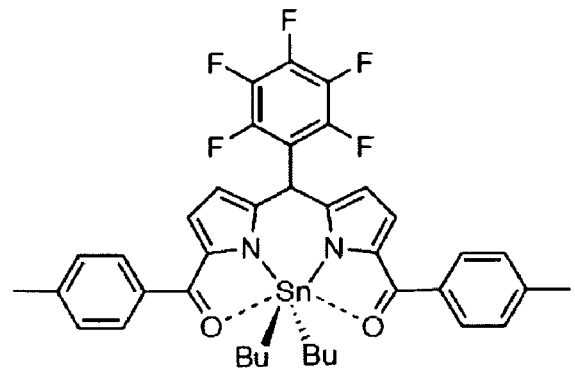
FIG. 16 shows Scheme 3 for the synthesis of Zn-2 in Example 2.
Figure 16:
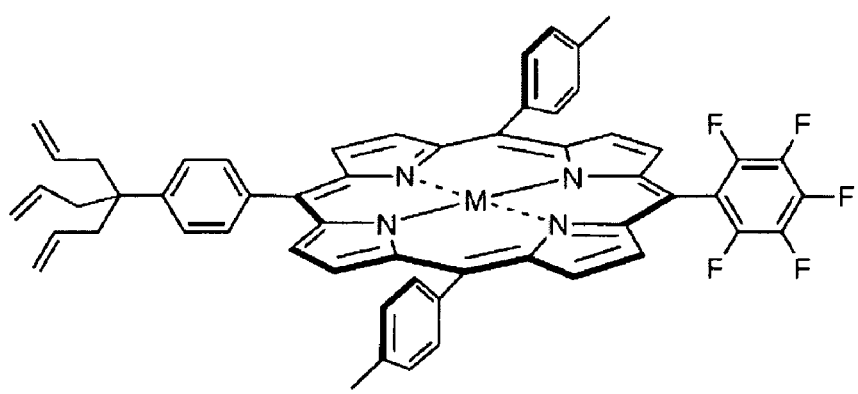

The synthesis of porphyrin Zn-2 is shown in Scheme 3 (FIG. 16). Diacylation (Tamaru et al. (2004) *J. Org. Chem.*, 69: 765-777) of 5-(pentafluorophenyl)dipyrromethane (16a) followed by complexation with dibutyltin dichloride (to facilitate workup) afforded the dipyrromethane-tin complex 17 in 18% yield. Reduction of 17 with NaBH₄ afforded the corresponding dipyrromethane-dicarbinol. Reaction of the latter with the "triallyl" dipyrromethane 16b in CH₂Cl₂ containing Yb(OTf)₃ followed by oxidation with DDQ gave porphyrin 2 in 30% yield. Zinc metalation of 2 afforded Zn-2 in 76% yield.

Figure 17:
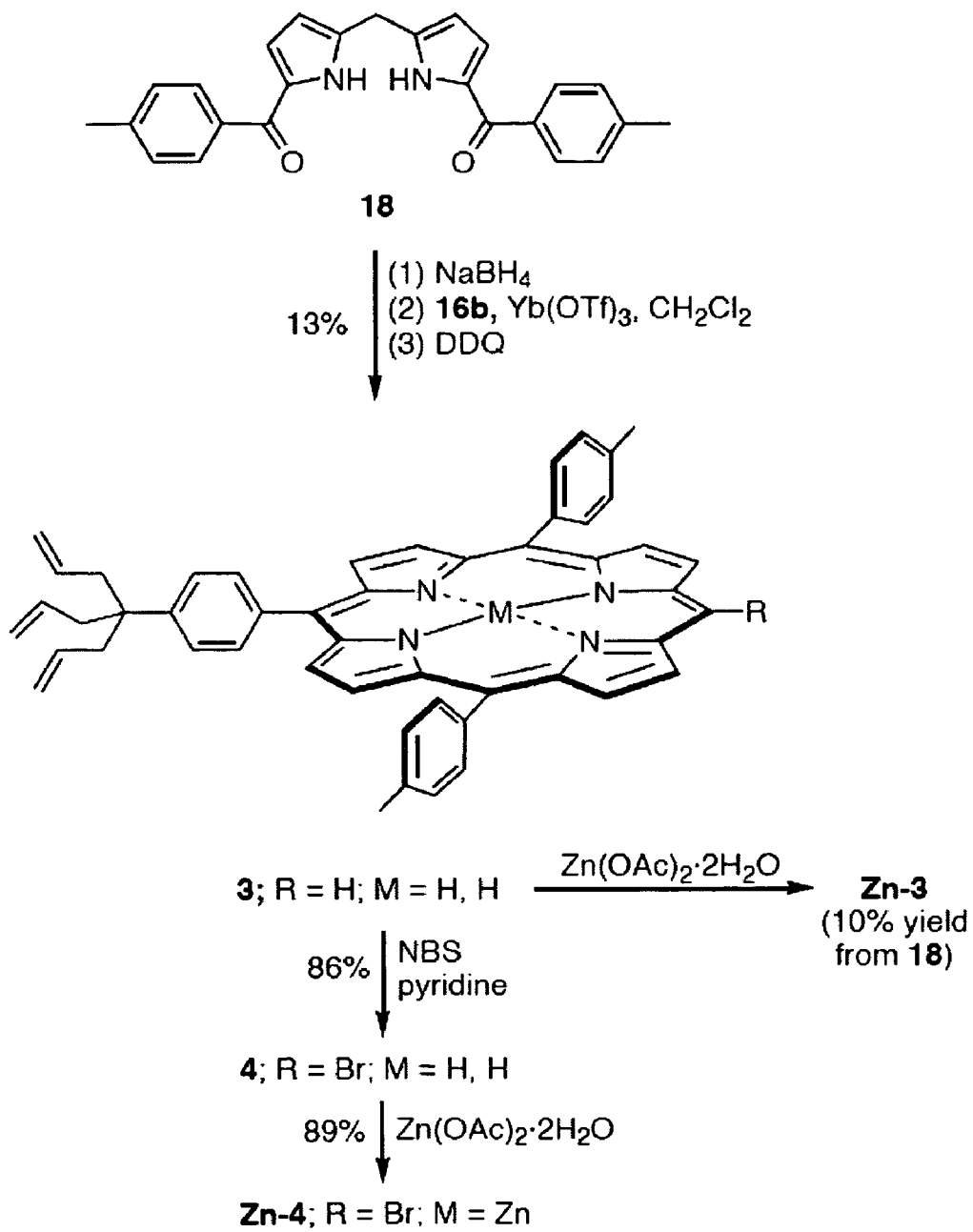
FIG. 17 shows Scheme 4 for the synthesis of Zn-3 in Example 2.

The synthesis of porphyrin Zn-3 is shown in Scheme 4, FIG. 17. Reduction of the meso-unsubstituted 1,9 diacyldipyrromethane 18 (Id.) with NaBH₄ afforded the corresponding dipyrromethane-dicarbinol. The latter was condensed with 16b in the presence of Yb(OTf)₃ followed by oxidation with DDQ, affording the free base porphyrin 3. Treatment of 3 with NBS (Nudy et al. (1984) *Tetrahedron* 40: 2359-2363; (b) DiMagno et al. (1993) *J. Org. Chem.*, 58: 5983-5993; Yu et al. (2003) *Inorg. Chem.*, 42: 6629-6647) at 0° C. afforded the meso-bromo porphyrin 4 in 86% yield, showing the chemoselectivity of the porphyrin meso-position versus the three allyl groups. Zinc metalation of 3 or 4 afforded Zn3 or Zn-4, respectively.

The strategy for preparing porphyrins Zn-2, Zn-3 and Zn-4 entailed use of the triallyl dipyrromethane and the diacyldipyrromethane bearing the distal functional group. The preparation of the porphyrins bearing sensitive functional groups destined for the distal site required reversal of this strategy, wherein the triallyl-dipyrromethane carried the 1,9-diacyl moieties. The sole consideration in the two approaches centers around the compatibility of the functional group with the conditions for 1,9 diacylation (EtMgBr/ArCOCl) and reduction to the dicarbinol (NaBH$_4$ in THF/MeOH).

Figure 18:
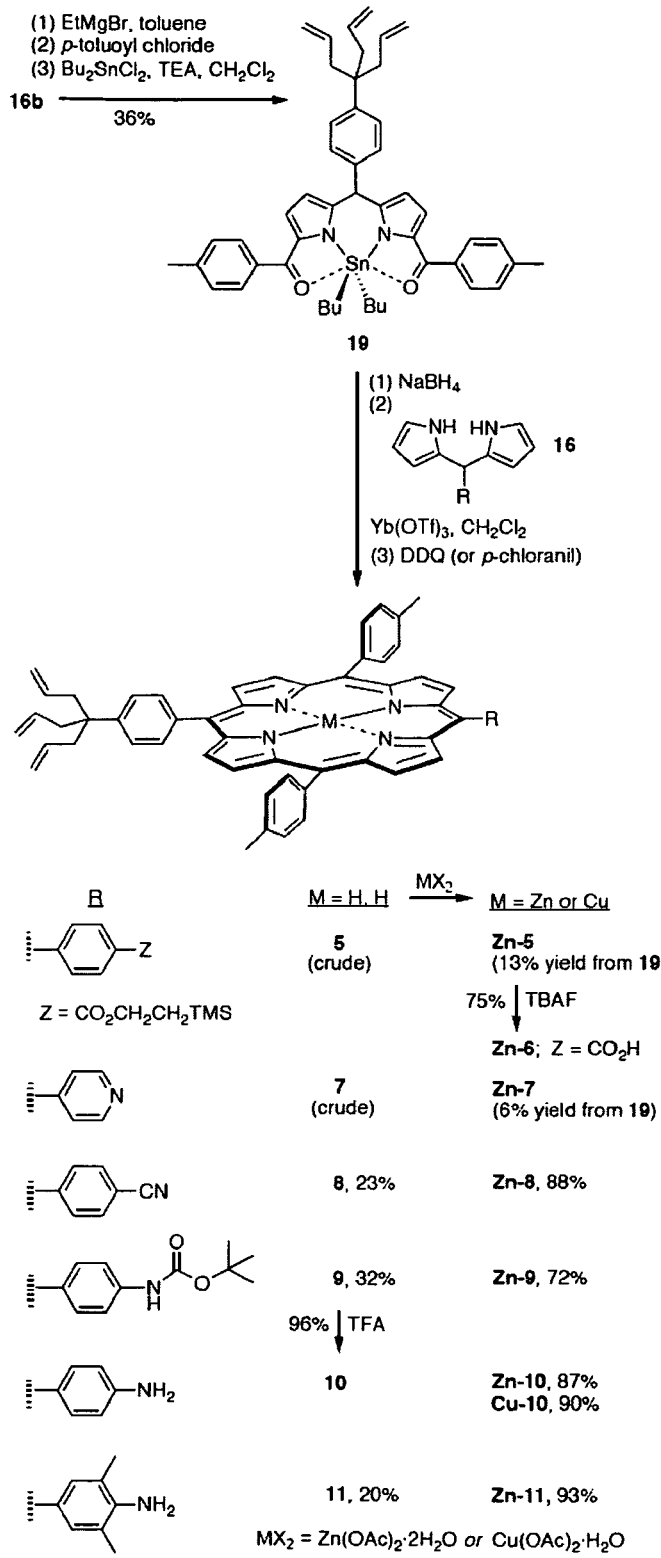
FIG. 18 shows synthesis Scheme 5 of Example 2.

Diacylation of triallyl-dipyrromethane 16b followed by tin-complexation afforded the dipyrromethane-tin complex 19 (Scheme 5, FIG. 18). This valuable compound was reduced with NaBH$_4$ to give the corresponding dipyrromethane-dicarbinol. Condensation of the latter with a dipyrromethane (16c, 16d, 16e, 16f, or 16g) followed by oxidation and metalation gave the corresponding porphyrin (Zn-5, Zn-7, Zn-8, Zn-9, or Zn-11). Treatment of Zn-5 with TBAF cleaved the trimethylsilylethyl group, thereby providing Zn-6. Treatment of BOC-protected aminoporphyrin 9 with TFA afforded the free base aminoporphyrin 10 in quantitative fashion. Metalation of 10 afforded Zn-10 or Cu-10 in 87% or 90% yield.

Figure 19:
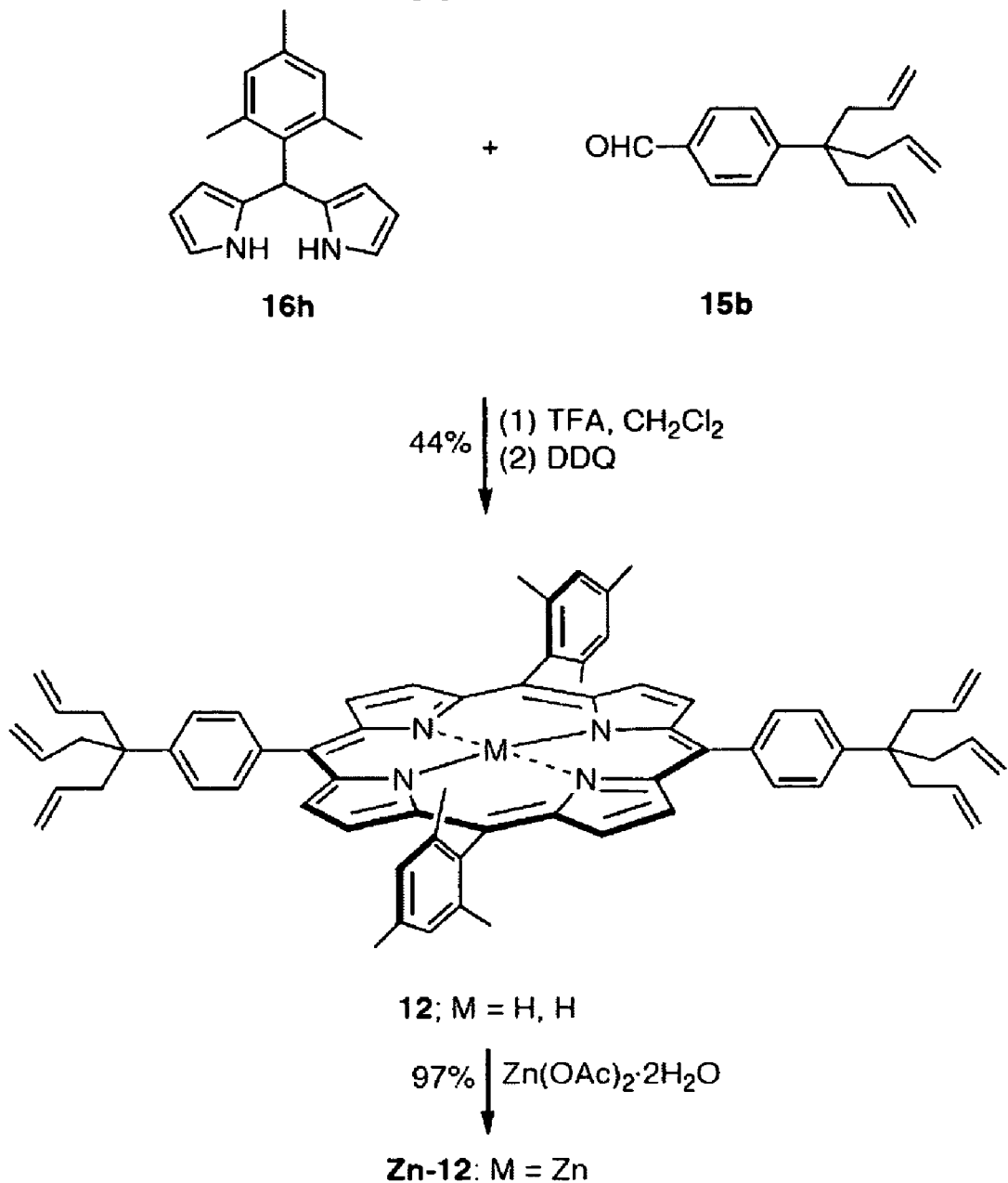
FIG. 19 shows Scheme 6 for the synthesis of Zn-12 in Example 2.

The condensation of 5-mesityldipyrromethane (16h) with the aldehyde tripod 15b using TFA catalysis (Littler et al. (1999) *J. Org. Chem.*, 64: 2864-2872) followed by oxidation with DDQ afforded the free base porphyrin 12 in 44% yield. Subsequent metalation with Zn(OAc)$_2$.2H$_2$O afforded Zn-12 in 97% yield (Scheme 6, FIG. 19).

Figure 20:
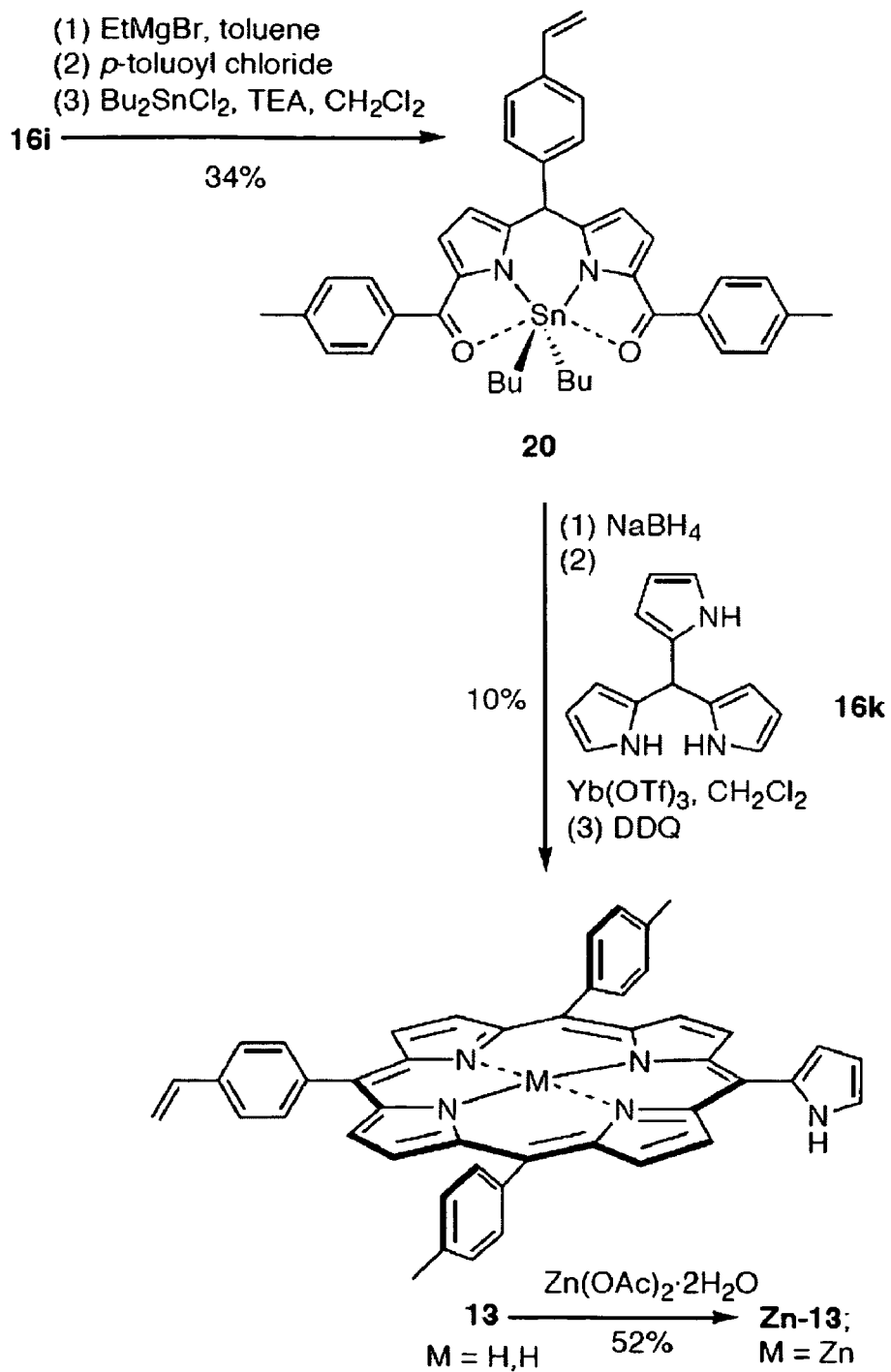
FIG. 20 shows Scheme 7 for the synthesis of a porphyrin bearing a 2-pyrrolyl group and a 4-vinylphenyl tether in Example 2.

The synthesis of a porphyrin bearing a 2-pyrrolyl group and a 4-vinylphenyl tether is outlined in Scheme 7, FIG. 20. Tri(pyrrol-2-yl)methane (16k) was prepared by the known reaction of triethyl orthoformate and pyrrole with chloroacetic acid (Reese and Yan (2001) *Tetrahedron Lett.*, 42: 5545-5547). Diacylation of 5-(4-vinylphenyl)dipyrromethane (16i) followed by tin-complexation provided dipyrromethane-tin complex 20 in 34% yield. Reduction of 20 with NaBH$_4$ afforded the corresponding dipyrromethane-dicarbinol, which upon Yb(OTf)$_3$ mediated condensation with 16k followed by oxidation with DDQ gave porphyrin 13 in 10% yield. Treatment of 13 with Zn(OAc)$_2$.2H$_2$ provided Zn-13 in 52% yield.

Figure 21:
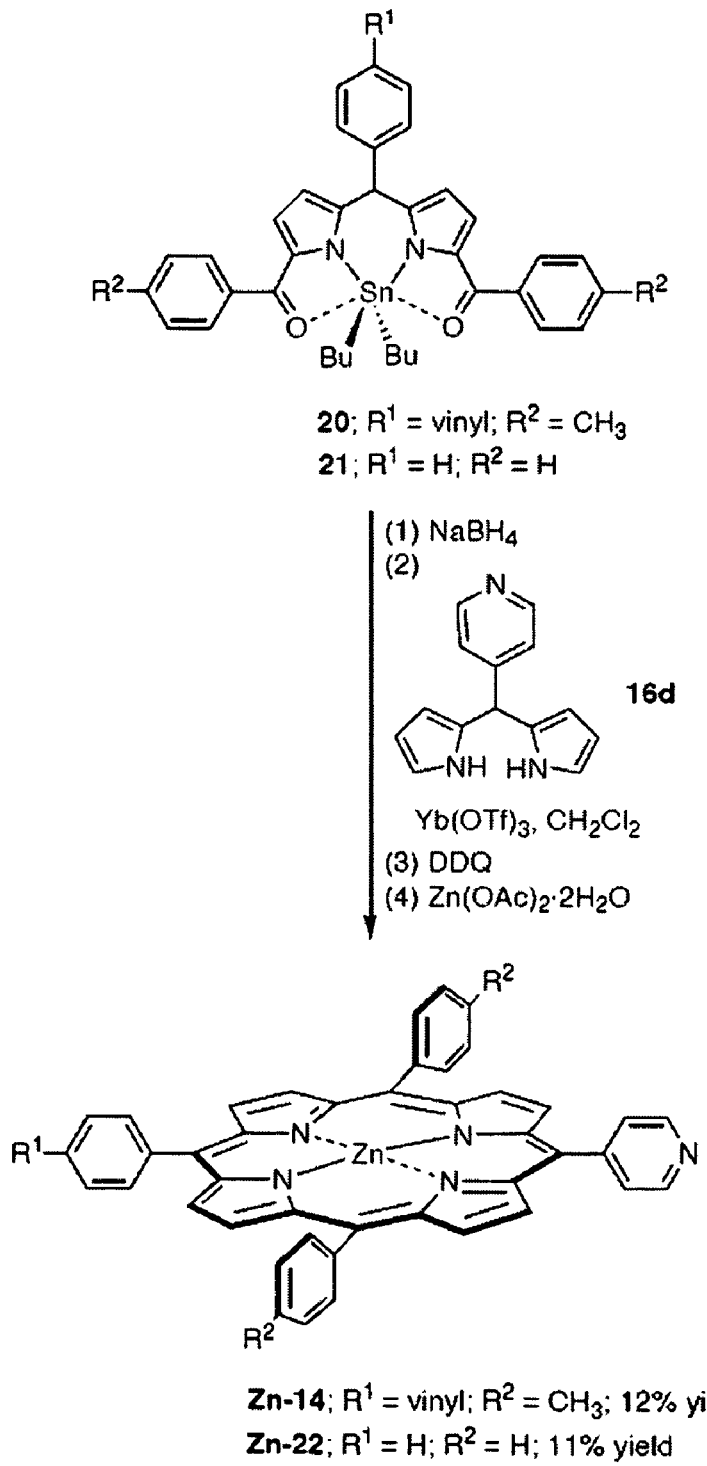
FIG. 21 shows Scheme 8 for the synthesis of two pyridyl-substituted porphyrins (Zn-14 and Zn-22) in Example 2.

The synthesis of two pyridyl-substituted porphyrins (Zn-14 and Zn-22) is outlined in Scheme 8, FIG. 21. Porphyrin Zn-14 bears a vinyl group for surface attachment, a pyridyl group for subsequent elaboration, and two p-tolyl groups. Porphyrin Zn-14 is a control compound that bears a pyridyl group and three phenyl groups. Attempts to diacylate 5-(4-pyridyl)dipyrromethane (16d) were unsuccessful. Accordingly, the dipyrromethane representing the distal side of the porphyrin was subjected to diacylation. The diacyldipyrromethane-tin complex 20 was described above, and diacyldipyrromethane-tin complex 21 (Liu et al. (2005) *Chem. Mater.*, 17: 3728-3742) has been reported previously. Reduction of 20 or 21 with NaBH$_4$ afforded the corresponding dipyrromethane-dicarbinol, which upon reaction with the pyridyldipyrromethane 16d in CH$_2$Cl$_2$ containing Yb(OTf)$_3$, oxidation with DDQ, and zinc metalation afforded Zn-14 or Zn-22, respectively. It is noteworthy that the free base analogue (22) (Tomizaki et al. (2003) *J. Org., Chem.* 68: 8199-8207; Gryko and Lindsey (2000) *J. Org. Chem.*, 65: 2249-2252) and Zn-22 (Barton et al. (2000) *J. Chem. Soc., Dalton Trans.*, 3170-3175) were previously prepared by different routes.

Part II. Porphyrins for In-Situ Assembly.

A. Porphyrins for In-Situ Dyad Assembly.

Two porphyrins were designed for studies of in situ dyad formation, where the porphyrin would be attached to the distal functional group of the base porphyrin. Each porphyrin bears one reactive group and three nonlinking substituents. A porphyrin containing an alcohol group can be used for in situ reaction with a porphyrin containing a pentafluorophenyl or bromo substituent (Zn-2 or Zn-4 respectively), to form ether-linked dyads on the surface. A porphyrin bearing an isothiocyanatophenyl group can be used for in situ reaction with an aminoporphyrin (Zn-10 or Zn-11) to form thiourea-linked dyads on the surface.

We have prepared several porphyrins each bearing a single alcohol substituent (Zn-23 (Yasseri et al. (2004) *J. Am. Chem. Soc.*, 126: 15603-15612; Erratum: *J. Am. Chem. Soc.*, 127: 9308), Zn-24 (Balakumar et al. (2004) *J. Org. Chem.* 69: 1435-1443), Zn-25 (Id.), Chart 4 (FIG. 22)). A porphyrin bearing a biphenylmethanol group was attractive given ample distance between the porphyrin and the reactive functional group. The Suzuki coupling reaction of porphyrin Zn-26 (Loewe et al. (2002) *J. Mater. Chem.*, 12: 1530-1552) and 4-(hydroxymethyl)phenylboronic acid (27) was carried out using Pd(PPh$_3$)$_4$ and K$_2$CO$_3$ in toluene/DMF, affording porphyrin-biphenylmethanol Zn-28 (FIG. 23). The conditions employed were typical of those for Suzuki reactions with porphyrins, where limited solubility requires reaction in dilute solution (Yu and Lindsey (2001) *Tetrahedron* 57: 9285-9298; Zhou and Chan (1994) *J. Chem. Soc., Chem. Commun.*, 2493-2494).

Figure 24:
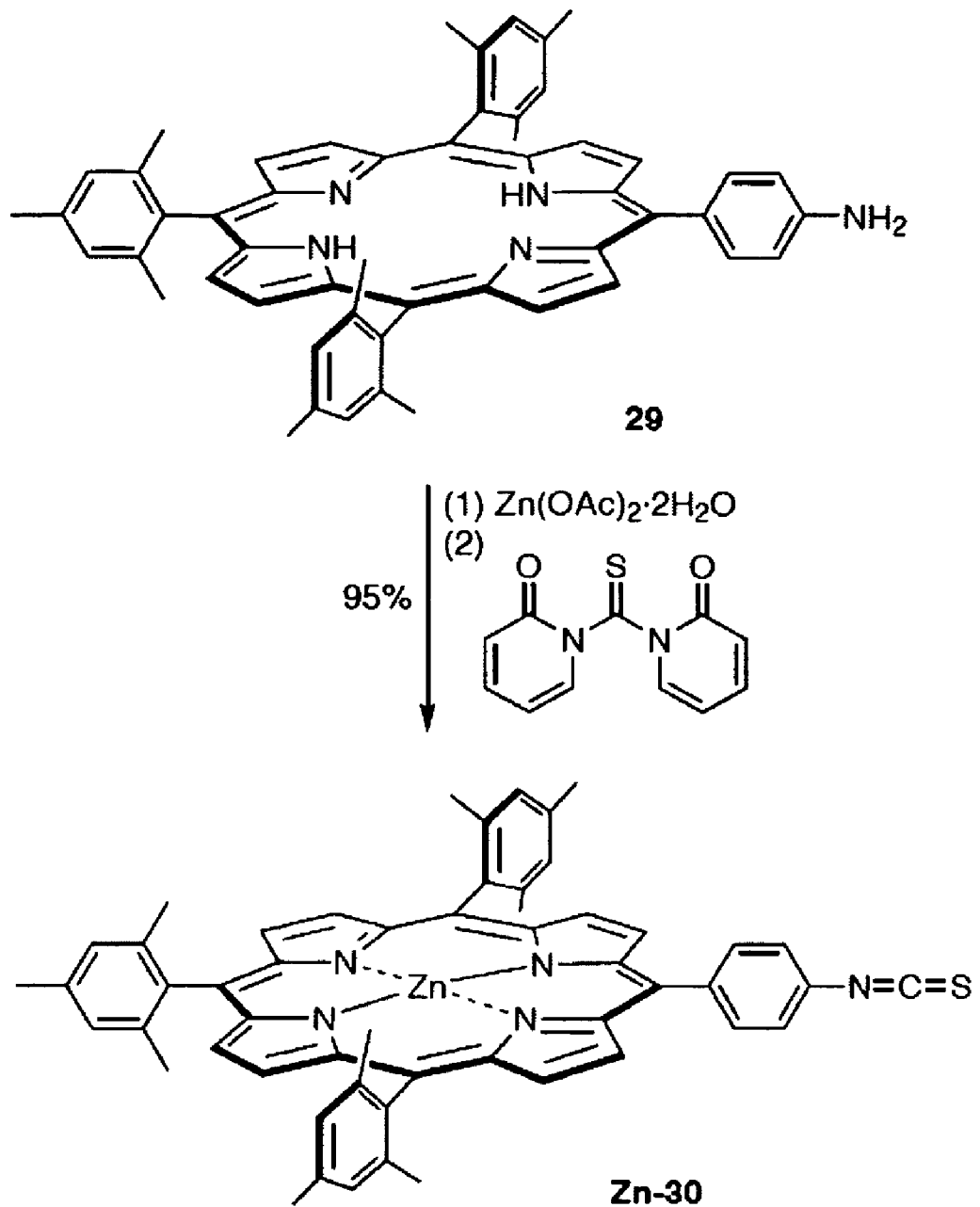
FIG. 24 shows the synthesis of Zn-30.

Porphyrins bearing isothiocyanato groups have been described by Boyle for use in bioconjugation procedures (Sutton et al. (2002) *Bioconjugate Chem.*, 13: 249-263). Porphyrin 29 (Sazanovich et al. (2003) *Inorg. Chem.* 42: 6616-6628) was metalated with zinc, and the zinc chelate was treated with 1,1'-thiocarbonyldi-2(1H)-pyridone (TDP) to give the isothiocyanatoporphyrin Zn-30 (FIG. 24).

B. Porphyrins for In-Situ Oligomer Assembly without Protecting Groups.

Figure 25:
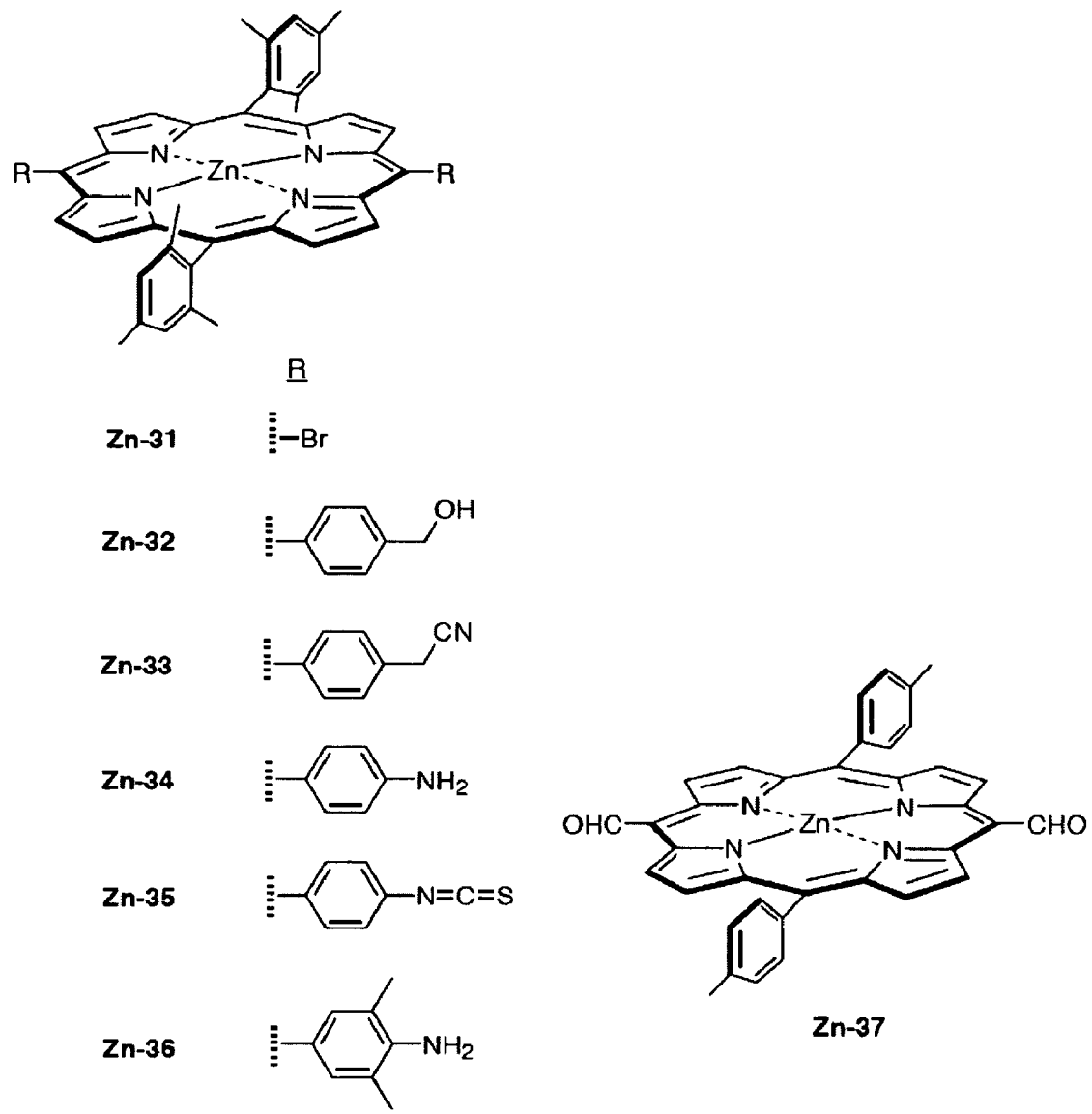
FIG. 25 shows a set of seven trans-$A_2$-porphyrins (Zn-31, Zn-37) suitable for the in situ assembly of oligomers.

The porphyrins for in situ assembly of oligomers bear two identical functional groups on opposing sides of the porphyrin. A set of seven such trans-A$_2$-porphyrins (Zn-31, Zn-37) is shown in FIG. 25. The functional groups were chosen for complementarity to the distal functional group in the set of base porphyrins (Chart 2) (FIG. 13). The syntheses of trans-A$_2$-porphyrins Zn31, Zn-36 were initiated by condensation of an aldehyde and 5-dipyrromethane that is resistant to acidolysis (e.g., 5-mesityldipyrromethane (16h) or dipyrromethane itself) (Littler et al. (1999) *J. Org. Chem.*, 64: 2864-2872). The trans-A$_2$-porphyrin Zn-37 relied on self-condensation of an acetal-substituted dipyrromethane-carbinol (Balakumar et al. (2004) *J. Org. Chem.* 69: 5112-5115). The syntheses are described in more detail below.

Figure 26:
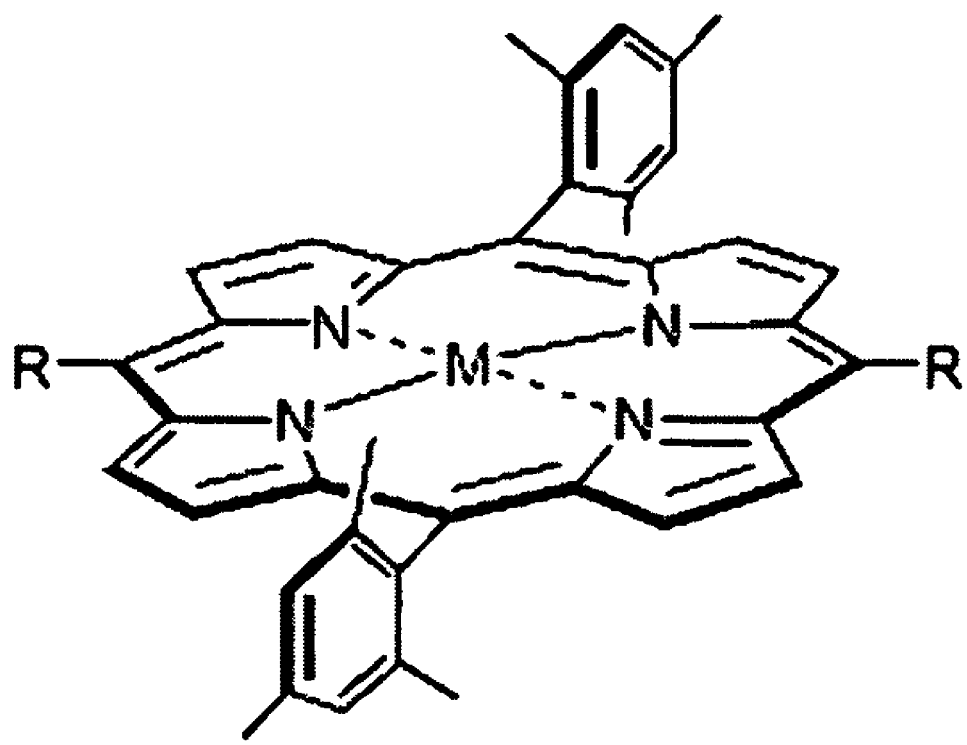
FIG. 26 shows the synthesis of dibromoporphyrin Zn-31.

The synthesis of dibromoporphyrin Zn-31 is shown in FIG. 26. Treatment of porphyrin 38 (available by condensation of dipyrromethane and mesitaldehyde)with NBS afforded crude dibromoporphyrin 31 (Yu et al. (2003) *Inorg. Chem.*, 42: 6629-6647), which was directly metalated with Zn(OAc) 2.2H$_2$O to give Zn-31 (71% yield from 38).

Figure 27:
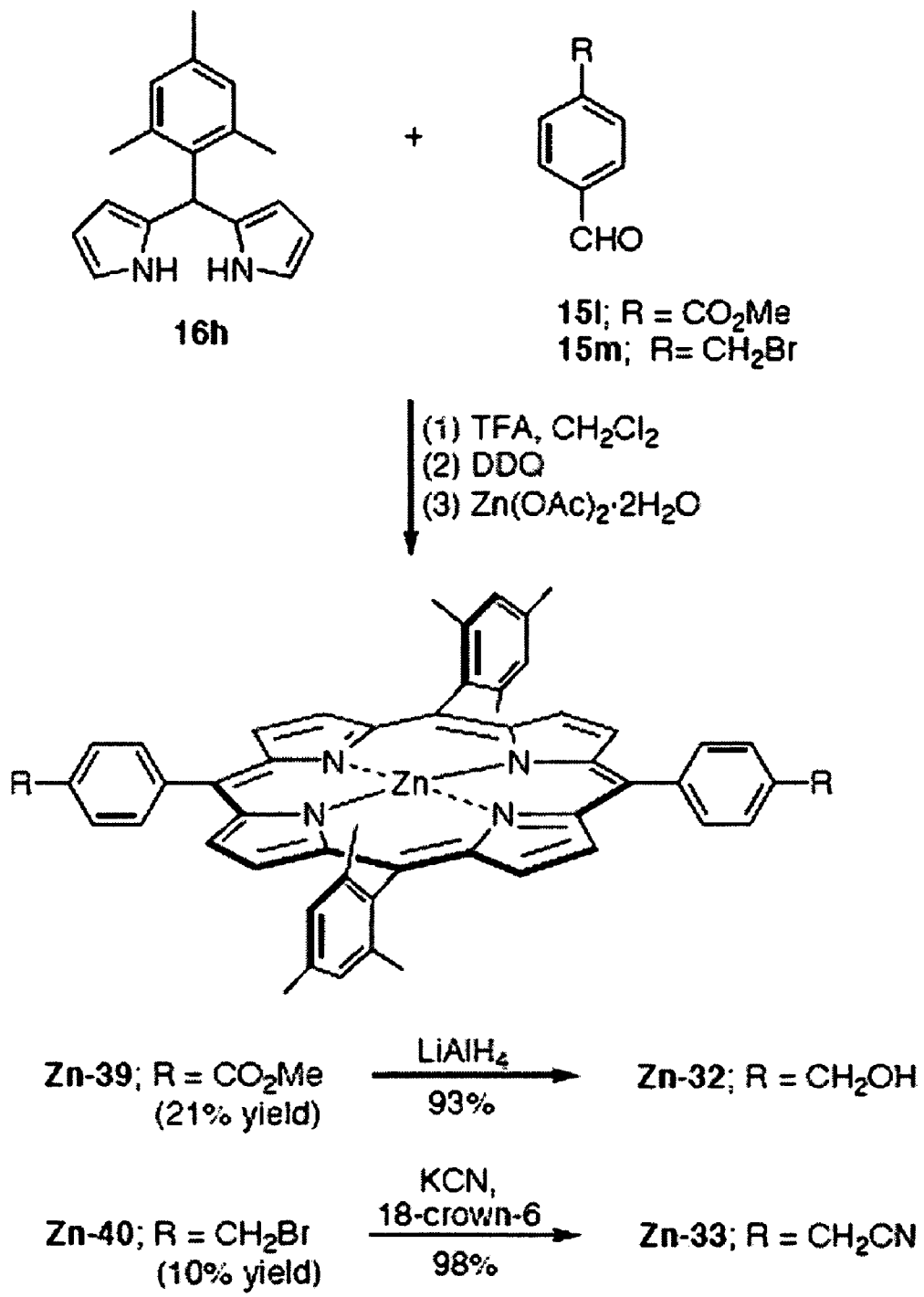
FIG. 27 shows Scheme 9 for the synthesis of bis(hydroxymethyl)porphyrin Zn-32 and bis(cyanomethyl)porphyrin Zn-33 in Example 2.

The synthesis of bis(hydroxymethyl)porphyrin Zn-32 and bis(cyanomethyl)porphyrin Zn-33 is shown in Scheme 9 (FIG. 27). The condensation of 5-mesityldipyrromethane (15h) and aldehyde 15l or 15m (Wen and Schlenoff (1997) *J. Am. Chem. Soc.*, 119: 7726-7733) in CH$_2$Cl$_2$ containing TFA followed by oxidation with DDQ and zinc insertion led to Zn-39 or Zn-40 in 21% or 10% yield, respectively. Free base porphyrin 39 is known (Carcel et al. (2004) *J. Org. Chem.* 69:

6739-6750). Porphyrin Zn-40 has been prepared previously in higher yield using different reaction conditions (Jiang and Jones (1997) *Macromolecules* 30: 5575-5581). Reaction of Zn-39 with LiAlH$_4$ gave Zn-32 in 93% yield. Treatment of Zn-40 with KCN in the presence of 18-crown-6 (Cook et al. (1974) *J. Org. Chem.*, 39: 3416-3418) afforded Zn-33 in 98% yield.

Figure 28:
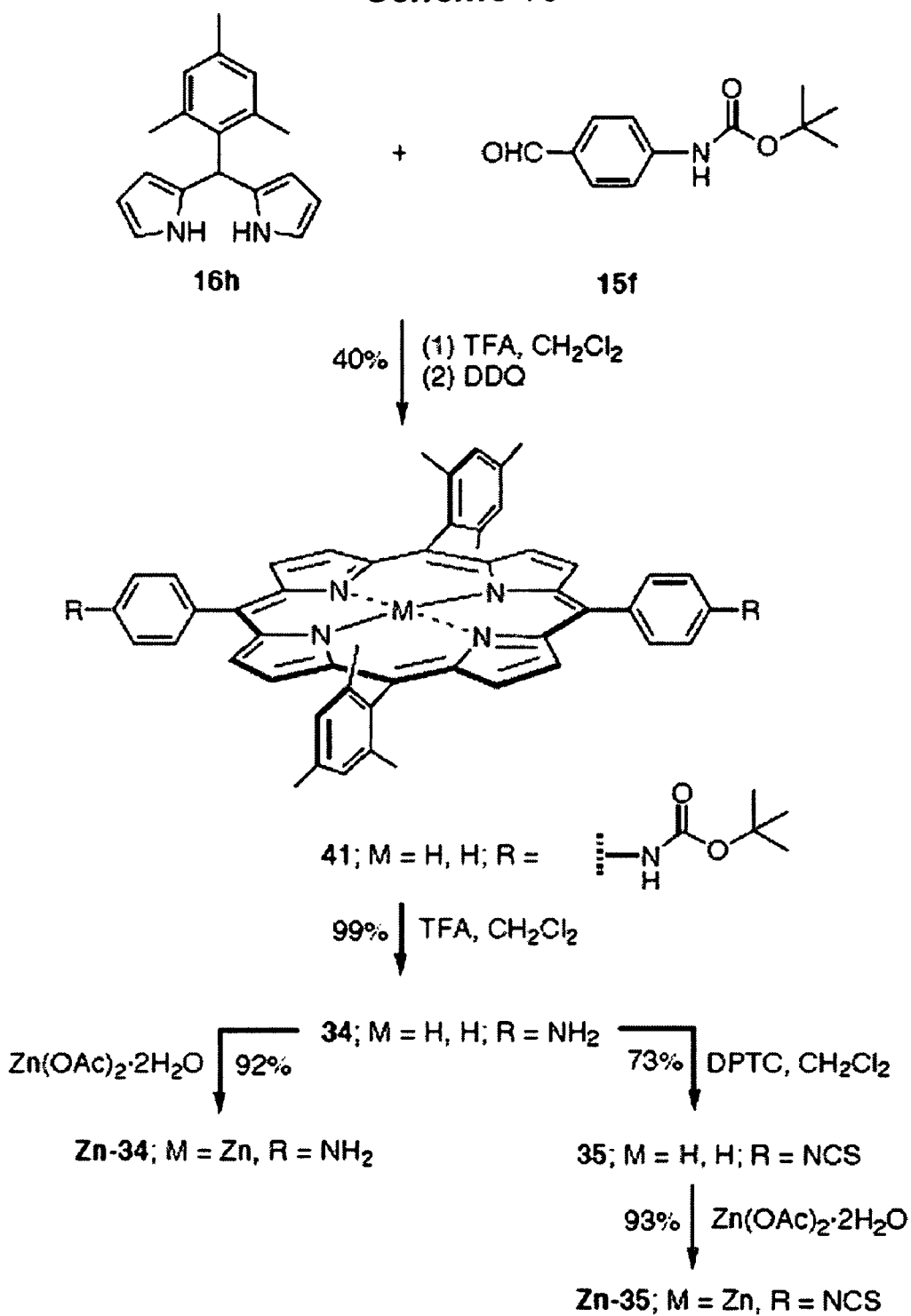
FIG. 28 shows Scheme 10 for the synthesis of diaminoporphyrin Zn-34 and diisothiocyanatoporphyrin Zn-35 in Example 2.

The synthesis of diaminoporphyrin Zn-34 and diisothiocyanatoporphyrin Zn-35 is outlined in Scheme 10 (FIG. 28). The condensation of 5-mesityldipyrromethane with 15f using TFA catalysis followed by oxidation with DDQ afforded 41 in 40% yield. Treatment of this BOC protected free base porphyrin with TFA afforded free base diaminoporphyrin 34 in quantitative fashion. Zinc metalation of the latter afforded Zn-34 in 92% yield. The isothiocyanato group was introduced to porphyrin 34 using a different reagent than employed for porphyrin 29. Following an older literature procedure (Kim and Yi (1985) *Tetrahedron Lett.*, 26: 1661-1664; Han et al. (1996) *Langmuir* 12: 5742-5744), treatment of 34 with di-2-pyridyl thiocarbonate (DPTC) gave diisothiocyanatoporphyrin 35 in 73% yield. Zinc metalation of 35 afforded Zn-35 in 93% yield.

Figure 29:
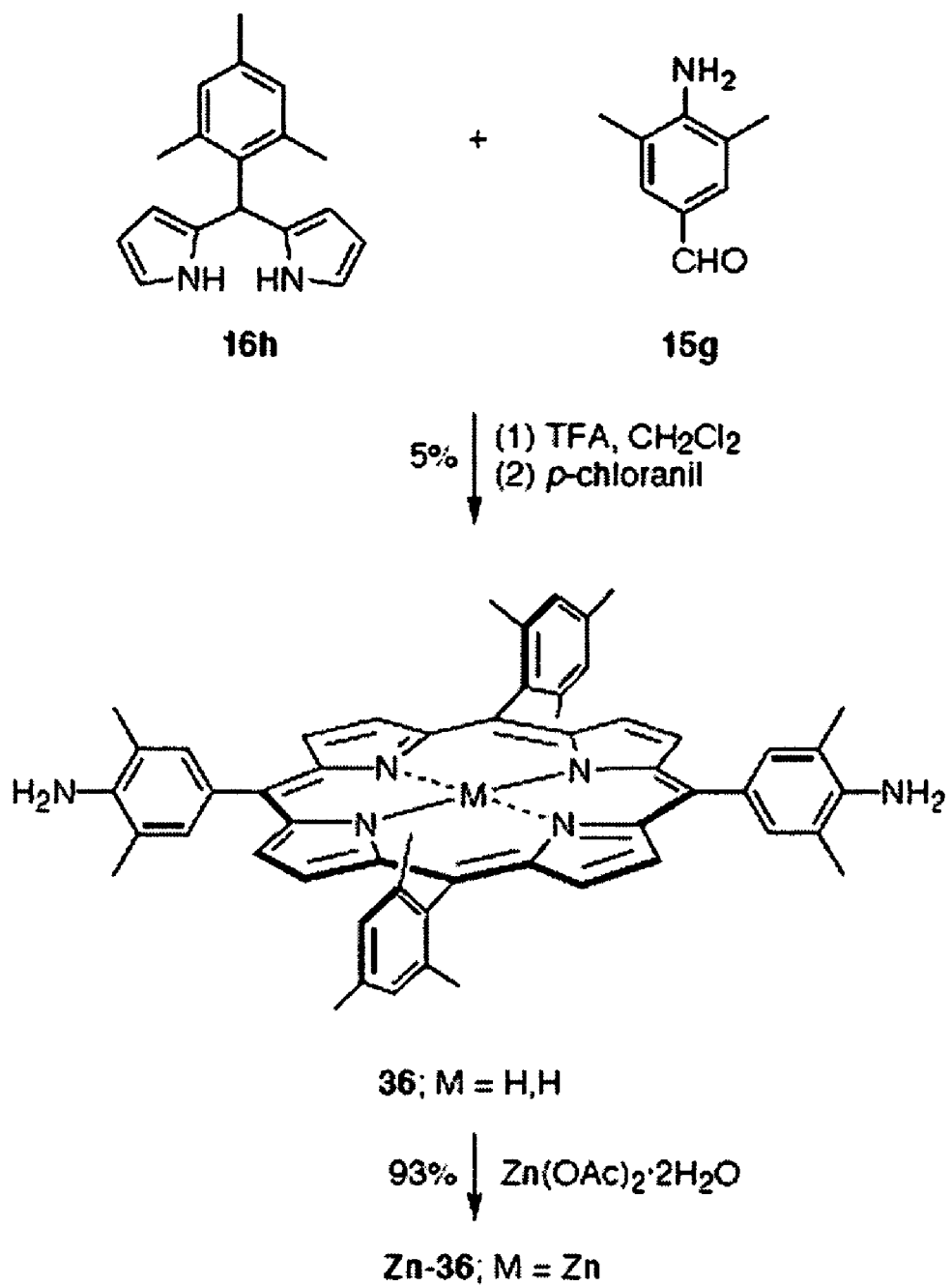
FIG. 29 shows Scheme 11 for the synthesis of a sterically hindered diaminoporphyrin (Zn-36) in Example 2.

The synthesis of a sterically hindered diaminoporphyrin (Zn-36) is shown in Scheme 11 (FIG. 29). The condensation of dipyrromethane 16h and aldehyde 15g (Lal et al. (1984) *Tetrahedron Lett.* 25, 2901-2904) in CH$_2$Cl$_2$ containing TFA followed by oxidation with p-chloranil led to 36 in 5% yield. Zinc metalation of 36 afforded Zn-36 in 93% yield.

Figure 30:
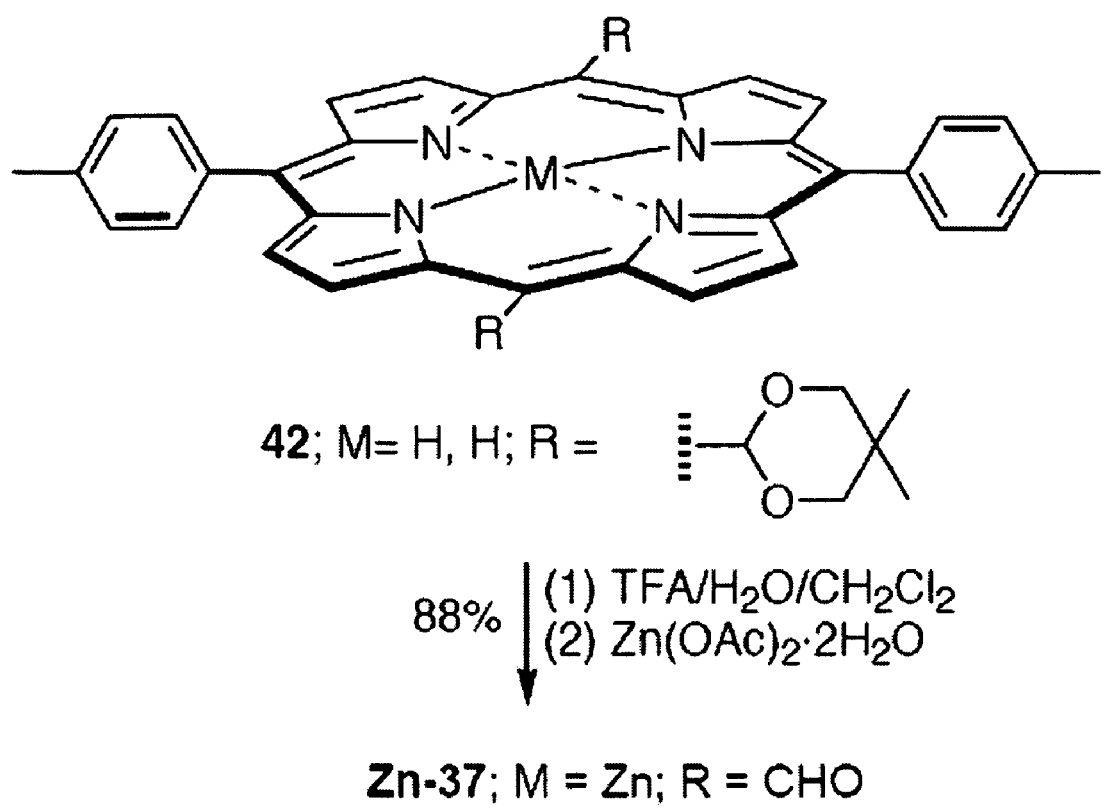
FIG. 30 shows equation 4 for the synthesis of diformylporphyrin Zn-37 in Example 2.

The synthesis of diformylporphyrin Zn-37 is shown in Eqation 4 (FIG. 30). Porphyrin 42 was obtained by self-condensation of the carbinol derived from a 1-acyldipyrromethane bearing a 5-acetal substituent (Balakumar et al. (2004) *J. Org. Chem.* 69: 5112-5115). Hydrolysis of the two acetal groups of 42 with CH$_2$Cl$_2$/TFA/H$_2$O gave crude 5,15-diformylporphyrin 37 (Id.) which upon metalation gave Zn-37 (88% yield from 42).

Figure 31:
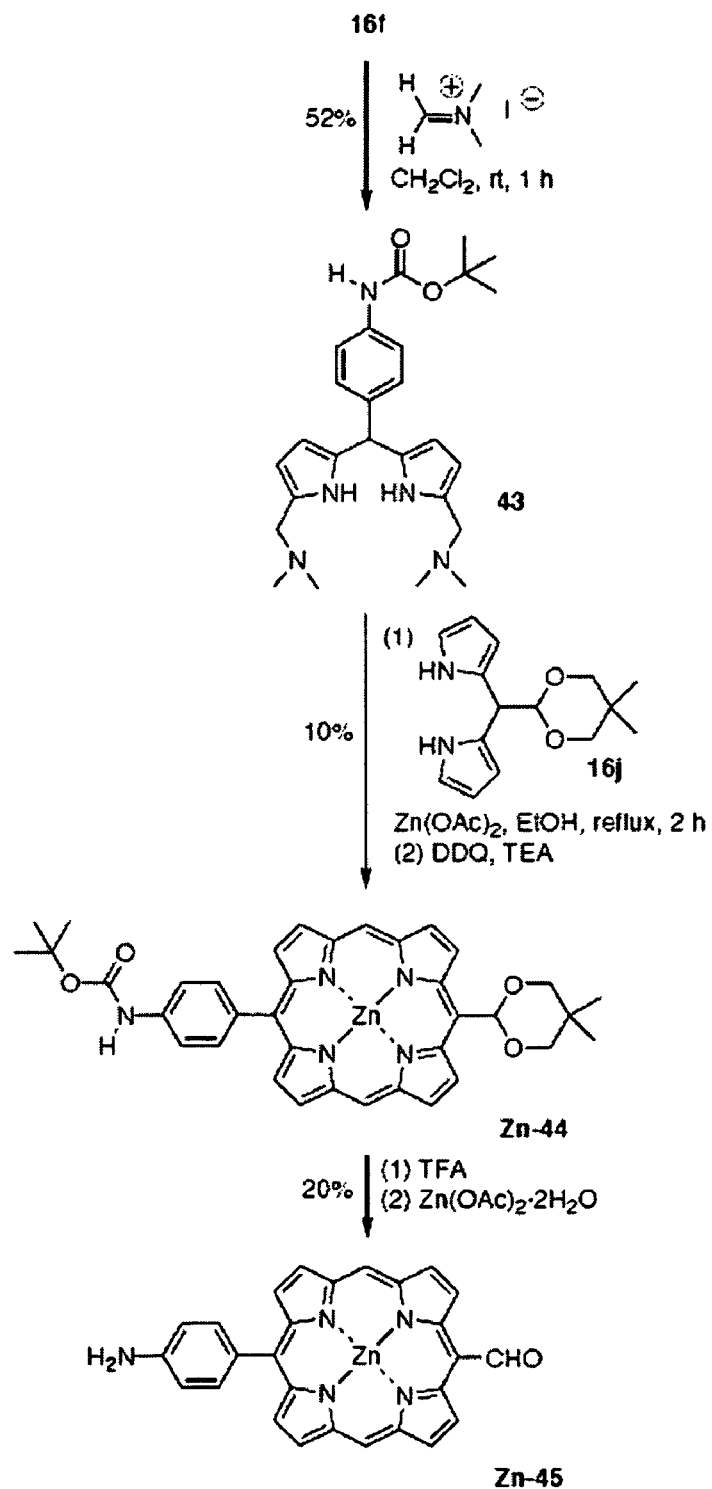
FIG. 31 shows Scheme 12 for the synthesis of Zn-44 and Zn45 in Example 2.

A porphyrin containing one amino group and one formyl substituent was prepared for examination of in situ polymerization as a complement to in situ stepwise growth. A new synthesis of trans-AB-porphyrins was employed (Fan et al. (2005) *Tetrahedron*, 61: 10291-10302). Reaction of 16f with Eschenmoser's reagent at room temperature followed by hydrolysis with aqueous NaHCO$_3$ gave the 1,9-bis(N,N-dimethylaminomethyl)dipyrromethane (43) in 52% yield (Scheme 12, FIG. 31). Condensation of 43 and 16j in ethanol containing Zn(OAc)$_2$ under reflux for 2 h followed by oxidation with DDQ afforded the porphyrin Zn-44 in 10% yield. Treatment of Zn-44 with TFA and subsequent zinc metalation afforded Zn-45 in 20% yield. Porphyrin Zn-45 was unstable on chromatography and was isolated in ~95% purity in low yield.

Part III. Physical Studies.

A. Surface Coverage, Adsorption Geometry, and Binding Motif of the Zn Porphyrin Monolayers.

Figure 32:
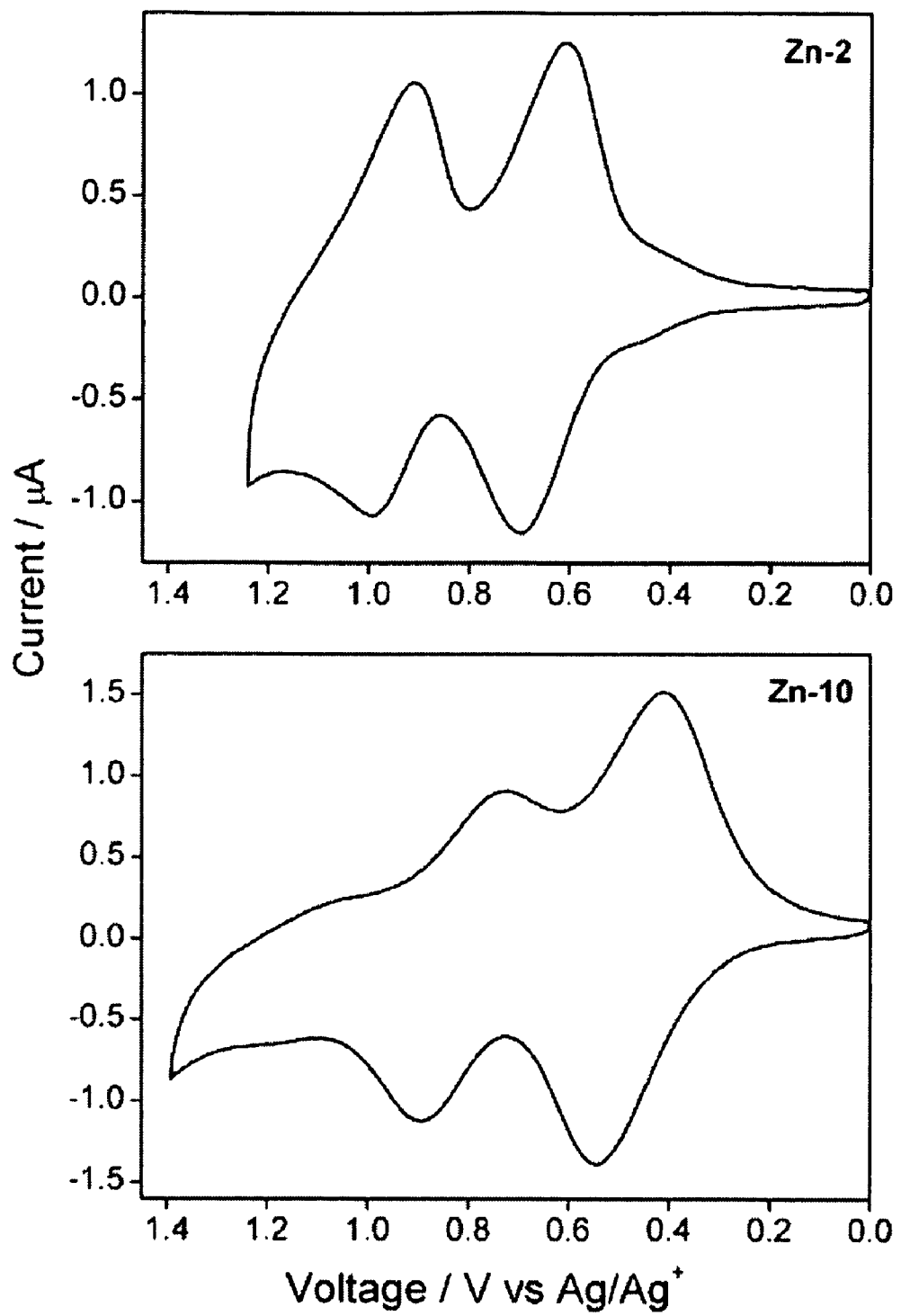
FIG. 32 shows the results of fast scan (100 V s−1) voltammograms of the Zn-2 (top panel) and Zn-10 (bottom panel) monolayers on Si(100).
Figure 33:
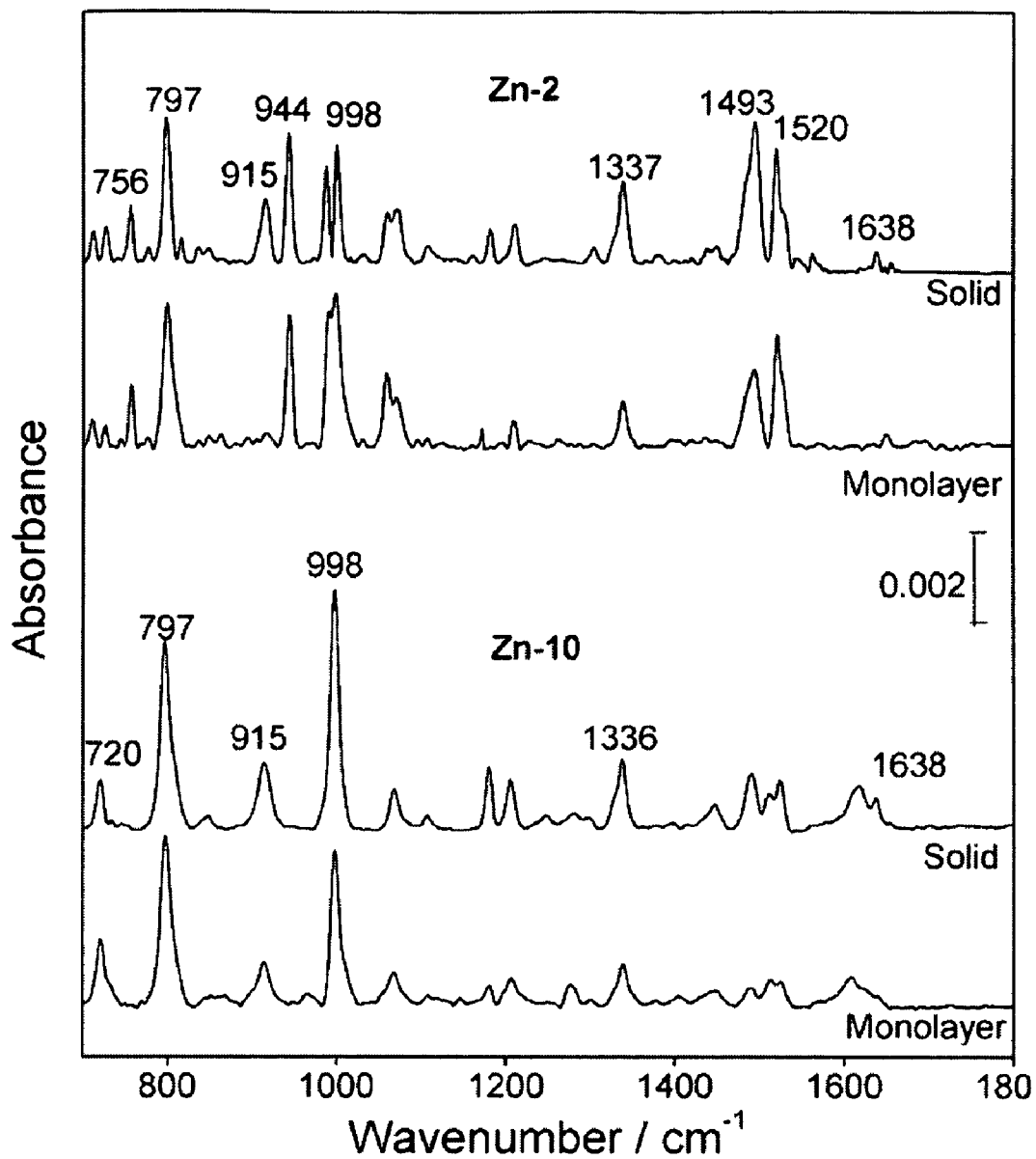
FIG. 33 shows the results of FTIR spectra of solid Zn-2 and Zn-10 in KBr pellets and the corresponding Zn-2 and Zn-10 monolayers on Si(100).
Figure 34:
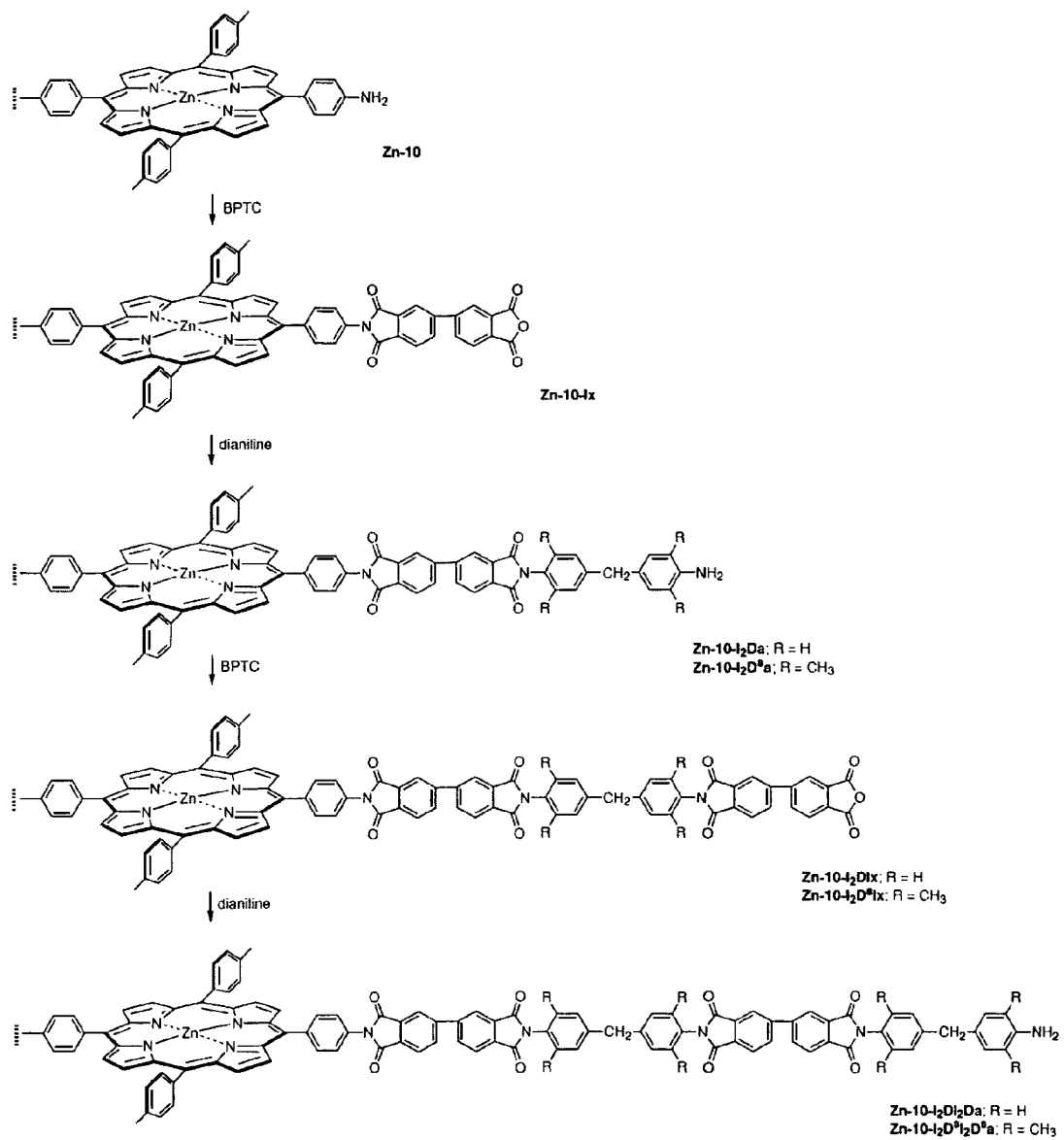
FIG. 34 illustrates Scheme 13 in Example 2.

Prior to investigating the suitability of the surface-tethered Zn porphyrins as base layers for in situ formation of covalent architectures, the redox characteristics, surface coverage, adsorption geometry, and binding motif of each porphyrin (Zn-2-Zn14, FIGS. 13 and 14) were examined on Si(100). The surface coverage was evaluated using electrochemical methods; the adsorption geometry and binding motif were examined using FTIR spectroscopy. Voltammetric and FTIR data for two representative molecules, and are shown in FIGS. 32 and 33. A summary of the redox potentials, surface coverage, adsorption geometry (expressed as the average tilt angle with respect to the surface normal), and binding motif of each molecule is provided in Table 3.

TABLE 3

Redox Potentials,[a] Surface Coverage Values,[b] Average Tilt Angles,[c] and Binding Motif[d] for the Zn-Porphyrin Monolayers on Si(100).

| | $E^{0/+1}$ (V) | | $E^{+1/+2}$ (V) | | Surface Coverage $10^{-10}$ mol cm$^{-2}$ | Tilt (deg) | Binding Motif |
|---|---|---|---|---|---|---|---|
| | Soln | monolayer | Soln | Mono-layer | | | |
| Zn-2 | 0.61 | 0.64 | 0.90 | 0.95 | 2.1 | 36 | T |
| Zn-3 | 0.56 | 0.59 | 0.88 | 0.99 | 1.8 | 38 | T |
| Zn-4 | 0.54 | 0.56 | 0.87 | 0.90 | 1.7 | 39 | T or Y |
| Zn-5 | 0.59 | 0.66 | 0.86 | 0.99 | 1.8 | 37 | T |
| Zn-6[e] | 0.53 | 0.55 | 0.84 | 0.88 | 1.7 | 39 | T |
| Zn-7 | 0.54 | 0.62 | 0.86 | 0.90 | 0.4 | 37 | T or Y |
| Zn-8 | 0.54 | 0.55 | 0.85 | 0.87 | 2.2 | 38 | T or Y |
| Zn-9 | 0.55 | 0.65 | 0.87 | 0.94 | 2.1 | 41 | T or Y |
| Zn-10[f] | 0.52 | 0.58 | 0.80 | 0.88 | 2.1 | 38 | T or Y |
| Zn-11[g] | 0.55 | 0.58 | 0.87 | 0.92 | 2.0 | 37 | T or Y |
| Zn-12 | 0.52 | 0.55 | 0.85 | 0.93 | 1.4 | 36 | T or Y |
| Zn-13[h] | 0.48 | 0.52 | 0.73 | 0.80 | 1.3 | 41 | V or Y |
| Zn-14 | 0.52 | 0.58 | 0.89 | 0.94 | 0.6 | 40 | V or Y |

[a]Solution potentials, obtained in CH$_2$Cl$_2$ containing 0.1M n-Bu$_4$NPF$_6$; scan rate 0.1 V s$^{-1}$. Values are referenced vs Ag/Ag$^+$; FeCp$_2$/FeCp$_2^+$ 0.20 V. Monolayer potentials, obtained in propylene carbonate containing 1.0M nBu$_4$NPF$_6$; scan rate 100 Vs$^{-1}$.
[b]Porphyrin surface concentration calculated from the integrated area of the E$^{0/+1}$ and E$^{+1/+2}$ anodic waves and using the geometrical area of the microelectrode ($10^{-4}$ cm$^2$).
[c]Average tilt angle determined on the basis of the intensity ratio of the in-plane pyrrole breathing (998 cm$^{-1}$) and the out-of-plane β-pyrrole hydrogen deformation (797 cm$^{-1}$) bands in the IR spectra.
[d]Binding motif: T = tripod; V = vinyl; Y = functional group (Charts 2 and 3, FIGS. 13 and 14, respectively).
[e]A third redox wave is observed at ~1.18 V in solution that is absent in the monolayer.
[f]A third redox wave is observed at ~1.17 V for both solution and monolayer.
[g]A third redox wave is observed at ~1.35 V for both solution and monolayer.
[h]Two additional redox waves are observed at ~1.18 V and ~1.30 V for both solution and monolayer.

The general electrochemical and vibrational characteristics of the Zn porphyrin monolayers are similar to those we have previously reported for other carbon-tethered porphyrin monolayers on Si(100) (Wei et al. (2005) *J. Phys. Chem. B* 109: 6323-6330; Thamyongkit et al. (2006) *J. Org. Chem.* 71: 903-910; Padmaja et al. (2005) *J. Org. Chem.* 70: 7972-7978) and will not be elaborated herein. Instead, we summarize the general characteristics and focus on the key features of the molecules that are germane to their suitability for in situ patterning. These characteristics and features are as follows:

(1) All of the Zn porphyrins that bear a surface attachment group form good quality monolayers on Si(100) as evidenced by both their voltammetric and vibrational signatures. The surface coverage of all the Zn porphyrins (with the exception of Zn-7 and Zn-14) are in the range of 1-2×10$^{-10}$ mol cm$^{-2}$, which is comparable to that of other carbon-tethered Zn porphyrins on Si(100) (Id.). The surface coverages for Zn-7 and Zn-14 both of which are functionalized with pyridine, are 3-4-fold lower; we have no explanation for this observation.

(2) The adsorption geometry of all the Zn porphyrins are similar to one another and similar to those of other carbon-tethered Zn porphyrins on Si(100) as determined by their vibrational signatures (Id.). In particular, the average tilt angle of the porphyrin plane with respect to the surface normal is ~38° for all the molecules.

(3) For a number of the Zn porphyrins, it appears that binding can occur either via the targeted triallyl, (T) (or vinyl (V)) group, or the functional group (Y); only Zn-2, Zn-3, Zn-5, and Zn-6 (and Zn-12, for which Y is also a T group) bind exclusively via the targeted alkenyl group. This assessment is based on features observed in the FTIR spectra as is illustrated by the spectra shown for Zn-2 versus Zn-10 in FIG. 33. In particular, the spectra of the Zn-2 and Zn-10 solids exhibit bands characteristic of the alkenyl group near 1638 cm$^{-1}$ (C═C stretch) and 917 cm$^{-1}$ (CH deformation). Attachment to the surface via a hydrosilylation reaction eliminates these bands (Id.) as is observed for the Zn-2 (and Zn-3, Zn-5, and Zn-6) monolayer(s). In contrast, bands due to the alkenyl C=C stretch and CH deformation clearly remain in the spectrum of the Zn-10 (and other) monolayer(s), indicating that some of the porphyrins bind via an alternative motif, namely the functional group. The relative number of molecules that bind via the alkenyl versus functional group cannot be readily determined from the FTIR data owing to the fact that the intensities of the vibrational bands for the monolayer are sensitive to the orientation of the transition dipoles with respect to the surface as well as the relative number of dipoles. For example, the strong residual alkenyl features that appear in the spectrum of the Zn-10 monolayer would nominally suggest that the majority of the molecules bind via the NH group. However, the in situ patterning studies described below show that this cannot be the case (vide infra).

(4) Most of the functional groups (that do not bind to the surface) remain intact under the high temperature conditions used for surface attachment, as is evidenced by their vibrational signatures in the spectrum of the monolayer (e.g., C—F stretch at 944 $cm^{-1}$ for Zn-2; C≡N stretch for Zn-8 at 2213 $cm^{-1}$). One clear exception is the carboxyl functional group. The spectra of the monolayers of Zn-5, Zn-6, and Zn-9 show no evidence of the characteristic C=O stretches (~1700 $cm^{-1}$) that are observed for these molecules in the solids.

The observation that the functional groups of many of the Zn porphyrins appear to bind and/or react with the surface limits the choices for the base porphyrins in the studies of in situ formation of vertical architectures. Indeed, the only porphyrins that bind exclusively via the alkenyl group and exhibit thermally stable functional groups are Zn-2 and Zn-3. From this pair, Zn-2 was selected for studies of in situ porphyrin dyad formation owing to the fact that the p-fluorine atom (of the pentafluorophenyl group) should be more reactive than the meso-H atom (of the porphyrin macrocycle) toward ipso substitution. We also chose to investigate dyad formation using Zn-4 which is functionalized with a meso-Br atom, as the base porphyrin. In another series of studies, we investigated in situ formation of polyimides on a porphyrin base layer. These studies used Zn-10 which is functionalized with a p-aminophenyl group. These studies are described in more detail below.

B. In Situ Formation of Zn Porphyrin Dyad Monolayers.

Figure 22:
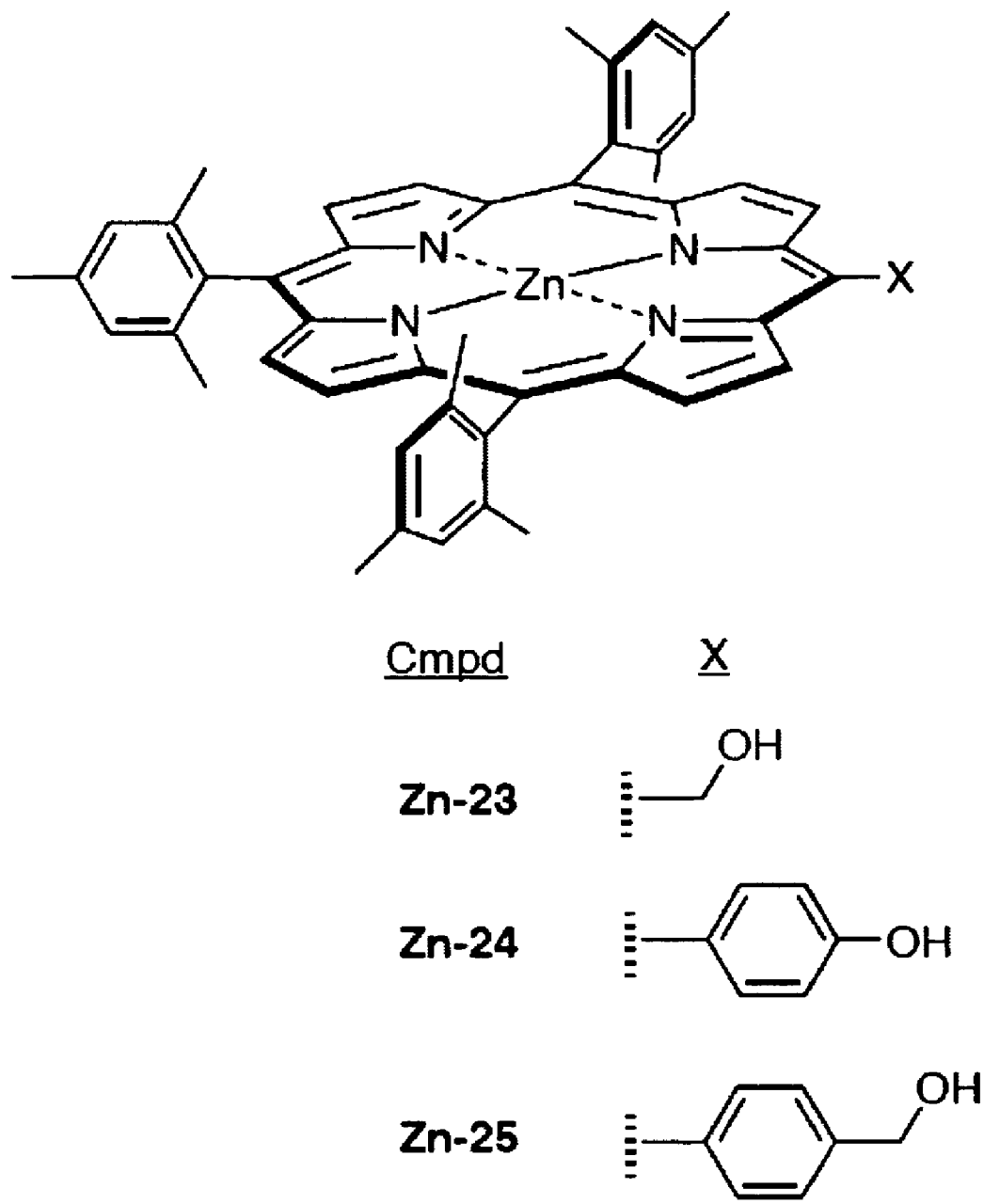
FIG. 22 (chart 4) shows several porphyrins (Zn-23, Zn-24, and Zn-25) each bearing a single alcohol substituent.
Figure 23:
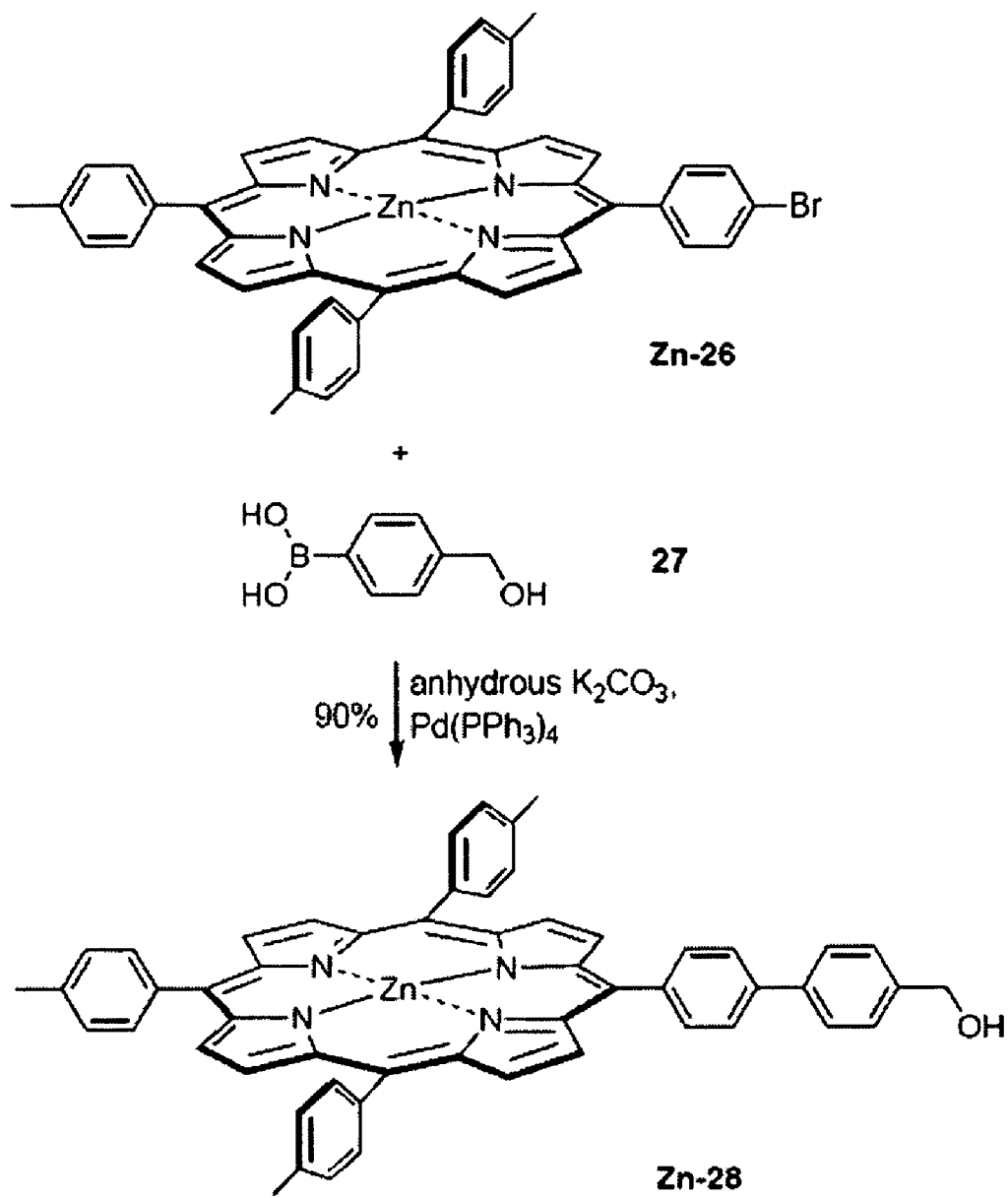
FIG. 23 shows the synthesis of Zn-28.

We attempted to form porphyrin dyads by reacting the surface attached monolayers of Zn-2 and Zn-4 with the three alcohol-functionalized Zn porphyrins shown in Chart 4 (FIG. 22). The porphyrin alcohol was deposited on the monolayer and heated at 400° C. (see Experimental Section for details). The samples were then interrogated using both voltammetry and FTIR spectroscopy. The voltammetric signatures showed modest increases in charge density (20-40%) depending on the choice of porphyrin base layer and alcohol. In no case was dyad formation quantitative. The changes in the FTIR spectra were less apparent and no signature bands could be identified that are characteristic of formation of an ether linkage between the two porphyrins. However, these bands would be difficult to detect because they would fall in a spectrally congested region. We have not yet attempted to optimize the conditions for in situ dyad formation owing to the fact that this will require exploration of a relatively large parameter space.

C. In situ Formation of Polyimide Functionalized Zn Porphyrin Monolayers.

We examined in situ formation of polyimides by reacting the surface-attached Zn-10 monolayers with successive applications of 3,3',4,4'-biphenyltetracarboxylic dianhydride (BPTC) and either 4,4'methylenedianiline (MDA) or 4,4'-methylene-bis(2,6-dimethylaniline) (MMDA). The porphyrin dianhydride and dianiline ("imide reagents") were successively deposited on the monolayer and heated at 280° C. (see Experimental Section for details). The samples were then interrogated using both voltammetry and FTIR spectroscopy. The voltammetric and FTIR data for the stepwise addition of one through four aliquots of imide reagents are shown in FIGS. 3 and 4, respectively. The structures of the molecules that would result from the imide-formation reaction are shown in Scheme 13.

Figure 35:
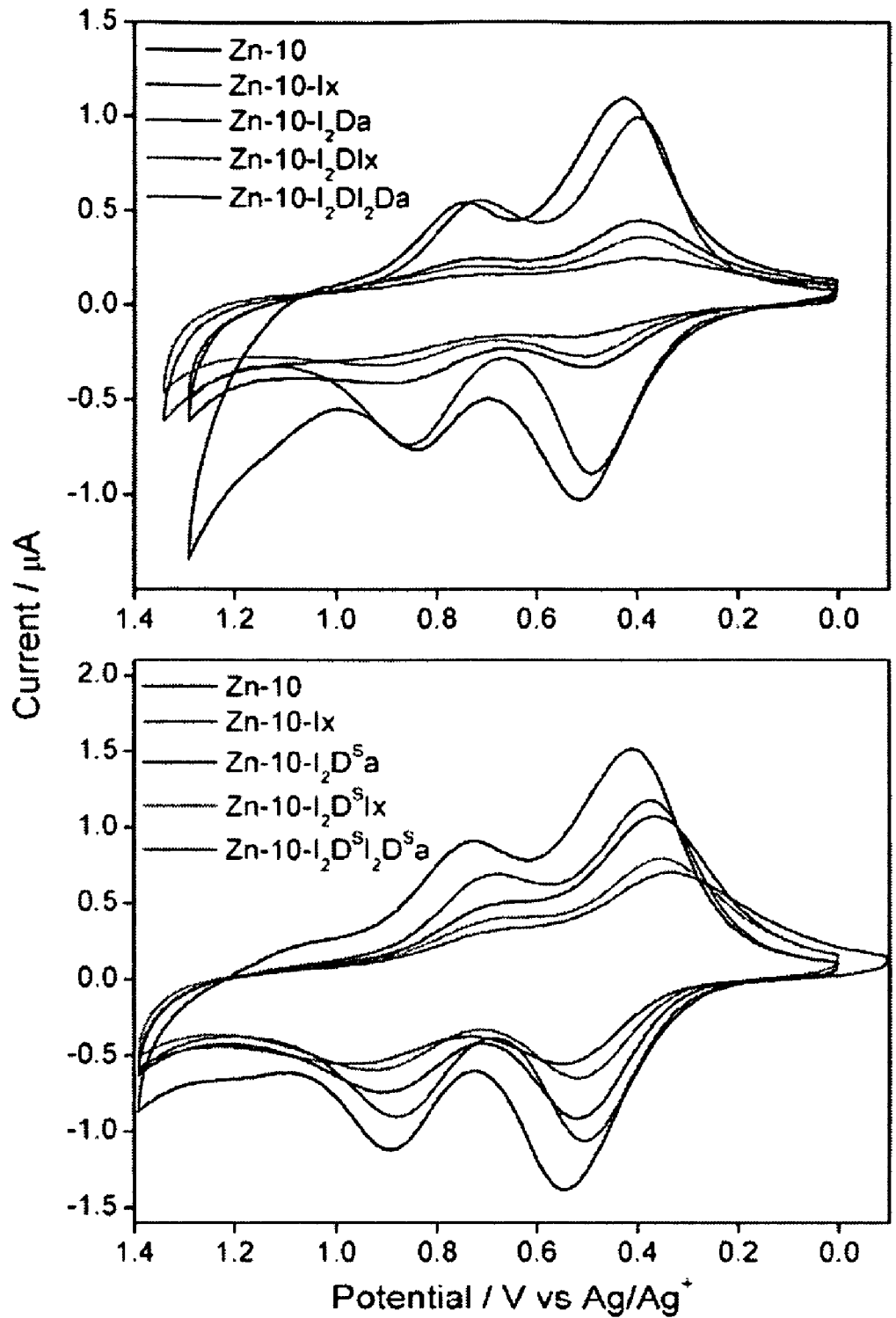
FIG. 35 shows fast scan (100 V s−1) voltammograms of the Zn-10 monolayers on Si(100) before and after successive stepwise additions of BPTC and MDA (top panel) or MMDA (bottom panel).

Inspection of the voltammetric data shown in FIG. 35 shows that subjecting the monolayer to BPTC and MDA/MMDA results in an apparent successive loss of signal. The signal loss is particularly large upon addition of DMA to the BPTC-modified monolayer, but far less severe when MMDA is added. The attenuation of the voltammetric signal suggests that the imide reagents may partially compromise the integrity the monolayer. However, these data do not provide structural information.

Figure 36:
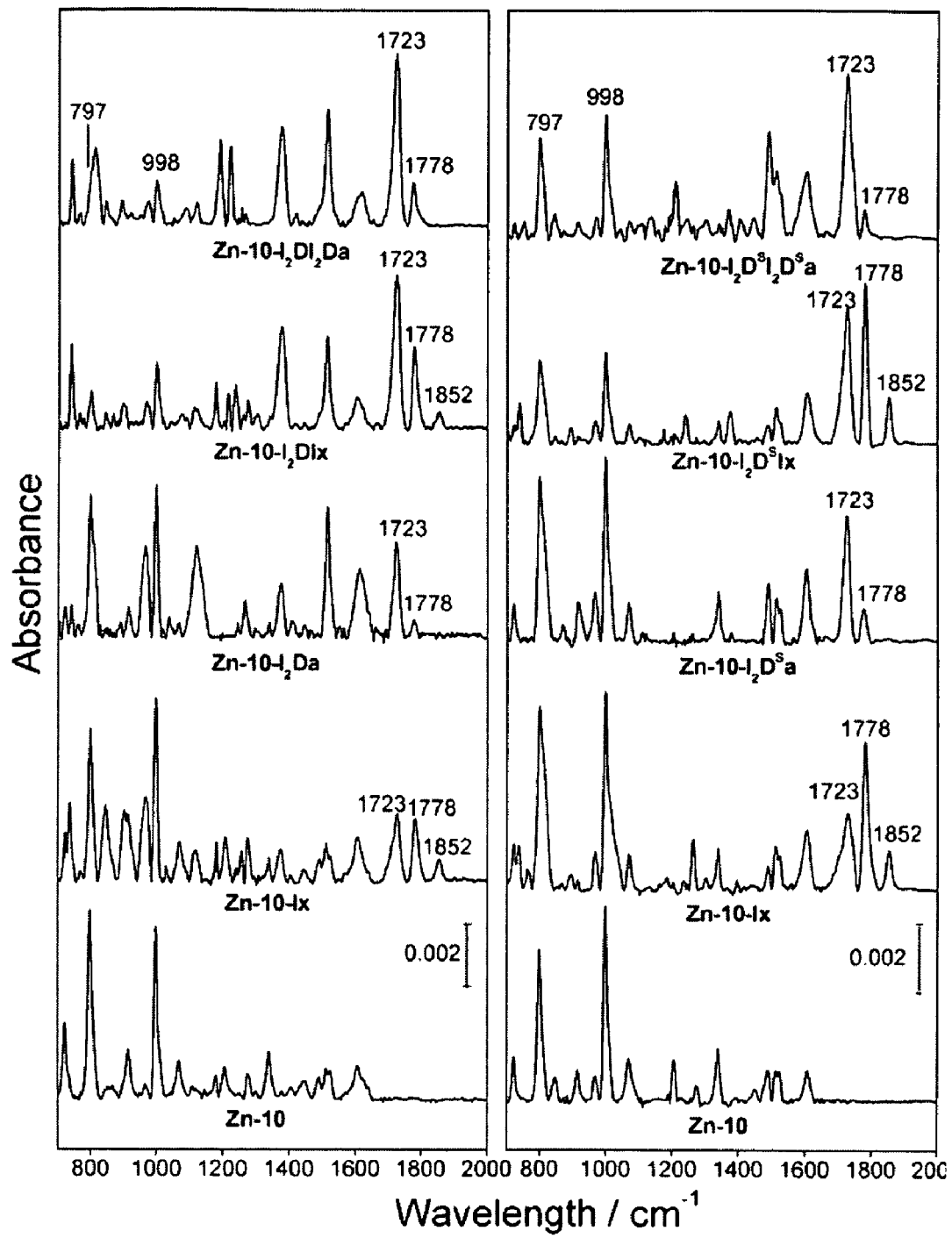
FIG. 36 shows FTIR spectra of the Zn-10 monolayers on Si(100) before and after successive stepwise additions of BPTC and MDA (left panel) or MMDA (right panel).

The FTIR spectra shown in FIG. 36 provide a much clearer picture of the effects of the imide reagents on the porphyrin monolayer and indeed confirm that the imide-formation reaction occurs. Upon addition of the BPTC, the vibrational signatures of the porphyrin remain and a number of new features appear due to the appended BPTC. The key bands are observed at 1723, 1778, and 1852 $cm^{-1}$ all of which are due to C=O stretches of the anhydride and/or imide. The 1853 $cm^{-1}$ band is due to the asymmetric C=O stretch of the anhydride; the 1778 $cm^{-1}$ band is due to primarily to the symmetric C=O stretch of the anhydride, which overlaps the weaker asymmetric C=O stretch of the imide; the 1723 $cm^{-1}$ band is due to the symmetric C=O stretch of the imide. This latter feature provides direct evidence that a significant number of Zn-10 molecules bind to the surface via the triallyl group, leaving the porphyrin amino group free to couple to one end of the BPTC molecule. [Neat BPTC only exhibits bands at 1852 $cm^{-1}$ due to the anhydride.] Upon addition of MDA/MMDA, the 1853 $cm^{-1}$ band of the anhydride disappears, the intensity of the 1778 $cm^{-1}$ band is greatly attenuated, and the intensity of the 1723 $cm^{-1}$ band of the imide increases, consistent with loss of anhydride and formation of an additional imide linkage. Upon addition of the next aliquots of BPTC and MDA/MMDA the band-intensity pattern exhibits a similar alteration. As the number of imide linkages increase, the imide band at 1723 $cm^{-1}$ gains intensity relative to the porphyrin bands. These data do not, however, address the issue of whether the imide-forming reaction is quantitative. Finally, we note that the successive addition of imide reagents appears to result in an overall loss of the intensity of the porphyrin vibrational bands, qualitatively consistent with the loss of voltammetric data and reinforcing the notion that the conditions used for polyimide formation are not totally benign towards the porphyrin base monolayer. We are continuing to investigate strategies for mitigating the deleterious processes.

Outlook

A major impediment to the development of hybrid molecular-semiconductor devices resides in the identification of molecular chemistry that is compatible with the daunting temperatures encountered in semiconductor fabrication (up to 400° C.) and operation (up to 140° C.). Our prior work has established that (1) porphyrins bearing appropriate tethers undergo attachment to surfaces at elevated temperatures (200-400° C.), (2) operate at elevated temperatures (100° C.), and (3) can be cycled repeatedly ($>10^{10}$ cycles) (Liu et al. (2003) *Science* 302: 1543-1545). Little precedent is available, however, concerning chemistry suitable for in situ assembly of covalently linked molecular architectures on an electroactive surface, particularly where the first step of the assembly process requires a high-temperature attachment procedure.

The library of porphyrins prepared herein has enabled a survey of a variety of chemistries for in situ assembly of molecular architectures on an electroactive surface. More extensive studies and examination of reaction conditions with this library is now possible. A chief finding is that multads of porphyrinic macrocycles (and/or spacers of various composition) can be assembled in a stepwise manner without use of protecting groups. Such an assembly process has heretofore required the use of protecting groups, wherein one cycle of coupling has entailed three reactions: protecting group introduction, coupling, and protecting group removal. The avoidance of protecting groups provides a more efficient process, and lessens the burden of identifying suitable conditions for protecting group removal that are compatible with the components in the nascent molecular architecture as well as the underlying substrate.

The current studies further demonstrate that among the various chemistries explored for covalent multad assembly, the imide forming reaction is particularly attractive. Coupling to the surface-tethered molecule is readily achieved using this reaction, and the stepwise growth of the overlayers is conveniently monitored via the IR signatures of the building blocks. Polyimides are well established as polymers with high thermal stability and a wide range of applications. This reaction can be used as a means of preparing multiporphyrin assemblies. In this approach, a diamino-functionalized porphyrin, such as Zn-34 or Zn-36 is substituted for MDA/MMDA while BPTC is retained as the dianhydride.

EXPERIMENTAL SECTION

A. General Procedures for Porphyrin Formation

5-[4-(4-Allylhepta-1,6-dien-4-yl)phenyl]-10,20-di-p-tolyl-15-(pentafluorophenyl)porphyrin (2)

Following a standard procedure (Rao et al. (2000) *J. Org. Chem.* 65: 7323-7344) with improved acid catalysis conditions (Geier et al. (2001) *J. Porphyrins Phthalocyanines* 5: 810-823), a solution of tin complex 17 (108 mg, 0.139 mmol) in dry THF/MeOH (10 mL, 10:1) was treated with $NaBH_4$ (303 mg, 8.01 mmol) in small portions with rapid stirring at room temperature. After 3 h, the reaction was quenched by slow addition of saturated aqueous $NH_4Cl$. The reaction mixture was extracted with $CH_2Cl_2$. The organic solution was dried ($K_2CO_3$) and concentrated, affording 17-diol as a slightly yellow foam-like solid. The freshly prepared 17-diol was condensed with 16b (50 mg, 0.14 mmol) in $CH_2Cl_2$ (55 mL) containing $Yb(OTf)_3$ (109 mg, 0.176 mmol) at room temperature for 30 min. DDQ was added and the reaction mixture was stirred for 1 h. TEA was added. The mixture was filtered through a pad of alumina ($CH_2Cl_2$). The eluted crude product was chromatographed (silica, $CH_2Cl_2$), affording a purple solid (36 mg, 30%): $^1H$ NMR δ-2.55 (s, 2H), 2.74-2.71 (overlapping peaks, 12H), 5.22-5.18 (m, 6H), 5.92-5.81 (m, 3H), 7.56 (d, J=7.6 Hz, 4H), 7.69 (d, J=7.9 Hz, 2H), 8.10 (d, J=7.6 Hz, 4H), 8.15 (d, J=7.9 Hz, 2H), 8.76 (d, J=4.6 Hz, 2H), 8.83 (d, J=4.6 Hz, 2H), 8.88 (d, J=4.6 Hz, 2H), 8.96 (d, J=4.6 Hz, 2H); LD-MS obsd 866.2; FAB-MS obsd 866.3432, calcd 866.3422 ($C_{56}H_{43}F_{54}$); $λ_{abs}$ 418, 485, 515, 548, 588, 644 nm.

5-[4-(4-Allylhepta-1,6-dien-4-yl)phenyl]-10,20-di-p-tolyl-15-[4-[2-(trimethysilyl)ethoxycarbonyl]phenyl]porphinatozinc(II) (Zn-5)

Following a standard procedure (Id.), a solution of tin complex 19 (170 mg, 0.206 mmol) in dry THF/MeOH (20 mL, 10:1) was treated with $NaBH_4$ (390 mg, 10.3 mmol) in small portions with rapid stirring at room temperature. After 4 h, the reaction was quenched by slow addition of saturated aqueous $NH_4Cl$. The reaction mixture was extracted with $CH_2Cl_2$. The organic solution was dried ($Na_2SO_4$) and concentrated, affording 19-diol as a slightly yellow foam-like solid. The freshly prepared 19-diol was condensed with 16c (75.9 mg, 0.206 mmol) in $CH_2Cl_2$ (82 mL) containing $Yb(OTf)_3$ (162 mg, 3.2 mM, 0.261 mmol) at room temperature for 20 min. DDQ (139 mg, 0.61 mmol) was added and the reaction mixture was stirred for 1 h. TEA was added. The reaction mixture was filtered through a pad of alumina ($CH_2Cl_2$). The first fraction was collected and concentrated. The purple solid was dissolved in $CHCl_3$ (20 mL) and a solution of $Zn(OAc)_2 \cdot 2H_2O$ (300 mg, 1.37 mmol) in methanol (10 mL) was added. The reaction mixture was stirred overnight at room temperature. Chromatography (silica, $CH_2Cl_2$) afforded a purple solid. Methanol was added and the resulting suspension was sonicated. Filtration afforded a purple solid (24.4 mg, 12%): $^1H$ NMR: NMR δ 0.18 (s, 9H), 1.25-1.32 (m, 2H), 2.72 (s, 6H), 2.74 (d, J=7.0 Hz, 6H), 4.59 (t, J=8.42 Hz, 2H), 5.18-5.23 (m, 6H), 5.83-5.92 (m, 3H), 7.56 (d, J=7.7 Hz, 4H), 7.68 (d, J=8.1 Hz, 2H), 8.11 (d, J=7.7 Hz, 4H), 8.16 (d, J=8.1 Hz, 2H), 8.30 (d, J=8.4 Hz, 2H), 8.41 (d, J=8.1 Hz, 2H), 8.87 (d, J=4.8 Hz, 2H), 8.93 (d, J=4.8 Hz, 2H), 9.00 (d, J=4.8, 4H); LD-MS obsd 982.0; FAB-MS obsd 982.3628, calcd 982.3621 ($C_{62}H_{58}N_4O_2SiZn$); $λ_{ABS}$ 422, 549, 589 nm.

5,15-Bis[4-(4-allylhepta-1,6-dien-4-yl)phenyl]-10,20-dimesitylporphyrin (12)

Following a standard procedure (Littler et al. (1999) *J. Org. Chem.*, 64: 2864-2872), samples of 15b (17.9 mg, 0.074 mmol) and 16h (19.7 mg, 0.074 mmol) were reacted at room temperature in $CH_2Cl_2$ (7.5 mL) containing TFA (10 µL, 18 mM, 0.130 mmol). After 30 min, DDQ (30 mg, 15 mM, 0.13 mmol) was added, and the reaction mixture was stirred at room temperature for 1 h. The reaction mixture was neutralized by addition of TEA. The mixture was filtered through a pad of alumina ($CH_2Cl_2$). The filtrate was concentrated under reduced pressure. The residue was chromatographed (silica, $CH_2Cl_2$) to give a purple solid. The solid was suspended in methanol. The suspension was sonicated with methanol and filtered, affording a purple solid (16 mg, 44%): $^1H$ NMR δ-2.61 (s, 2H), 1.84 (s, 12H); 2.62 (s, 6H), 2.72 (d, J=7.3 Hz, 12H), 5.16-5.23 (m, 12H), 5.80-5.90 (m, 6H), 7.27 (s, 4H), 7.67 (d, J=8.2 Hz, 4H), 8.17 (d, J=8.4 Hz, 4H), 8.70 (d, J=4.8 Hz, 4H), 8.78 (d, J=4.8 Hz, 4H); LD-MS obsd 966.5; FAB-MS obsd 966.5612, calcd 966.5600 ($C_{70}H_{70}N_4$); $λ_{ABS}$ 419, 516, 550, 593, 647 nm.

5-[4-(N-(tert-Butyloxycarbonyl)amino)phenyl]-15-(5,5-dimethyl-1,3-dioxan-2-yl))porphinatozinc(II) (Zn-44)

Following a standard procedure (Fan et al. (2005) *Tetrahedron*, 61: 10291-10302), a solution of 16f (168 mg, 0.500 mmol) in $CH_2Cl_2$ (5.0 mL) was treated with N,N-dimethylmethyleneammonium iodide (Eschenmoser's reagent, in fine powder form, 194 mg, 1.05 mmol) at room temperature for 1 h. After standard workup, addition of hexanes/$CH_2Cl_2$ to the crude product afforded a precipitate, which upon filtration gave 5[4-(N-(tert-butyloxycarbonyl)amino)phenyl]-1,9-bis (N,N-dimethylaminomethyl)dipyrromethane (43) as a pale yellow solid (112 mg, 52%); $^1H$ NMR δ 1.49 (s, 9H), 2.24 (s, 12H); 3.40 3.51 (m, 4H), 5.33 (s, 1H), 5.745.76 (m, 2H), 5.925.94 (m, 2H), 6.58 (s, 1H), 7.12 (d, J=8.6 Hz, 2H), 7.25 (d, J=8.9 Hz, 2H), 8.68 (br, 1H); $^{13}$C NMR δ 28.4, 43.8, 44.8, 56.6, 107.0, 108.4, 118.9, 127.5, 129.1, 133.4, 137.1, 137.3; FAB-MS (LR) obsd 450.29, calcd 451.2947 ($C_{26}H_{37}N_5O_2$). A solution of 43 (230 mg, 0.500 mmol) and 16j (110 mg, 0.500 mmol) in ethanol (50 mL) at room temperature was treated with Zn(OAc)$_2$ 5.00 mmol) and heated to reflux. After 2 h the reaction mixture was allowed to cool to room temperature, a sample of DDQ (340 mg, 1.50 mmol) was added, and the mixture was stirred for 15 min. TEA (0.348 mL, 2.50 mmol) was added. The reaction mixture was concentrated and chromatographed [column 1: silica, CH$_2$Cl$_2$/ethyl acetate (3:2); column 2: silica, CH$_2$Cl$_2$/MeOH/TEA (50:20:1)] to give purple solid (32 mg, 10%); $^1$H NMR (THF-d$_8$) 1.15 (s, 3H), 1.64 (s, 9H), 2.00 (s, 3H), 4.27 (d, J=11.3 Hz, 2H), 4.44 (d, J=11.0 Hz, 2H), 7.93 (d, J=8.4 Hz, 2H), 8.11 (d, J=8.4 Hz, 2H), 8.17 (s, 1H); 8.92 (s, 1H); 9.08 (d, J=4.4 Hz, 2H), 9.36 (d, J=4.4 Hz, 2H), 9.45 (d, J=4.8 Hz, 2H), 10.22 (d, J=4.8 Hz, 2H), 10.24 (s, 2H); LD-MS obsd 677.7; FABMS obsd 677.2037, calcd 677.1981 ($C_{37}H_{35}N_5O_4Zn$); λ$_{ABS}$ 406, 536, 571 nm.

B. General Procedure for Porphyrin Metalation

5-[4-(4-Allylhepta-1,6-dien-4-yl)phenyl]-10,20-di-p-tolyl-15-(pentafluorophenyl)porphinatozinc(II) (Zn-2)

A solution of 2 (27 mg, 0.031 mmol) in CHCl3 (30 mL) was treated with a solution of Zn(OAc)$_2$.2H$_2$O (200 mg, 0.911 mmol) in methanol (6 mL). After stirring overnight at room temperature, the mixture was concentrated. The residue was dissolved in CH$_2$Cl$_2$. Chromatography (silica, CH$_2$Cl$_2$) afforded a purple powder (22 mg, 76%): $^1$H NMR δ 2.75-2.72 (overlapping peaks, 12H), 5.23-5.17 (m, 6H), 5.89-5.84 (m, 3H), 7.57 (d, J=7.6 Hz, 4H), 7.69 (d, J=7.9 Hz, 2H), 8.10 (d, J=7.6 Hz, 4H), 8.16 (d, J=7.9 Hz, 2H), 8.85 (d, J=4.6 Hz, 2H), 8.94 (d, J=4.6 Hz, 2H), 8.99 (d, J=4.6 Hz, 2H) 9.07 (d, J=4.6 Hz, 2H); LD-MS obsd 928.2; FAB-MS obsd 928.2527, calcd 928.2543 ($C_{56}H_{41}F_5N_4Zn$); λ$_{ABS}$ 419, 547 nm.

5-[4-(4-Allylhepta-1,6-dien-4-yl)phenyl]-15-bromo-10,20-di-p-tolylporphinatozinc(II) (Zn-4)

A solution of 4 (24 mg, 0.03 mmol) in CHCl$_3$ (25 mL) was treated with a solution of Zn(OAc)$_2$.2H$_2$O (300 mg, 1.37 mmol) in methanol (10 mL). The mixture was stirred overnight at room temperature. The mixture was poured into water, and the porphyrin product was extracted with CH$_2$Cl$_2$. The organic extracts were washed with aqueous NaHCO$_3$ and water and dried over Na$_2$SO$_4$. Chromatography (silica, CH$_2$Cl$_2$/hexanes 1:1) afforded a purple solid (23 mg, 89%): $^1$H NMR δ 2.72-2.75 (overlapping peaks 12H), 5.17-5.22 (m, 6H), 5.83-5.91 (m, 3H), 7.56 (d, J=7.7 Hz, 4H, 7.67 (d, J=8.4 Hz, 2H), 8.08 (d, J=7.7 Hz, 4H), 8.12 (d, J=8.1 Hz, 2H), 8.87 (d, J=4.8 Hz, 2H), 8.93 (d, J=4.8 Hz, 2H), 9.03 (d, J=4.8 Hz, 2H), 9.77 (d, J=4.8 Hz, 2H); LD-MS obsd 840.9; FAB-MS obsd 840.1868, calcd 840.1806 ($C_{50}H_{41}N_4BrZn$); λ$_{abs}$ 421, 552, 591 nm.

5-[4-(4-Allylhepta-1,6-dien-4-yl)phenyl]-15-(4-aminophenyl)-10,20-di-p-tolylporphinatocopper(II) (Cu-10)

A solution of 10 (7 mg, 0.009 mmol) in CHCl$_3$ (20 mL) was treated with a solution of Cu(OAc)$_2$ H$_2$O (50 mg, 0.25 mmol) in methanol (6 mL). The mixture was stirred overnight at room temperature. The mixture was poured into water, and the porphyrin product was extracted with CH$_2$Cl$_2$. The organic extract was washed (aqueous NaHCO$_3$ and water), dried (Na$_2$SO$_4$), concentrated, and chromatographed (silica, CH$_2$Cl$_2$), affording a purple solid (7 mg, 90%): $^1$H NMR δ 2.54 (s, 6H), 2.63 (br, 6H), 3.89 (s, 2H), 5.11 (br, 6H), 5.76 (br, 3H), 6.83 (br, 2H), 7.26 (br, 6H), 7.45 (br, 8H); MALDI-MS (dithranol) obsd 852.8; FAB-MS obsd 852.3193, calcd 852.3127 ($C_{56}H_{47}N_5Cu$) λ$_{abs}$ 419, 541, 578 nm.

C. Other Synthetic Procedures

5-[4-(4-Allylhepta-1,6-dien-4-yl)phenyl]-15-bromo-10,20-di-p-tolylporphyrin (4)

Following a standard procedure (Nudy et al. (1984) Tetrahedron 40: 2359-2363; (b) DiMagno et al. (1993) J. Org. Chem., 58: 5983-5993; Yu et al. (2003) Inorg. Chem., 42: 6629-6647), a solution of 3 (25.0 mg, 0.035 mmol) in CHCl$_3$ (12 mL) and pyridine (60 µL) was treated with NBS (10.0 mg, 0.057 mmol) at 0° C. After 30 min, the reaction was quenched with acetone (10 mL). The reaction mixture was washed with H$_2$O and dried (Na$_2$SO$_4$). Chromatography (silica, CH$_2$Cl$_2$) afforded purple solid (24.0 mg, 87%): $^1$H NMR δ-2.73 (s, 2H), 2.71-2.73 (m, 12H), 5.17-5.22 (m, 6H), 5.80-9.91 (m, 3H), 7.57 (d, J=7.7 Hz, 4H), 7.66 (d, J=8.4 Hz, 2H), 8.08 (d, J=7.7 Hz, 4H), 8.12 (d, J=8.1 Hz, 2H), 8.77 (d, J=4.8 Hz, 2H), 8.85 (d, J=4.8 Hz, 2H), 8.93 (d, J=4.8 Hz, 2H), 9.66 (d, J=4.8 Hz, 2H); LD-MS obsd 779.3; FAB-MS obsd 778.2721, calcd 778.2671 ($C_{50}H_{43}N_4Br$); λ$_{abs}$ 421, 519, 555, 597, 653 nm.

5-[4-(4-Allylhepta-1,6-dien-4-yl)phenyl]-15-(4-carboxyphenyl)-10,20-di-p-tolylporphinatozinc(II) (Zn-6)

A solution of Zn-15 (12 mg, 12 mmol) in DMF (10 mL) was treated with TBAF (60 µL, 1.0 M solution in THF) at room temperature for 3 h. The reaction mixture was washed with 10% NaHCO and water. The organic layer was dried (Na$_2$SO$_4$), concentrated, and chromatographed [silica, CHCl$_3$ then CH$_2$Cl$_2$/MeOH (3:1)]. The eluent was concentrated. The residue, was treated with a mixture of EtOH/hexanes (1:1) yielding a suspension that was sonicated. Filtration afforded a purple solid (8.0 mg, 75%): $^1$H NMR (THF-d$_8$) 2.68 (s, 6H), 2.78 (d, J=7.0 Hz, 6H), 5.15 5.23 (m, 6H), 5.87-5.97 (m, 3H), 7.56 (d, J=7.7 Hz, 2H), 7.76 (d, J=8.4 Hz, 4H), 8.07 (d, J=7.7 Hz, 4H), 8.16 (d, J=8.1 Hz, 2H), 8.27 (d, J=7.7 Hz, 2H), 8.41 (br, 2H), 8.82-8.87 (overlapping peaks, 8H); LD-MS obsd 881.8; FAB-MS obsd 882.2912, calcd 882.2912 ($C_{57}H_{46}N_4O_2Zn$); λ$_{abs}$ (THF) 424, 557, 587 nm.

5-[4-(4-Allylhepta-1,6-dien-4-yl)phenyl]-15-(4-aminophenyl)-10,20-di-p-tolylporphyrin (10)

A solution of 9 (20.0 mg, 0.022 mmol) in CHCl$_3$ (20 mL) was treated with TFA (5 mL) at 0° C. The mixture was stirred for 45 min. Then the mixture was poured into water, and the porphyrin product was extracted with CH$_2$Cl$_2$. The organic extract was washed (aqueous NaHCO$_3$ and water), dried (Na$_2$SO$_4$), concentrated, and chromatographed (silica, CH$_2$Cl$_2$), affording purple solid (17 mg, 96%): $^1$H NMR δ-2.75 (s, 2H), 2.71 (s, 6H), 2.73 (d, J=7.0 Hz, 6H), 4.01 (s, 2H), 5.17-5.22 (m, 6H), 5.83-5.92 (m, 3H), 7.06 (d, J=8.1 Hz, 2H), 7.55 (d, J=8.1 Hz, 4H), 7.68 (d, J=8.4 Hz, 2H), 8.00 (d, J=8.4 Hz, 2H), 8.10 (d, J=7.7 Hz, 4H), 8.16 (d, J=8.1 Hz, 2H), 8.81 (d, J=4.8, 2H), 8.86-8.88 (m, 4H), 8.91 (d, J=4.8 Hz, 2H);

LD-MS obsd 791.4; FAB-MS obsd 792.4125, calcd 792.4066 [(M+H)$^+$; C$_{56}$H$_{49}$N$_5$]; $\lambda_{abs}$ 422, 519, 555, 593, 649 nm.

5-[4-(N-(tert-Butoxycarbonyl)amino)phenyl]dipyrromethane (16f)

Following a general procedure (Littler et al. (1999) *J. Org. Chem.*, 64: 1391-1396), a mixture of 15f (2.00 g, 9.04 mmol) and pyrrole (16 mL, 0.23 mol) was treated with TFA (70 µL, 0.90 mmol) and stirred at room temperature for 30 min. 0.1 M NaOH (20 mL) and ethyl acetate (50 mL) were added, and the organic layer was separated. After washing with brine and water, the organic extract was dried (Na$_2$SO$_4$) and concentrated. The resulting brown residue was chromatographed (silica, CH$_2$Cl$_2$) to obtain a pale yellow solid (2.48 g, 81%): mp 141-144° C. (dec.); $^1$H NMR δ 1.51 (s, 9H), 7.43 (s, 1H), 5.92 (m, 2H), 6.14-6.16 (m, 2H), 6.46 (m, 1H), 6.69-6.70 (m, 2H), 7.14 (d, J=8.4 Hz, 2H), 7.30 (d, J=8.4 Hz, 2H), 7.93 (br, 2H); $^{13}$C NMR 28.3, 43.3, 80.6, 107.1, 108.4, 117.1, 118.9, 128.9, 132.5, 136.7, 137.1, 152.8; FAB-MS obsd 337.1791; calcd 337.1790 (C$_{20}$H$_{23}$F$_3$O$_2$).

5-(4-Amino-3,5-dimethylphenyl)dipyrromethane (16g)

Following a general procedure (Littler et al. (1999) *J. Org. Chem.*, 64: 1391-1396), a mixture of 15g aldehyde (500 mg, 3.35 mmol) and pyrrole (16 mL, 0.23 mol) was treated with TFA (70 µL, 0.90 mmol) and stirred at room temperature for 16 h. The mixture was concentrated. Chromatography (silica, CH$_2$Cl$_2$) gave unreacted aldehyde followed by the title compound as a pale yellow solid (175 mg, 20%): mp 137-143° C. (dec.); $^1$H NMR δ 2.14 (s, 6H), 3.47 (s, 2H), 5.34 (s, 1H), 5.94-5.95 (m, 2H), 6.15-6.16 (m, 2H), 6.67-6.68 (m, 2H), 6.81 (s, 2H), 7.90 (br, 2H); $^{13}$C NMR δ 17.9, 43.4, 106.9, 108.5, 117.0, 122.2, 128.4. 133.5, 141.8; FAB-MS obsd 265.1572; calcd 265.1579 (C$_{17}$H$_{19}$N$_3$).

Dibutyl[5,10-dihydro-5-(pentafluorophenyl)-1,9-di-p-toluoyldipyrrinato]tin(IV) (17)

Following a standard procedure (Tamaru et al. (2004) *J. Org. Chem.*, 69: 765-777), EtMgBr (6.4 mL, 6.4 mmol, 1.0 M in THF) was added slowly to a tap-water cooled flask containing a solution of (400 mg, 1.28 mmol) in toluene (25 mL) under argon. The reaction mixture was stirred at room temperature for 30 min. A sample of p-toluoyl chloride (0.42 mL, 3.2 mmol) was added over 10 min. The mixture was stirred for an additional 1 h and then was poured into a mixture of saturated aqueous NH$_4$Cl and ethyl acetate. The organic layer was washed (water and brine), dried (Na$_2$SO$_4$), and concentrated to dryness. The residue was treated with TEA (0.4 mL) and Bu$_2$SnCl$_2$ (389 mg, 1.28 mmol) in CH$_2$Cl$_2$ (15 mL). The mixture was stirred at room temperature for 30 min and then concentrated. Chromatography [silica, CH$_2$Cl$_2$/hexanes (3:1)] and then crystallization (diethyl ether/methanol) afforded pale pink crystals (180 mg; 18%): mp 139-142° C. (dec.); $^1$H NMR δ 0.72 (t, J=7.3 Hz, 3H), 0.75 (t, J=7.3 Hz, 3H), 1.25-1.15 (m, 4H), 1.48-1.34 (m, 4H), 1.63-1.55 (m, 4H), 2.45 (s, 6H), 7.01 (d, J=3.8 Hz, 2H), 6.12 (s, 1H), 7.01 (d, J=3.8 Hz, 2H), 7.30 (d, J=8.0 Hz, 4H), 7.83 (d, J 8.0 Hz, 4H); $^{13}$C NMR δ 13.7, 13.8, 21.8, 24.4, 24.7, 26.3, 26.4, 27.2, 25.5, 34.1, 114.0, 123.7, 129.3, 129.4, 134.9, 135.7, 142.6, 147.3, 185.2; FAB-MS obsd 781.1915, calcd 781.1875 [(M+H)$^+$; M=C$_{39}$H$_{37}$F$_5$N$_2$O$_2$Sn]; Anal Calcd for C$_{39}$H$_{37}$F$_5$N$_2$O$_2$Sn: C, 60.10; H, 4.78; N, 3.59. Found: C, 60.12; H, 4.76; N, 3.67.

5-(4-Hydroxymethylbiphen-4'-yl)-10,15,20-tri-p-tolylporphyinatozinc(II) (Zn-28)

Following a standard procedure (Yu and Lindsey (2001) *Tetrahedron* 57: 9285-9298; Zhou and Chan (1994) *J. Chem. Soc., Chem. Commun.*, 2493-2494), a mixture of Zn-26 (100 mg, 0.125 mmol), 4-(hydroxymethyl)phenylboronic acid (27) (38.0 mg, 0.250 mmol), anhydrous K$_2$CO$_3$ (138 mg, 0.998 mmol) and Pd(PPh$_3$)$_4$ (21.7 mg, 0.0188 mmol) in DMF/toluene (12.5 mL) was reacted at 85° C. for 16 h using Schlenk techniques. The reaction mixture was concentrated to dryness. The resulting crude product was chromatographed (silica, CH$_2$Cl$_2$), affording a purple solid (93.0 mg, 90%): $^1$H NMR (THF-d$_8$) 2.54 (s, 6H), 2.69 (s, 3H), 4.32 (t, J=6.0 Hz, 1H), 4.71 (d, J=6.0 Hz, 2H), 7.56 (d, J=7.6 Hz, 8H), 7.93 (d, J=8.0 Hz, 2H), 8.04 (d, J=7.6 Hz, 2H), 8.08 (d, J=8.0 Hz, 6H), 8.26 (d, J=7.6 Hz, 2H), 8.84 (s, 4H), 8.87 (d, J=4.8 Hz, 2H), 8.92 (d, J=4.8 Hz, 2H); LD-MS obsd 824.5; FAB-MS obsd 824.2430 calcd 824.2494 (C$_{54}$H$_{40}$N$_4$OZn); $\lambda_{abs}$ (toluene) 425, 552, 593 nm; $\lambda_{em}$ ($\lambda_{ex}$ 550 nm) 603, 650 nm.

5-(4-Isothiocyanatophenyl)-10,15,20-trimesitylporphinatozinc(II) (Zn-30)

A solution of 29 (40 mg, 0.053 mmol) in CHCl$_3$ (5 mL) was treated with a solution of Zn(OAc)$_2$.2H$_2$O (58 mg, 0.26 mmol) in methanol (1 mL) with stirring at room temperature for 15 h. Chromatography [silica, CHCl$_3$/THF (98:2)] afforded 5-(4-aminophenyl)-10,15,20-trimesitylporphinatozinc(II) (Zn-29) as a purple solid (41 mg, 95%). Following a literature procedure (Sutton et al. (2002) *Bioconjugate Chem.*, 13: 249-263), a solution of this sample of Zn-29 (40 mg, 0.049 mmol) in dry CH$_2$Cl$_2$ (10 mL) was treated with 1,1-thiocarbonyldi-2(1H)-pyridone (TDP) (23 mg, 0.098 mmol) with stirring at room temperature under argon for 2 h. Chromatography (silica, CH$_2$Cl$_2$) afforded a purple solid (42 mg, 100%): $^1$H NMR (300 MHz, CD$_2$Cl$_2$) δ 1.83-1.86 (overlapping peaks, 18H), 2.63 (s, 9H), 7.31 (s, 6H), 7.65 (d, J=8.4 Hz, 2H), 8.24 (d, J=8.1 Hz, 2H), 8.70-8.75 (m, 4H), 8.77 (d, J=4.8 Hz, 2H), 8.84 (d, J=4.5 Hz, 2H); LD-MS obsd 860.1; FAB-MS obsd 859.2712, calcd 859.2687 (C$_{54}$H$_{45}$N$_5$SZn); $\lambda_{abs}$ (toluene) 423, 550 nm.

5,15-Dibromo-10,20-dimesitylporphinatozinc(II) (Zn-31)

Following a standard procedure (Nudy et al. (1984) *Tetrahedron* 40: 2359-2363; (b) DiMagno et al. (1993) *J. Org. Chem.*, 58: 5983-5993; Yu et al. (2003) *Inorg. Chem.*, 42: 6629-6647), a solution of 38 (50 mg, 0.091 mmol) in CHCl$_3$ (30 mL) and pyridine (40 µL) was treated with NBS (40 mg, 0.23 mmol) at 0° C. After 1 h the reaction was quenched by addition of acetone (5 mL). The reaction mixture was washed with H$_2$O, dried (Na$_2$SO$_4$) and concentrated. The crude solid was dissolved in CHCl$_3$ (20 mL) and treated overnight at room temperature with a solution of Zn(OAc)$_2$.2H$_2$O (200 mg, 0.911 mmol) in methanol (6 mL). Chromatography [silica, CHCl$_3$/hexanes (1:2)] afforded a purple solid (50 mg, 71%): $^1$H NMR (THF-d$_8$) 1.84 (s, 12H), 2.64 (s, 6H), 7.33 (s, 4H); 8.67 (d, J=4.8 Hz, 4H); 9.59 (d, J=4.4 Hz, 4H); LD-MS obsd 767.4; FAB-MS obsd 764.0140, calcd 764.0129 (C$_{38}$H$_{30}$Br$_2$N$_4$Zn); $\lambda_{abs}$ (THF) 428, 565, 607 nm.

5,15-Bis[(4-hydroxymethyl)phenyl]-10,20-dimesitylporphinatozinc(II) (Zn-32)

A solution of Zn-39 (28 mg, 0.032 mmol) in dry THF (15 mL) was treated with LiAlH$_4$ (20 mg, 0.53 mmol) under argon at room temperature for 1 h. Methanol was slowly added to destroy the excess LiAlH$_4$. The solvent was evaporated under reduced pressure. Chromatography (silica, CH$_2$Cl$_2$) afforded a purple powder (21 mg, 80%): $^1$H NMR δ 1.83 (s, 12H), 2.63 (s, 6H), 4.95 (d, J=5.12 Hz, 4H), 7.28 (s, 4H), 7.68 (d, J=7.7 Hz, 4H), 8.22 (d, J=8.1 Hz, 4H), 8.77 (d, J=4.4 Hz, 4H), 8.87 (d, J=4.8 Hz, 4H); LD-MS obsd 820.3; FAB-MS obsd 820.2736, calcd 820.2756 (C$_{52}$H$_{44}$N$_4$O$_2$Zn); λ$_{abs}$ 420, 548 nm.

5,15-Bis[4-(cyanomethyl)phenyl]-10,20-dimesitylporphinatozinc(II) (Zn-33)

Following a standard procedure (Cook et al. (1974) *J. Org. Chem.*, 39: 3416-3418), a solution of Zn-40 (20 mg, 0.022 mmol) in acetonitrile/THF [20 mL, 1:1] was treated with KCN (24 mg, 0.37 mmol) and 18-crown-6 (3 mg, 0.01 mmol) with stirring at room temperature for 2 days. The reaction mixture was concentrated and chromatographed (silica, CH$_2$Cl$_2$) to give a purple solid (17 mg, 96%): $^1$H NMR δ 1.83 (s, 12H), 2.61 (s, 6H), 4.24 (s, 4H), 7.30 (s, 4H), 7.75 (d, J=7.7 Hz, 4H), 8.21 (d, J=8.1 Hz, 4H), 8.67 (d, J=4.4 Hz, 4H), 8.78 (d, J=4.4 Hz, 4H) LD-MS obsd 838.5; FAB-MS obsd 838.2768, calcd 838.2762 (C$_{54}$H$_{42}$N$_6$Zn); λ$_{abs}$ (THF) 423, 557, 596 nm; λ$_{abs}$ 421, 549 nm.

5,15-Bis(4-aminophenyl)-10,20-dimesitylporphyrin (34)

A solution of 41 (60 mg, 0.065 mmol) in CHCl$_3$(20 mL) was treated with TFA (5 mL) at 0° C. with stirring for 45 min at room temperature. The mixture was poured into water, and the porphyrin product was extracted with CH$_2$Cl$_2$. The organic extract was washed (aqueous NaHCO$_3$ and water), dried (Na$_2$SO$_4$), concentrated, and chromatographed (silica, CH$_2$Cl$_2$) to give a purple solid (47 mg, 99%): $^1$H NMR δ-2.59 (s, 2H), 1.84 (s, 12H), 2.63 (s, 6H), 4.02 (s, 4H); 7.06 (d, J=8.1 Hz, 4H), 7.28 (s, 4H), 7.99 (d, J=8.1 Hz, 4H), 8.66 (d, J=4.8 Hz, 4H), 8.87 (d, J=4.8 Hz, 4H); LD-MS obsd 728.9; FAB-MS obsd 729.3712, calcd 729.3706 [(M+H)$^+$; M=C$_{50}$H$_{44}$N$_6$); λ$_{abs}$ 423, 519, 556, 595, 652 nm.

5,15-Bis(4-isothiocyanatophenyl)-10,20-dimesitylporphyrin (35)

Following a literature procedure (Kim and Yi (1985) *Tetrahedron Lett.*, 26: 1661-1664; (b) Han et al. (1996) *Langmuir* 12: 5742-5744), a solution of 34 (32 mg, 0.044 mmol) in CHCl (20 mL) was treated with di-2-pyridyl thiocarbonate (DPTC) (21 mg, 0.090 mmol) with stirring at room temperature. TLC analysis (silica, CH2Cl12) after 2 h indicated incomplete reaction, whereupon additional DPTC (10 mg, 0.043 mmol) was added. The reaction mixture was stirred for 1 h. The reaction mixture was concentrated and chromatographed (silica, CH$_2$Cl$_2$) to give a purple solid (26 mg, 73%): $^1$H NMR δ-2.65 (s, 2H), 1.84 (s, 12H), 2.64 (s, 6H), 7.30 (s, 4H), 7.62 (d, J=8.1 Hz, 4H), 8.21 (d, J=8.4 Hz, 4H), 8.73-8.75 (m, 8H); LD-MS obsd 812.7; FAB-MS obsd 813.2823, calcd 813.2834 [(M+H)$^+$; M=C$_{52}$H$_{40}$N$_6$S$_2$]; λ$_{abs}$ (THF) 420, 516, 551, 559, 647, 601 nm.

5,15-Diformyl-10,20-di-p-tolylporphinatozinc(II) (Zn-37)

Following a standard procedure (Balakumar et al. (2004) *J. Org. Chem.* 69: 5112-5115), a solution of 42 (20.0 mg, 0.028 mmol) in CH$_2$Cl$_2$(24 mL) was treated with TFA/H$_2$O (2.8 mL, 2:1) at room temperature. TLC analysis after 16 h indicated incomplete reaction. An additional amount of TFA/H2O [5 mL (2:1)] was added, and the reaction mixture was stirred at room temperature for 16 h. After standard workup the crude 37 was dissolved in CHCl$_3$(20 mL) and treated overnight with a solution of Zn(OAc)$_2$.2H$_2$O (100 mg, 0.456 mmol) in methanol (6 mL) at room temperature. The product obtained upon chromatography (silica, CH$_2$Cl$_2$) was washed with hexanes and with ethanol, affording a purple powder (10.0 mg, 60%): $^1$H NMR (THF-d$_8$) 2.73 (s, 6H), 7.62 (d, J=7.3 Hz, 4H), 8.07 (d, J=8.1 Hz, 4H), 8.97 (d, J=4.8 Hz, 4H) 10.16 (d, J=4.8 Hz, 4H), 12.65 (s, 2H) LD-MS obsd 608.7; FAB-MS obsd 608.1211, calcd 608.1191 (C$_{36}$H$_{24}$N$_4$O$_2$Zn); λ$_{abs}$ (THF) 432, 633 nm.

5-(4-Aminophenyl)-15-formylporphinatozinc(II) (Zn-45)

A solution of Zn-44 (20 mg, 0.029 mmol) in CH$_2$Cl$_2$ (20 mL) was treated with TFA/H$_2$O (1.4 mL, 1:1) at room temperature for 16 h. The organic layer was washed (5% aqueous NaHCO3 and water), dried (Na$_2$SO$_4$), and concentrated. (The $^1$H NMR spectrum showed incomplete deprotection of the amino group). The solid was dissolved in CH$_2$Cl$_2$ (20 mL) and TFA (4 mL) was slowly added. After 1 h, the organic layer was washed (5% aqueous NaHCO$_3$ and water), dried (Na$_2$SO$_4$) and concentrated. The resulting residue was dissolved in CHCl$_3$ (20 mL) and treated with Zn(OAc)$_2$ 2H$_2$O (200 mg, 0.911 mmol) at room temperature for 16 h. Chromatography (silica, CH$_2$Cl$_2$) afforded a purple-green solid, which proved somewhat unstable on chromatography (3 mg, 20%): $^1$H NMR (THF-d$_8$) 5.00 (br, 2H), 7.01 (d, J=8.4 Hz, 2H), 7.88 (d, J=8.1 Hz, 2H), 9.07 (d, J=4.4, 2H); 9.25 (d, J=4.4 Hz, 2H), 9.48 (d, J=4.4 Hz, 2H), 10.20 (s, 2H), 10.30 (d, J=4.8 Hz, 2H), 12.61 (s, 1H); MALDI-MS (dithranol) obsd 491.3; calcd 491.1 (C$_{27}$H$_{17}$N$_5$O); λ$_{abs}$ (THF) 421, 557, 597 nm.

D. Physical Studies

Materials.

The substrates for surface attachment were prepared from commercially available highly doped p-type Si(100) wafers. The anhydrous solvents and chemicals used in the preparation of the porphyrin monolayers, the in situ assembly studies, and the electrochemical and FTIR characterization include benzonitrile, CH$_2$Cl$_2$, N,N-dimethylacetamide (DMAc), 3,3',4,4'-biphenyltetracarboxylic dianhydride (BPTC), 4,4'-methylenedianiline (MDA) and 4,4'-methylene-bis(2,6-dimethylaniline) (MMDA); all were used as received. The propylene carbonate used for the electrochemical studies was dried on molecular sieves before use. The Bu$_4$NPF$_6$ supporting electrolyte was recrystallized three times from methanol and dried at 110° C. under vacuum.

Porphyrin Monolayer Preparation.

The porphyrin monolayers on Si(100) were prepared using a high-temperature (400° C.), short time (2 min) "baking" attachment procedure described previously. The monolayers for the electrochemical experiments were prepared by dispensing a 2 µL drop of the porphyrin solution onto the surface of a microelectrode contained in a sparged VOC vial sealed under Ar. The monolayers prepared for the FTIR experiments utilized much larger platforms (~1 cm$^2$), and consequently required a larger drop size, ~50 µL. After deposition, the vial containing the Si substrate was heated on a hotplate at 400° C. for 2 min and then removed and purged with Ar until cooling to room temperature. Finally, the Si substrate was rinsed, sonicated five times with anhydrous CH$_2$Cl$_2$, and purged dry with Ar.

In Situ Assembly Studies.

The studies of in situ formation of porphyrin dyads were performed by first preparing a particular porphyrin monolayer as described above. The cleaned and washed substrate was then placed in a sealed vial, purged with Ar, and a drop of the solution containing the second porphyrin was introduced (5 μL and 50 μL for the electrochemical and FTIR substrates, respectively). After deposition, the vial containing the Si substrate was heated on a hotplate at 400° C. for 2 min and then removed and purged with Ar until cooling to room temperature. Finally, the Si substrate was rinsed, sonicated five times with anhydrous $CH_2Cl_2$, and purged dry with Ar.

The studies of in situ formation of polyimides on the monolayers followed the same general procedure as described above for the porphyrin dyads with the following modifications. (1) After deposition of the BPTC solution (5 mM in DMAc) onto the porphyrin-modified substrate, the substrate was heated on a hotplate at 280° C. for 2 min, then removed and purged under Ar until cooling to room temperature, washed and sonicated with $CH_2Cl_2$, and dried with Ar. (2) After electrochemical or spectroscopic interrogation, the sample was again washed and dried, and a solution of DMA/MMDA (5 mM in DMAc) was introduced onto the substrate. The sample was then heated at 280° C. for 2 min, removed and purged under Ar until cooling to room temperature, washed and sonicated with $CH_2Cl_2$, and dried with Ar. (3) After the second electrochemical and spectroscopic interrogation, the sample was rewashed and dried and the above procedure was repeated with alternating doses of BPTC and MDA/MMDA.

Electrochemical Measurements.

The electrochemical measurements of the porphyrins in solution were made in a standard three-electrode cell using Pt working and counter electrodes and a $Ag/Ag^+$ reference electrode. The solvent/electrolyte was $CH_2Cl_2$ containing 0.1 M n-$Bu_4NPF_6$.

The electrochemical measurements on the porphyrin monolayers were performed in a two electrode configuration using highly doped p-type Si(100) working electrodes (100 100 μm) and an Ag counter/reference electrode, fabricated as described earlier (Roth et al. (2003) *J. Am. Chem. Soc.*, 125: 505-517). Propylene carbonate containing 1.0 M n-$Bu_4NPF_6$ was used as solvent/electrolyte. The cyclic voltammograms were recorded using a Gamry Instruments PC4-FAS1 femtostat running PHE 200 framework and Echem Analyst software. The charge density in the monolayer was determined by integration of the total charge of both anodic waves and by using the geometrical dimensions of the microelectrode. The surface coverage of the porphyrin monomers and dyads was determined by scaling the charge density by a factor of two or four, respectively.

FTIR Spectroscopy.

The FTIR spectra of the porphyrins in both solid and monolayer forms were collected at room temperature with a spectral resolution 4 $cm^{-1}$. The spectra of the solid porphyrin samples were obtained in KBr pellets (~1-2 wt % porphyrin). These spectra were collected in transmission mode using a room-temperature DTGS detector by averaging over 32 scans.

The IR spectra of the monolayers were obtained using a Harrick Scientific horizontal reflection Ge attenuated total reflection accessory (GATR, 65° incidence angle). The Si substrates were placed in contact with the flat surface of a semispherical Ge crystal that serves as the optical element, and IR spectra were collected with p polarized light using a liquid-nitrogen cooled medium-bandwidth MCT detector (600-4000 $cm^{-1}$) and averaging 256 scans. The Ge crystal was cleaned with neat 2-butanone before every experiment, and the GATR accessory was purged with dry $N_2$ during data acquisition. The spectra of porphyrin monolayers were referenced against that of a hydrogen-terminated Si(100) surface previously subjected to the same deposition conditions as those used to obtain the monolayer but using only the neat deposition solvent.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of forming an oligomeric molecule in situ on an electrode substrate, said method comprising:
    a) providing an electrode substrate having attached thereto a linker bearing a free reactive group A or a first monomer $M^1$ bearing a free reactive group A;
    b) contacting said linker or said first monomer with a second monomer having the formula B-$M^2$-B comprising two identical free reactive groups B where B is reactive with A, whereby said second monomer couples to said linker or first monomer via a reaction between A and one of the reactive groups B; and
    c) contacting said second monomer with a third monomer having the formula A-$M^3$-A comprising two identical free reactive groups, wherein $M^1$ when present, $M^2$ and $M^3$ are independently selected from the group consisting of a charge storage moiety, a charge separation moiety, a spacer, an electrolyte, whereby said third monomer couples to said second monomer via a reaction between one of reactive groups A, and a the free reactive group B on said second monomer, thereby forming an oligomeric molecule attached to said substrate, and where said oligomeric molecule is formed without the use of protecting groups.

2. The method of claim 1, wherein said providing comprises coupling a first monomer to said substrate wherein said first monomer after coupling to said surface provides a free reactive group A.

3. The method of claim 1, further comprising repeating step (b) and/or step (c) one or more times to further extend said oligomeric molecule.

4. The method of claim 1, wherein said method further comprises performing a cross-linking reaction after coupling each monomer.

5. The method of claim 1, wherein $M^2$ and $M^3$ are the same.

6. The method of claim 1, wherein A and B are pairs of reactive groups selected from Table 1.

7. The method of claim 1, wherein $M^2$ and $M^3$ are joined by a linkage selected from the group consisting of acyl hydrazone, imine, salicylaldimine, H-bonded acyl hydrazone, vinyl, urea, carbamate, carboxy amide, imide, thiourea, thiocarbamate, amide-alkyl-thiol, ether, ether, phenacyl ether, α-ether-acetamide, α-ester-acetamide, amide, sulfonamide, alkyl boronate, thioether, acetal, and hydroxyalkylamine.

8. The method of claim 1, wherein $M^2$ and $M^3$ are charge storage moieties comprising a redox-active molecule.

9. The method of claim 8, wherein $M^2$ and $M^3$ are redox-active molecules selected from the group consisting of porphyrinic macrocycle, a sandwich compound of porphyrinic macrocycles, a lanthanide triple decker sandwich coordination compound, and a metallocene.

10. The method of claim 9, wherein $M^2$ and $M^3$ are redox-active porphyrinic macrocycles independently selected from the group consisting of porphyrins, chlorins, bacteriochlorins, isobacteriochlorins, oxochlorins, dioxobacteriochlorins, dioxoisobacteriochlorins, pyrophorbines, bacteriopyrophorbines, phthalocyanines, naphthalocyanines, tetraazaporphyrins, porphyrazines, benzazoloporphyrazines, core modified porphyrinic derivatives, expanded porphyrinic derivatives, and contracted porphyrinic derivatives.

11. The method of claim 1, wherein said method forms an oligomeric molecule ranging in length from 2 to about 20 monomers.

12. The method of claim 11, wherein the monomers comprising said oligomeric molecule are joined by a linkage selected from the group consisting of acyl hydrazone, imine, salicylaldimine, H-bonded acyl hydrazone, vinyl, urea, carbamate, carboxy amide, imide, thiourea, thiocarbamate, amide-alkyl-thiol, ether, ether, phenacyl ether, α-ether-acetamide, α-ester-acetamide, amide, sulfonamide, alkyl boronate, thioether, acetal, and hydroxyalkylamine.

13. The method of claim 11, wherein said substrate comprises an electrode and said substrate and oligomeric molecule form a light harvesting rod.

14. The method of claim 13, wherein said substrate and oligomeric molecule form an intrinsic rectifier of excited-state energy.

15. The method of claim 13, wherein said substrate and oligomeric molecule form an intrinsic rectifier of holes.

16. The method of claim 13, wherein said substrate and oligomeric molecule form light harvesting rods are not greater than 500 nanometers in length.

17. The method of claim 11, wherein said substrate comprises a first electrode and said oligomeric molecule and substrate forms a molecular memory element.

18. The method of claim 11, wherein said oligomeric molecule comprises at least two meso-coupled porphyrinic macrocycles.

19. The method of claim 11, wherein said oligomeric molecule comprises at least two beta-coupled porphyrinic macrocycles.

20. The method of claim 1, wherein said substrate is selected from the group consisting of a transparent substrate, an opaque substrate and a reflective substrate.

21. The method of claim 1, wherein $M^1$, $M^2$, and/or $M^3$, have the formula:

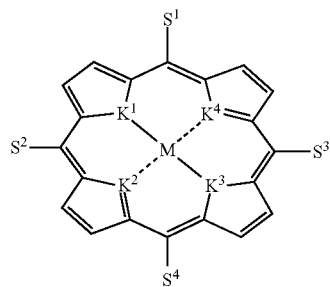

wherein:

M is present or absent and when present is selected from the group consisting of a metal, and a metalloid;

$K^1$, $K^2$, $K^3$, and $K^4$ are independently selected from the group consisting of a group IV element, a group V element, a group VI element, and CH;

$S^1$, $S^2$, $S^3$, and $S^4$ are substituents independently selected from the group consisting of aryl, phenyl, cycloalkyl, alkyl, halogen, alkoxy, alkylthio, perfluoroalkyl, alkenyl, alkynyl, perfluoroaryl, pyridyl, cyano, thiocyanato, nitro, amino, alkylamino, acyl, sulfoxyl, sulfonyl, imido, amido, imidazolyl, and carbamoyl, wherein said substituents provide a redox potential range of less than about 2 volts.

22. The method of claim 21, wherein $K^1$, $K^2$, $K^3$, and $K^4$ are independently selected from the group consisting of N, O, S, Se, Te, and CH.

23. The method of claim 21, wherein M is present and is selected from the group consisting of Zn, Mg, Cd, Hg, Cu, Ag, Au, Ni, Pd, Pt, Co, Rh, Ir, Mn, B, Al, Ga, Pb, and Sn.

24. The method of claim 21, wherein M is selected from the group consisting of Zn, Mg, and Ni.

25. The method of claim 21, wherein $S^1$, $S^2$, $S^3$, $S^4$ are all the same.

26. The method of claim 21, wherein $S^1$ and $S^4$ are the same.

27. The method of claim 26, wherein $S^2$ and $S^3$ are the same.

28. The method of claim 21, wherein $K^1$, $K^2$, $K^3$, and $K^4$ are all the same.

29. The method of claim 21, wherein $K^1$, $K^2$, $K^3$, and $K^4$ are all N.

30. The method of claim 1, wherein said substrate comprises a material selected from the group consisting of silicon, germanium, silver, gold, copper, titanium, tantalum, tungsten, a doped silicon, a doped germanium, a silicon oxide, a germanium oxide, a silver oxide, a gold oxide, a copper oxide, a titanium oxide, a tantalum oxide, a tungsten oxide, a silicon nitride, a germanium nitride, a silver nitride, a gold nitride, a copper nitride, a titanium nitride, a tantalum nitride, a tungsten nitride, a carbon containing substrate, and a polymer.

31. The method of claim 30, wherein said substrate comprises Si(100).

* * * * *